United States Patent
Yoshida et al.

(10) Patent No.: US 7,858,788 B2
(45) Date of Patent: Dec. 28, 2010

(54) BICYCLIC CARBAMOYLPYRIDONE DERIVATIVE HAVING HIV INTEGRASE INHIBITORY ACTIVITY

(75) Inventors: Hiroshi Yoshida, Osaka (JP); Takashi Kawasuji, Osaka (JP); Yoshiyuki Taoda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 354 days.

(21) Appl. No.: 11/884,686

(22) PCT Filed: Feb. 20, 2006

(86) PCT No.: PCT/JP2006/302925

§ 371 (c)(1),
(2), (4) Date: Aug. 20, 2007

(87) PCT Pub. No.: WO2006/088173

PCT Pub. Date: Aug. 24, 2006

(65) Prior Publication Data

US 2008/0161271 A1  Jul. 3, 2008

(30) Foreign Application Priority Data

| Feb. 21, 2005 | (JP) | ............... | 2005-043310 |
| Apr. 28, 2005 | (JP) | ............... | 2005-131161 |
| Oct. 27, 2005 | (JP) | ............... | 2005-312076 |

(51) Int. Cl.
C07D 413/00 (2006.01)
C07D 471/00 (2006.01)

(52) U.S. Cl. .................. 544/350; 544/117

(58) Field of Classification Search ............ 544/117, 544/350
See application file for complete search history.

(56) References Cited

U.S. PATENT DOCUMENTS

| 7,211,572 | B2 * | 5/2007 | Miyazaki et al. ...... 514/211.04 |
| 2003/0055071 | A1 | 3/2003 | Anthony et al. |
| 2004/0110804 | A1 | 6/2004 | Walker et al. |
| 2004/0229909 | A1 | 11/2004 | Kiyama et al. |
| 2005/0054645 | A1 | 3/2005 | Miyazaki et al. |
| 2005/0176718 | A1 | 8/2005 | Anthony et al. |
| 2006/0046985 | A1 | 3/2006 | Crescenzi et al. |
| 2006/0052361 | A1 * | 3/2006 | Miyazaki et al. ...... 514/211.04 |
| 2006/0128669 | A1 | 6/2006 | Murai et al. |
| 2006/0247212 | A1 | 11/2006 | Murai et al. |

FOREIGN PATENT DOCUMENTS

| JP | 2-96506 | 4/1990 |
| JP | 2-108668 | 4/1990 |
| JP | 2-108683 | 4/1990 |
| JP | 2004-244320 | 9/2004 |
| WO | 03/035076 | 5/2003 |
| WO | WO 2006/066414 A1 * | 6/2006 |

* cited by examiner

*Primary Examiner*—Nizal S Chandrakumar
(74) *Attorney, Agent, or Firm*—Wenderoth, Lind & Ponack, L.L.P.

(57) ABSTRACT

Is to provide a novel compound having an anti-viral activity, particularly a HIV integrase inhibitory activity, and an agent, particularly an anti-HIV agent.

A compound represented by the formula:

[Chemical formula 1]

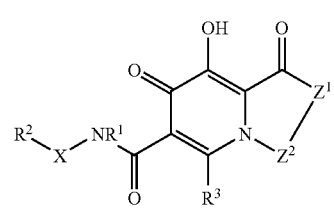

(wherein
$Z^1$ is $NR^4$ ($R^4$ is hydrogen, optionally substituted lower alkyl etc.), O or $CH_2$;
$Z^2$ is optionally substituted lower alkylene or optionally substituted lower alkenylene, each may be intervened by a heteroatom group selected from group consisting O, S, SO, $SO_2$, $NR^5$ ($R^5$ is selected independently from the same substituent group of $R^4$) —N= and =N—;
$R^1$ is hydrogen or lower alkyl;
X is a single bond, a heteroatom group selected from O, S, SO, $SO_2$ and NH, or lower alkylene or lower alkenylene each may be intervened by the heteroatom group;
$R^2$ is optionally substituted aryl;
$R^3$ is hydrogen, halogen, hydroxy, optionally substituted alkyl group etc.)

3 Claims, No Drawings

BICYCLIC CARBAMOYLPYRIDONE DERIVATIVE HAVING HIV INTEGRASE INHIBITORY ACTIVITY

TECHNICAL FIELD

The present invention relates to novel compounds possessing an antiviral activity, more particularly, bicyclic carbamoylpyridone derivatives having a HIV integrase inhibitory activity and a pharmaceutical composition, particularly an anti-HIV agent.

BACKGROUND TECHNIQUE

Among viruses, human immunodeficiency virus (hereafter, referred to as HIV), a kind of retrovirus, is known to cause acquired immunodeficiency syndrome (hereafter, referred to as AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a combination therapy is reported to be efficient in treatment for AIDS because of the frequent emergence of the resistant mutant. Two kinds of reverse transcriptase inhibitors and protease inhibitors are clinically used as an anti-HIV agent, however agents having the same mechanism of action often exhibit cross-resistance or only an additional activity. Therefore, anti-HIV agents having the other mechanism of action are desired.

Under the circumstances above, an integrase inhibitor has been focused on as an anti-HIV agent having a novel mechanism of action (Ref: Patent Documents 1 and 2). As an anti-HIV agent having such a mechanism of action, known are carbamoyl-substituted hydroxypyrimidinone derivative (Ref: Patent Documents 3 and 4) and carbamoyl-substituted hydroxypyrrolidinone derivative (Ref: Patent Document 5). Further, a patent application concerning carbamoyl-substituted hydroxypyridone derivative has been filed (Ref: Patent Document 6, Example 8).

Other known carbamoylpyridone derivatives include 5-alkoxypyridine-3-carboxamide derivatives and γ-pyrone-3-carboxamide derivatives, which are a plant growth inhibitor or herbicide (Ref: Patent Documents 7-9).

Other HIV integrase inhibitors include N-containing condensed cyclic compounds (Ref: Patent Document 10).

[Patent Document 1] WO03/0166275

[Patent Document 2] WO2004/024693

[Patent Document 3] WO03/035076

[Patent Document 4] WO03/035076

[Patent Document 5] WO2004/004657

[Patent Document 6] JP Patent Application 2003-32772

[Patent Document 7] JP Patent Publication 1990-108668

[Patent Document 8] JP Patent Publication 1990-108683

[Patent Document 9] JP Patent Publication 1990-96506

[Patent Document 10] WO2005/016927

DISCLOSURE OF INVENTION

Problem to be Solved by the Invention

Under such the circumstances, the development of a novel integrase inhibitor has been desired.

Means to Solve the Problems

The present inventors intensively studied to find that a novel bicyclic carbamoylpyridone derivative possesses a potent HIV integrase inhibitory activity. Moreover, the present inventors have discovered that a compound of the present compound and a pharmaceutical composition containing the same are useful as an antiviral agent (e.g. antiretroviral agent, anti-HIV agent, anti-HTLV-1 (Human T cell leukemia virus type 1) agent, anti-FIV (Feline immunodeficiency virus) agent, anti-SIV (Simian immunodeficiency virus) agent), especially an anti-HIV agent, an anti-AIDS agent, or a therapeutic for associated diseases, to accomplish the present invention shown below.

(1) A compound of the formula:

[Chemical formula 1]

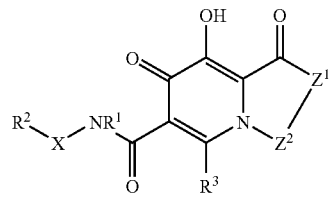

(1)

(wherein, $Z^1$ is $NR^4$ ($R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N═ and ═N—)), O or $CH_2$;

$Z^2$ is optionally substituted lower alkylene or optionally substituted lower alkenylene, each may be intervened by a heteroatom group selected from group consisting O, S, SO, $SO_2$, $NR^5$ ($R^5$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^5$ ($R^5$ is selected independently from the same substituent group as $R^4$), —N= and =N—)), —N= or =N—;

$R^1$ is hydrogen or lower alkyl;

X is a single bond, a heteroatom group selected from O, S, SO, $SO_2$ and NH, or lower alkylene or lower alkenylene each may be intervened by the heteroatom;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino), its pharmaceutically acceptable salt, or solvate thereof.

In the above (1), the case where $Z^1$ is not "optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—)" is also one embodiment of the present invention.

(2) A compound according to the above (1), pharmaceutically acceptable salt, or solvate thereof, wherein $Z^1$ is $NR^4$ ($R^4$ is as defined above (1)).

(3) A compound according to the above (1), pharmaceutically acceptable salt, or solvate thereof, wherein $Z^1$ is $NR^4$ ($R^4$ is hydrogen, optionally substituted lower alkyl, optionally substituted cycloalkyl, optionally substituted cycloalkyl lower alkyl, optionally substituted aryl lower alkyl, or optionally substituted heterocycle lower alkyl).

(4) A compound according to the above (1), pharmaceutically acceptable salt, or solvate thereof, wherein $Z^2$ is optionally substituted lower alkylene or optionally substituted lower alkenylene.

(5) A compound according to the above (1), pharmaceutically acceptable salt, or solvate thereof, wherein $Z^2$ is any one of the following groups:

[Chemical formula 7]

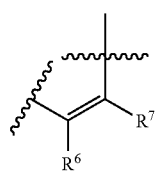
(a)

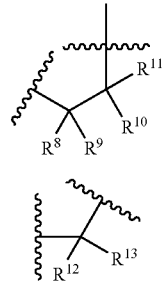
(b)

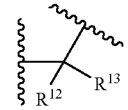
(c)

(wherein $R^6$, $R^7$, $R^8$, $R^9$, $R^{10}$, $R^{11}$, $R^{12}$ and $R^{13}$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocyclic carbonyl, optionally substituted heterocycle lower alkylcarbonyl, optionally substituted heterocycleoxy carbonyl, or optionally substituted aminocarbonyl, or ($R^8$ and $R^9$), ($R^{10}$ and $R^{11}$) or ($R^{12}$ and $R^{13}$) taken together may form "=O", or a combination of ($R^6$ and $R^7$) or ($R^9$ and $R^{10}$) taken together with an adjacent atom may form optionally substituted carbocycle or optionally substituted heterocycle).

(6) A compound according to the above (5), pharmaceutically acceptable salt, or solvate thereof, wherein $R^6$, $R^7$, $R^8$, $R^9$, $R^{10}$, $R^{11}$, $R^{12}$ and $R^{13}$ are each independently hydrogen, lower alkyl, lower alkenyl, lower alkoxy, lower alkenyloxy, hydroxy, or optionally substituted amino.

(7) A compound according to the above (5), pharmaceutically acceptable salt, or solvate thereof, wherein $R^6$, $R^7$, $R^8$, $R^9$, $R^{10}$, $R^{11}$, $R^{12}$ and $R^{13}$ are hydrogen.

(8) A compound according to the above (1), pharmaceutically acceptable salt, or solvate thereof, wherein $R^1$ is hydrogen.

(9) A compound according to the above (1), pharmaceutically acceptable salt, or solvate thereof, wherein X is lower alkylene; $R^2$ is phenyl optionally substituted with at least halogen.

(10) A compound according to the above (1), pharmaceutically acceptable salt, or solvate thereof, wherein $R^3$ is hydrogen, halogen, hydroxy, lower alkyl, lower alkenyl, lower alkoxy, lower alkenyloxy, or optionally substituted amino.

(11) A compound according to the above (1), pharmaceutically acceptable salt, or solvate thereof, wherein $R^3$ is hydrogen.

(12) A compound according to the above (1), pharmaceutically acceptable salt, or solvate thereof, wherein $R^1$ is hydrogen or lower alkyl; X is lower alkylene; $R^2$ is phenyl optionally substituted with at least halogen; $R^3$ is hydrogen, halogen, hydroxy, lower alkyl, lower alkenyl, lower alkoxy, lower alkenyloxy, or optionally substituted amino.

(13) A compound according to the above (1), pharmaceutically acceptable salt, or solvate thereof, wherein $Z^1$ is $NR^4$ ($R^4$ is as defined in above (1)); $Z^2$ is optionally substituted lower alkylene or optionally substituted lower alkenylene; $R^1$ is hydrogen or lower alkyl; X is lower alkylene; $R^2$ is phenyl optionally substituted with at least halogen.

(14) A compound according to the above (1), pharmaceutically acceptable salt, or solvate thereof, wherein $Z^1$ is $NR^4$ ($R^4$ is as defined in above (1)); $Z^2$ is optionally substituted lower alkylene or optionally substituted lower alkenylene; $R^1$ is hydrogen or lower alkyl; X is lower alkylene; $R^2$ is phenyl optionally substituted with at least halogen; $R^3$ is hydrogen, halogen, hydroxy, lower alkyl, lower alkenyl, lower alkoxy, lower alkenyloxy, or optionally substituted amino.

(15) A compound according to the above (1), pharmaceutically acceptable salt, or solvate thereof, wherein $Z^1$ is $NR^4$ ($R^4$ is hydrogen, optionally substituted lower alkyl, optionally substituted cycloalkyl, optionally substituted cycloalkyl lower alkyl, optionally substituted aryl lower alkyl, or optionally substituted heterocycle lower alkyl); $Z^2$ is optionally substituted lower alkylene or optionally substituted lower alkenylene; $R^1$ is hydrogen or lower alkyl; X is lower alkylene; $R^2$ is phenyl optionally substituted with at least halogen; $R^3$ is hydrogen, halogen, hydroxy, lower alkyl, lower alkenyl, lower alkoxy, lower alkenyloxy, or optionally substituted amino.

(16) A compound according to the above (1), pharmaceutically acceptable salt, or solvate thereof, wherein $Z^1$ is $NR^4$ ($R^4$ is as defined in above (1)); $Z^2$ is optionally substituted lower alkylene or optionally substituted lower alkenylene; $R^1$ is hydrogen or lower alkyl; X is lower alkylene; $R^2$ is phenyl optionally substituted with at least halogen; $R^3$ is hydrogen.

(17) A compound according to the above (1), pharmaceutically acceptable salt, or solvate thereof, wherein $Z^1$ is $NR^4$ ($R^4$ is hydrogen, optionally substituted lower alkyl, optionally substituted cycloalkyl, optionally substituted cycloalkyl lower alkyl, optionally substituted aryl lower alkyl, or optionally substituted heterocycle lower alkyl); $Z^2$ is optionally substituted lower alkylene or optionally substituted lower alkenylene; $R^1$ is hydrogen or lower alkyl; X is lower alkylene; $R^2$ is phenyl optionally substituted with at least halogen; $R^3$ is hydrogen.

(18) A compound according to the above (1), pharmaceutically acceptable salt, or solvate thereof, wherein at least any one of the following 1) to 3) is satisfied:

1) the case where $Z^1$ is $NR^4$, and $R^4$ is hydrogen, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—);

2) the case where $Z^2$ is substituted lower alkylene or substituted lower alkenylene, and the substituents are each independently hydroxy, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—);

3) the case where $R^2$ is substituted aryl, and the substituent comprises a group selected at least from Substituent group S1 (: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—), lower alkoxy lower alkyl, optionally substituted amino lower alkyl (substituent: mono- or di-lower alkyl, lower alkylcarbonyl or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, hydroxy lower alkyl).

By satisfying this condition, further improvement in a pharmacological activity and kinetic in a body and the like is expected.

(19) A compound according to the above (1), pharmaceutically acceptable salt, or solvate thereof, wherein $Z^1$ is $NR^4$, $R^4$ is hydrogen, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—).

(20) A compound according to the above (1), pharmaceutically acceptable salt, or solvate thereof, wherein $Z^2$ is substituted lower alkylene or substituted lower alkenylene, and the substituents are each independently hydroxy, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N=and =N—).

(21) A compound according to the above (1), pharmaceutically acceptable salt, or solvate thereof, wherein $R^2$ is substituted aryl, and the substituent comprises a group selected at least from Substituent group S1 (: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—), lower alkoxy lower alkyl, optionally substituted amino lower alkyl (substituent: mono- or di-lower alkyl, lower alkylcarbonyl or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, hydroxy lower alkyl).

(22) A compound according to the above (1) of the formula:

[Chemical formula 8]

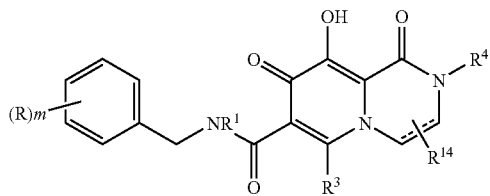

(I-2)

(wherein, $R^1$ is hydrogen or lower alkyl:

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

R's are each independently a group selected from the group consisting of halogen and Substituent group S1;

(Substituent group S1: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—), lower alkoxy lower alkyl, optionally substituted amino lower alkyl (substituent: mono- or di-lower alkyl, lower alkylcarbonyl or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, hydroxy lower alkyl)

m is an integer of 0 to 3;

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting O, S, SO, $SO_2$, $NR^a$ ($R^a$ is hydrogen or lower alkyl), —N= and =N—);

$R^{14}$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocycle carbonyl, optionally substituted heterocyclic lower alkylcarbonyl, optionally substituted heterocycleoxy carbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—); provided that at least one of the following is satisfied:

1) the case where $R^4$ is hydrogen, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—);

2) the case where $R^{14}$ is hydroxy, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—);

3) the case where m is 1 to 3, and at least one R is a group selected from Substituent group S1), pharmaceutically acceptable salt, or solvate thereof.

(23) A compound according to the above (22), wherein $R^1$ is hydrogen; $R^3$ is hydrogen; m is 1 or 2.

(24) A compound according to the above (22), pharmaceutically acceptable salt, or solvate thereof, wherein phosphoric acid residues are each independently represented by the formula:

[Chemical formula 9]

(wherein, $R^A$ and $R^B$ are each independently $OR^C$ or $NR^DR^E$ (wherein $R^C$, $R^D$ and $R^E$ are independently hydrogen, optionally substituted lower alkyl, optionally substituted cycloalkyl, optionally substituted aryl, or optionally substituted hyterocyclic group, or $R^D$ and $R^E$ taken together may form adjacent nitrogen-containing heterocycle), or $R^A$ and $R^B$ taken together may form adjacent phosphorus-containing heterocycle).

(25) A compound according to the above (22), pharmaceutically acceptable salt, or solvate thereof, wherein m is 1 or 2; R's are each independently halogen, halogenated lower alkyl, lower alkoxy, halogenated lower alkoxy, lower alkoxy lower alkyl, hydroxy lower alkyl, amino lower alkyl optionally substituted with mono- or di-lower alkyl, optionally substituted carbamoyl (substituent: mono- or di-lower alkyl, lower alkylcarbonyl, or lower alkylsulfonyl), phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue, or lower alkylsulfonylamino optionally substituted with lower alkyl; $R^1$ is hydrogen; $R^3$ is hydrogen; $R^{14}$ is hydrogen, hydroxy, or amino lower alkyl optionally substituted with mono- or di-lower alkyl; $R^4$ is hydrogen, lower alkyl, lower alkoxy lower alkyl, amino lower alkyl optionally substituted with mono- or di-lower alkyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue.

(26) A compound according to the above (22), pharmaceutically acceptable salt, or solvate thereof, wherein R is —F, —$CF_3$, —OMe, —$OCF_3$, —$CH_2$OMe, —$CH_2$OH, —$CH_2$N(Me)$_2$, —CONHMe, —CON(Me)$_2$, —$CH_2$PO(OEt)$_2$, —PO(OEt)$_2$, —NHSO$_2$Me, or —NMeSO$_2$Me; $R^1$ is hydrogen; $R^3$ is hydrogen; m is 1 or 2; $R^{14}$ is hydrogen, —$CH_2$N(Me)$_2$ or hydroxy; $R^4$ is hydrogen, Me, —(CH$_2$)$_2$OMe, —(CH$_2$)$_2$N(Me)$_2$, —(CH$_2$)$_2$PO(OEt)$_2$.

(27) A compound according to the above (1) of the formula:

[Chemical formula 12]

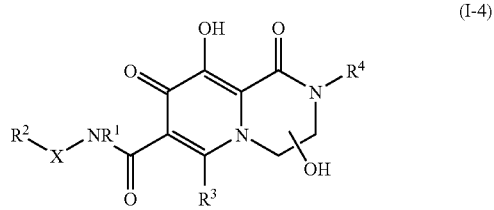

(I-4)

(wherein,
$R^1$ is hydrogen or lower alkyl;
X is a single bond, a heteroatom group selected from O, S, SO, SO$_2$ and NH, or lower alkylene or lower alkenylene each may be intervened by the heteroatom group;
$R^2$ is optionally substituted aryl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;
$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting O, S, SO, SO$_2$, NR$^a$ (R$^a$ is hydrogen or lower alkyl), —N═ and ═N—)), pharmaceutically acceptable salt, or solvate thereof.

(28) A compound according to the above (1) of the formula:

[Chemical formula 13]

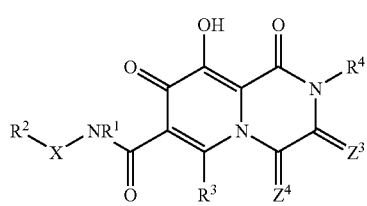

(I-5)

(wherein,
$R^1$ is hydrogen or lower alkyl;
X is a single bond, a heteroatom group selected from O, S, SO, SO$_2$ and NH, or lower alkylene or lower alkenylene each may be intervened by the heteroatom group;
$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

$Z^3$ and $Z^4$ are both oxo, or one of $Z^3$ and $Z^4$ is oxo, and the other is hydrogen or a substituent represented by $R^{14}$;

$R^{14}$ is selected from the group consisting of hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocyclecarbonyl, optionally substituted heterocycle lower alkylcarbonyl, optionally substituted heterocycleoxy carbonyl, and optionally substituted aminocarbonyl;

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting O, S, SO, SO$_2$, NR$^a$ (R$^a$ is hydrogen or lower alkyl), —N═ and ═N—)), pharmaceutically acceptable salt, or solvate thereof.

(29) A compound according to the above (27) or (28), pharmaceutically acceptable salt, or solvate thereof, wherein $R^1$ is hydrogen; X is lower alkylene; $R^2$ is phenyl, or phenyl substituted with at least halogen; and $R^3$ is hydrogen, halogen, hydroxy, lower alkyl, lower alkenyl, lower alkoxy, lower alkenyloxy or optionally substituted amino.

The present invention further provides a pharmaceutical composition containing any of the compounds shown above, a pharmaceutically acceptable salt or a solvate thereof, especially an anti-HIV agent.

Effect of the Invention

The present invention compounds possess an integrase inhibitory activity and/or a cell-growth inhibitory activity against virus, especially HIV. Accordingly, they are useful for the prevention or treatment of various diseases mediated by integrase or virus infection diseases (e.g., AIDS).

PREFERRED EMBODIMENT OF THE INVENTION

The terms used herein are explained below. Each term, alone or in combination with another term, means as follows.

"Lower alkylene" means a straight or branched C1 to C6 lower alkylene such as methylene, ethylene, trimethylene, propylene, tetramethylene, ethylethylene, pentamethylene, or hexamethylene, preferably C1 to C4 lower straight alkylene such as methylene, ethylene, trimethylene, and tetramethylene, more preferably methylene or ethylene.

"Lower alkenylene" means a straight or branched C2 to C6 lower alkenylene, which consists of the above "Lower alkylene" having one or more double bonds, such as vinylene, propylene, or butenylene, preferably a straight C2 to C3 lower alkenylene such as vinylene or propylene.

"Alkyl" means a straight or branched C1 to C10 alkyl such as methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, and n-decyl. Preferred is C1 to C6 lower alkyl, more preferred is C1 to C4 lower alkyl such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

When lower alkyl is intervened with "—N═" or "═N—", the lower alkyl may have a double bond to form —CH$_2$—N═CH$_2$, —CH═N—CH$_3$, etc.

"Alkenyl" means a straight or branched C2 to C8 alkenyl, which consists of the above "alkyl" having one or more double bonds, such as vinyl, 1-propenyl, 2-propenyl, 1-butenyl, 2-butenyl, 3-butenyl, 1,3-butadienyl, and 3-methyl-2-butenyl, preferably C2 to C6 lower alkenyl, and more preferably C2 to C4 lower alkenyl.

"Lower alkenyloxy" means oxy attached to the above "lower alkenyl", such as vinyloxy, 1-propenyloxy, 2-propenyloxy, 1-butenyloxy, 2-butenyloxy, 3-butenyloxy, 1,3-butadienyloxy, and 3-methyl-2-butenyloxy.

"Cycloalkyl" means C3 to C10 cyclic saturated hydrocarbon, such as cyclopropyl, cyclobutyl, cyclopentyl, cyclohexyl, cycloheptyl, and cyclooctyl, preferably C3 to C6 cycloalkyl.

"Cycloalkyl lower alkyl" means lower alkyl substituted with the above cycloalkyl, such as cyclopropylmethyl, cyclopropylethyl, cyclobutylmethyl, cyclopentylmethyl, cyclohexylmethyl, and cyclohexylethyl, and preferably C3 to C6 cycloalkyl lower alkyl.

"Aryl" means monocyclic aromatic hydrocarbon (phenyl) and polycyclic aromatic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.), preferably phenyl or naphthyl (e.g., 1-napthyl, 2-naphthyl).

"Aralkyl" or "aryl lower alkyl" means the above "lower alkyl" substituted with 1 to 3 of the above "aryl", such as benzyl, diphenylmethyl, triphenylmethyl, phenethyl, 1-napthylmethyl, 2-napthylmethyl, preferably benzyl.

"Aryloxy" means oxy attached to the above "aryl", such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, and 9-phenanthryloxy, preferably phenyloxy or naphthyloxy (e.g., 1-napthyloxy, 2-naphthyloxy).

"Heterocyclic group" means "heterocycle" or "heteroaryl".

"Heterocycle" means a non-aromatic heterocyclic group which has at least one of N, O, P and/or S in the ring and may be bonded at any substitutable position, preferably 5- to 7-membered ring, such as 1-pyrrolyl, 2-pyrrolyl, 3-pyrrolyl, 1-pyrrolidinyl, 2-pyrrolidinyl, 3-pyrrolidinyl, 1-imidazolyl, 2-imidazolyl, 4-imidazolyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, and tetrahydropyranyl. The "non-aromatic heterocyclic group" may be saturated or unsaturated as far as it is non-aromatic.

"Heteroaryl" means monocyclic aromatic heterocyclic group or condensed aromatic heterocyclic group.

Monocyclic aromatic heterocyclic group means a group induced from a 5- to 8-membered aromatic ring optionally containing 1 to 4 of O, S, P and/or N in the ring wherein the group may be bonded at any substitutable position.

Condensed aromatic heterocyclic group means a group wherein a 5- to 8-membered aromatic ring optionally containing 1 to 4 of O, S, P and/or N in the ring is condensed with 1 to 4 of 5- to 8-membered aromatic carbocycle (s) or the other 5- to 8-membered aromatic heteroring(s), and may be bonded at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzoimidazolyl (e.g., 1-benzoimidazolyl, 2-benzoimidazolyl, 4-benzoimidazolyl, 5-benzoimidazolyl), dibenzofuryl, benzooxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenandinyl (e.g., 1-phenandinyl, 2-phenandinyl) or phenothiadinyl (e.g., 1-phenothiadinyl, 2-phenothiadinyl, 3-phenothiadinyl, 4-phenothiadinyl).

"Heterocycle lower alkyl" means lower alkyl substituted with the above "heterocyclic group".

"Heterocycle oxy" means an oxy attached to the above "heterocyclic group".

"Heterocycle" means a heterocycle which can form the heterocyclic group.

"Lower alkoxy" means oxy attached to the above "lower alkyl", such as methoxy, ethoxy, n-propoxy, isopropoxy, n-butoxy, isobutoxy, and tert-butoxy.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclecarbonyl", "heterocycle lower alkylcarbonyl", and "heterocycleoxy carbonyl", each means a carbonyl attached to the above "lower alkyl", "cycloalkyl", "cycloalkyl lower alkyl", "lower alkoxy", "aryl", "aryl lower alkyl", "aryloxy", "heterocyclic group", and "heterocycle lower alkyl", respectively.

When a substituent (s) is/are present on "optionally substituted lower alkyl", "optionally substituted cycloalkyl", "optionally substituted cycloalkyl lower alkyl", "optionally substituted lower alkenyl", "optionally substituted lower alkoxy", "optionally substituted aryl", "optionally substituted aryl lower alkyl", "optionally substituted aryloxy", "optionally substituted aryloxy lower alkyl", "optionally substituted heterocyle", "optionally substituted heterocyclic group", "optionally substituted heterocycle lower alkyl", "optionally substituted heterocycleoxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substituted heterocyclecarbonyl", "optionally substituted heterocycle lower alkylcarbonyl", "optionally substituted heterocycleoxy carbonyl", "optionally substituted lower alkylene", "optionally substituted lower alkenylene", "optionally substituted phosphoric acid residue", "optionally substituted carbocycle" or "optionally substituted heterocycle", each may be substituted with the same or different, 1 to 4 group (s) selected from Substituent group B at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetylamino, benzoylamino), aralkylamino (e.g., benzylamino, trithylamino), hydroxyamino), azido, aryl (e.g., phenyl), aralkyl (e.g., benzyl), cyano, isocyano, isocyanate, thiocyanate, isothiocyanate, mercapto, alkylthio (e.g., methylthio), alkylsulfonyl (e.g., methanesulfonyl, ethanesulfonyl), optionally substituted alkylsulfonylamino (e.g., methanesulfonylamino, ethanesulfonylamino, N-methylsulfonyl-N'-methylamino), optionally substituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxal, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, lower alkyl which is substituted with a phosphoric acid residue and may be intervened with a heteroatom group (s), aryl substituted with a phosphoric acid residue, aralkyl substituted with a phosphoric acid residue, and hydroxy lower alkyl, more preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), optionally substituted amino (e.g., alkylamino (e.g., methylamino, ethylamino, dimethylamino), oxo, or phosphoric acid residue.

Examples of a substituent of "optionally substituted amino" or "optionally substituted carbamoyl" include mono- or di-lower alkyl, lower alkylcarbonyl or lower alkylsulfonyl, optionally substituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxy lower alkyl, heterocycle lower alkyl (e.g., morpholinoethyl, tetrahydropyranylethyl), alkoxycarbonyl lower alkyl (e.g., ethoxycarbonylmethyl, ethoxycarbonylethyl), mono- or di-lower alkylamino lower alkyl (e.g., dimethylaminoethyl)), lower alkoxy lower alkyl (e.g., methoxyethyl, ethoxymethyl, ethoxyethyl, isopropoxyethyl), acyl (e.g., formyl, optionally substituted lower alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally substituted with lower alkyl or halogen (e.g., benzenesulfonyl, toluenesulfonyl, 4-fluorobenzenesulfonyl), cycloalkyl (e.g., cyclopropyl), aryl optionally substituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino), and the like.

As to amino of "optionally substituted amino", "optionally substituted carbamoyl", or "optionally substituted carbamoylcarbonyl", two substituents on the amino together with the neighboring N atom may form an N-containing heterocycle which optionally contains S and/or O in the ring (preferably 5- to 7-membered ring or saturated ring) and the ring is optionally substituted with oxo or hydroxy. The optional S atom in the ring may be substituted with oxo. A 5- or 6-membered ring such as piperazinyl, piperidino, morpholino, pyrrolidino, thiadinan-2-yl, 2-oxopiperidino, 2-oxopyrrolidino, 1,1-dioxido-1,2-thiadinan-2-yl, and 4-hydroxymorpholino.

Phosphoric acid residue means a group shown of the formula: —PO(OH)$_2$. Optionally substituted phosphoric acid residue means a phosphoric acid residue wherein the OH part and/or hydrogen of the OH is optionally substituted with a phosphoric acid residue, preferably shown by the formula:

[Chemical formula 20]

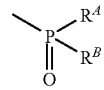

(P-1)

(wherein, $R^A$ and $R^B$ each are independently $OR^C$ or $NR^DR^E$ (wherein $R^C$, $R^D$ and $R^E$ each are independently hydrogen, optionally substituted lower alkyl, optionally substituted cycloalkyl, optionally substituted aryl, optionally substituted heterocyclic group, or $R^D$ and $R^E$ taken together with the neighboring N atom may form an optionally substituted heterocycle (preferably 5- to 6-membered ring)), or $R^A$ and $R^B$ taken together with the neighboring P atom may form an optionally substituted heterocycle (preferably 5- to 6-membered ring)).

More preferably, $R^A$ and $R^B$ are both $OR^C$, or one of them is $OR^C$ and the other is $NR^DR^E$.

$R^C$, $R^D$ and $R^E$ each are preferably, independently, lower alkyl (e.g., methyl, ethyl).

The optionally substituted heterocycle formed by $R^A$ and $R^B$ taken together with the neighboring P atom may be the following structure:

[Chemical formula 21]

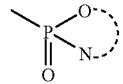

(wherein, the broken line means a part of the ring)

Hydroxy substituted with optionally substituted phosphoric acid residue is preferably hydroxy substituted with a phosphoric acid residue substituted with di lower alkyls, and more preferably a group of the formula:

[Chemical formula 22]

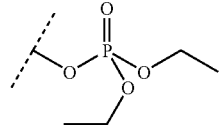

Amino substituted with optionally substituted phosphoric acid residue is preferably amino substituted with a phosphoric acid residue substituted with di lower alkyls, and more preferably a group of the formula:

[Chemical formula 23]

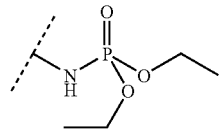

MORE PREFERABLE EMBODIMENTS $Z^1$ is $NR^4$ ($R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$. $NR^5$ ($R^5$ is selected independently from the same substituent group of $R^4$), —N═and ═N—)), O or $CH_2$.

A substituent related to "optionally" in $R^4$ is preferably selected from hydroxy, lower alkyl, lower alkoxy, optionally substituted amino (example of substituent: mono- or di-lower alkyl, lower alkylcarbonyl, lower alkylsulfonyl, optionally substituted phenyl), halogen, halogenated alkyl, halogenated lower alkoxy, heterocyclic group, alkylsilyl, cyano, phenyl and the like.

$Z^1$ is preferably $NR^4$.

$R^4$ is preferably hydrogen, lower alkyl (e.g.: methyl, ethyl, n-propyl, isopropyl, 2-ethylpropyl), optionally substituted lower alkoxy, optionally substituted lower alkoxy lower alkyl (e.g.: 2-isopropoxyethyl, 2-methoxyethyl, 2-ethoxyethyl, 3-methoxy-n-propyl, 2-n-propoxyethyl; example of substituent: phenyl), hydroxy lower alkyl (e.g.: 2-hydroxyethyl), mono- or di-lower alkylamino lower alkyl (2-methylaminoethyl, 2-dimethylaminoethyl, N-acetylaminoethyl), substituted amino lower alkyl (example of substituent: lower alkyl, optionally substituted phenyl (example of substituent: lower alkyl), optionally substituted heterocycle), optionally substituted cycloalkyl (e.g. cyclohexyl), optionally substituted cycloalkyl lower alkyl (e.g. cyclohexylmethyl, 2-cyclohexylethyl), optionally substituted aryl (e.g. phenyl, example of substituent: halogen, lower alkoxy, halogenated lower alkyl), optionally substituted aryl lower alkyl (e.g. benzyl, 4-halogenobenzyl, 4-dimethylaminobenzyl), optionally substituted aryloxy lower alkyl, optionally substituted heterocycle lower alkyl (e.g. morpholino lower alkyl, pyridyl lower alkyl, furyl lower alkyl, thienyl lower alkyl), optionally substituted phosphoric acid residue, or lower alkyl substituted with optionally substituted phosphoric acid residue (the lower alkyl may be intervened by a heteroatom group selected from group consisting O, S, SO, $SO_2$. $NR^5$ ($R^5$ is selected independently from the same substituent group of $R^4$), —N═and ═N—). The heterocyclic group in the optionally substituted heterocycle lower alkyl is preferably a 5- to 7-membered aliphatic heterocyclic group (e.g. piperidyl, morpholino, piperazinyl, pyrrolidinyl, tetrahydrofuryl).

$R^4$ is more preferably hydrogen, lower alkyl (e.g. methyl, ethyl), lower alkoxy lower alkyl (e.g. 2-methoxyethyl, —$(CH_2)_n$O-i-Pr (n=integer of 1 to 4)), hydroxy lower alkyl (e.g. —$(CH_2)_2$OH), optionally substituted amino lower alkyl (example of substituent: mono- or di-lower alkyl, lower alkylcarbonyl or lower alkylsulfonyl; e.g. 2-dimethylaminoethyl), carbamoyl lower alkyl optionally substituted with mono- or di-lower alkyl (e.g. $CH_2CONMe_2$), optionally substituted phosphoric acid residue (example of substituent: lower alkyl; e.g. —$PO(OEt)_2$), lower alkyl substituted with optionally substituted phosphoric acid residue (example of substituent: lower alkyl; e.g. —$(CH_2)_2$—$PO(OEt)_2$), aryl substituted with optionally substituted phosphoric acid residue (example of aryl: phenyl), aralkyl substituted with optionally substituted phosphoric acid residue (example of aralkyl: benzyl), lower alkyl substituted with optionally substituted phosphoric acid residue, or optionally substituted aryl lower alkyl.

One of preferable embodiments of $R^4$ is lower alkyl (e.g. methyl), lower alkoxy lower alkyl (e.g. 2-methoxyethyl), or halogenated aralkyl (e.g. 4-halogenobenzyl).

$Z^2$ is optionally substituted lower alkylene or optionally substituted lower alkenylene, each may be intervened by a heteroatom group selected from group consisting O, S, SO, $SO_2$, $NR^5$ ($R^5$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino), —N═and ═N—. Herein, "intervene" means the case where the heteroatom 1) is present between carbon atoms constituting lower alkylene or lower alkenylene, 2) is bound to a N, O or C atom of $Z^1$ adjacent to $Z^2$, and/or 3) is bound to an N atom in a pyridine ring, and 1) is preferable. The heteroatom group (M) may be same or different one or more groups. For example, the case where lower alkylene is intervened by the heteroatom includes -M-$CH_2$—, —$CH_2$-M-$CH_2$—, —$CH_2$-M-, and —$CH_2$-M-M-$CH_2$—, preferably —$CH_2$-M-$CH_2$—.

$Z^2$ is preferably a spacer in which 1 to 3 atoms are connected. $Z^2$ is more preferably optionally substituted lower alkylene or optionally substituted lower alkenylene. $Z^2$ is further preferably any of the following groups, particularly preferably a group of (b).

[Chemical formula 24]

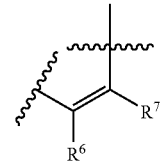

(a)

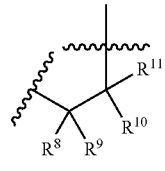

(b)

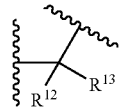

(c)

(wherein $R^6$, $R^7$, $R^8$, $R^9$, $R^{10}$, $R^{11}$, $R^{12}$ and $R^{13}$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted aryloxy lower alkyl, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocyclic carbonyl, optionally substituted heterocycle lower alkylcarbonyl, optionally substituted heterocycleoxy carbonyl, or optionally substituted aminocarbonyl, or ($R^8$ and $R^9$), ($R^{10}$ and $R^{11}$) or ($R^{12}$ and $R^{13}$) taken together may form "=O", or a combination of ($R^6$ and $R^7$) or ($R^9$ and $R^{10}$) taken together with an adjacent atom may form optionally substituted carbocycle (e.g. cycloalkyl, aryl) or they may be optionally substituted heterocycle (e.g. heteroaryl, heterocycle), or optionally substituted phosphoric acid residue, aryl substituted with optionally substituted phosphoric acid residue, aralkyl substituted with optionally substituted phosphoric acid residue, or lower alkyl substituted with optionally substituted phosphoric acid residue (the lower alkyl may be intervened by a heteroatom group selected from group consisting O, S, SO, $SO_2$, $NR^a$ ($R^a$ is hydrogen or lower alkyl), —N= and =N—)).

In addition, $R^6$, $R^7$, $R^8$, $R^9$, $R^{10}$, $R^{11}$, $R^{12}$ and $R^{13}$ may be a group exemplified as $R^{14}$ described later.

A substituent of "optionally substituted" in $R^6$, $R^7$, $R^8$, $R^9$, $R^{10}$, $R^{11}$, $R^{12}$ and $R^{13}$ is preferably selected from hydroxy, lower alkyl, lower alkoxy, amino, mono- or di-lower alkylamino, N-lower alkylcarbonylamino, N-methanesulfonylamino, halogen, halogenated lower alkyl, halogenated lower alkoxy, heterocyclic group and the like.

$R^6$, $R^7$, $R^8$, $R^9$, $R^{10}$, $R^{11}$, $R^{12}$ and $R^{13}$ are preferably each independently hydrogen, optionally substituted lower alkyl (e.g. methyl, ethyl, n-propyl, isopropyl, 2-methoxyethyl, 2-hydroxyethyl, 2-isopropoxyethyl, 2-ethoxyethyl, 3-methyl-n-propyl, hydroxymethyl, methoxymethyl, isopropoxymethyl, N,N-dimethylaminomethyl, N-acetylaminomethyl, N-methyl-N-acetylaminomethyl, N-methanesulfonylaminomethyl), lower alkenyl, lower alkoxy (e.g. methoxy), lower alkenyloxy, hydroxy, or optionally substituted amino (e.g. amino, dimethylamino), aryl lower alkyl (e.g. benzyl), aryloxy lower alkyl (e.g. benzyloxymethyl).

In another preferable embodiment, at least one of ($R^8$, $R^9$), ($R^{10}$, $R^{11}$) and ($R^{12}$, $R^{13}$) is hydrogen.

In another preferable embodiment, $R^6$, $R^7$, $R^8$, $R^9$, $R^{10}$, $R^{11}$, $R^{12}$ and $R^{13}$ are all hydrogen.

In another preferable embodiment, ($R^8$, $R^9$), ($R^{10}$, $R^{11}$) or ($R^{12}$, $R^{13}$) taken together form "=O". Particularly preferably, ($R^8$ and $R^9$) and/or ($R^{10}$ and $R^{11}$) taken together form "=O" and, in this case, Compound (I-5) is exemplified.

In another preferable embodiment, one of $R^6$ and $R^7$ is hydroxy, or amino lower alkyl optionally substituted with mono- or di-lower alkyl (e.g. —$CH_2N(M_e)_2$), and the other is hydrogen.

In another preferable embodiment, at least one of $R^8$, $R^9$, $R^{10}$ and $R^{11}$ is hydroxy, or amino lower alkyl optionally substituted with mono- or di-lower alkyl (e.g. —$CH_2N(M_e)_2$), and the remaining is hydrogen. In one of more preferably embodiments, any one of $R^8$, $R^9$, $R^{10}$ and $R^{11}$ is hydroxy, the remaining is hydrogen, and Compound (I-4) is exemplified.

In another preferable embodiment, one of $R^{12}$ and $R^{13}$ is hydroxy, and the other is hydrogen.

In another preferable embodiment, one of $R^8$ and $R^9$ is hydroxy, and the other is hydrogen, lower alkyl (e.g. methyl, isopropyl), or lower alkoxy lower alkyl (e.g. 2-methoxyethyl).

$R^1$ is hydrogen or lower alkyl, preferable hydrogen.

X is a single bond, a heteroatom group (hereinafter, referred to as M in some cases) selected from O, S, SO, $SO_2$ and NH, or lower alkylene or lower alkenylene, each may be intervened by the heteroatom. Herein, "intervene" means the case where the heteroatom 1) is present between carbon atoms constituting lower alkylene or lower alkenylene, 2) is bound to a N atom of carbamoyl group adjacent to X, and/or 3) is bound to $R^2$ adjacent to X. The heteroatom group (M) may be same or different one or more groups. For example, the case where lower alkylene is intervened by the heteroatom includes -M-$CH_2$—, —$CH_2$-M-$CH_2$—, —$CH_2$-M-, and —$CH_2$-M-M-$CH_2$—. X is preferably a spacer in which 1 to 3 atoms are connected. X is more preferably lower alkylene, or lower alkenylene which may be intervened by a heteroatom, or O, further preferably C1 to C3 lower alkylene to C2 to C3 lower alkenylene, or O, particularly preferably methylene or O.

$R^2$ is optionally substituted aryl, preferably phenyl. Examples of a substituent on aryl preferably include same or different 1 to 3, preferably 1 to 2 substituents selected from the group consisting of halogen, hydroxy, amino, lower alkylamino, cyano, carboxy, formyl, oxo, lower alkyl, lower alkoxy, lower alkylthio, carbamoyl, and lower alkylcarbamoyl, and Substituent group S1 (: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting O, S, SO, $SO_2$. $NR^5$ ($R^5$ is selected independently from the same substituent group of $R^4$), —N= and =N—), lower alkoxy lower alkyl, amino lower alkyl optionally substituted with mono- or di-lower alkyl, halogenated lower alkyl, lower alkoxy, carbamoyl optionally substituted with mono- or di-lower alkyl, optionally substituted lower alkylsulfonylamino, halogenated lower alkoxy, hydroxy lower alkyl). The substituent is a group more preferably selected from halogen, hydroxy, amino, cyano, lower alkyl, and lower alkoxy, and Substituent group S1, particularly preferably selected from halogen (e.g. F) and/or Substituent group S1. When one substituent is present on aryl, its position is preferably a 4-position. $R^2$ is more preferably phenyl, or phenyl substituted with at least halogen, particularly preferably 4-halogenophenyl (e.g. 4-F-phenyl).

$R^2$ is more preferably phenyl optionally substituted with 1 to 3 substituents described later.

In all compounds of the present invention, a —X—$R^2$ part is preferably represented by the following formula.

[Chemical formula 27]

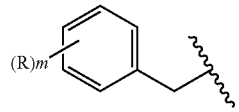

R's are each independently a group selected from the group consisting of halogen and Substituent group S1.

Substituent group S1: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—), lower alkoxy lower alkyl, optionally substituted amino lower alkyl (substituent: mono- or di-lower alkyl, lower alkylcarbonyl, or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, and hydroxy lower alkyl.

And, m is an integer of 0 to 3, preferably o, or 1 to 2. When m is 1, R is preferably halogen and, when m is 2, R is preferably halogen, or other group.

R is preferably present at a 4-position and, optionally, other position on a benzene ring.

When m=2, R is more preferably same or different groups selected from the group consisting of halogen, lower alkyl, lower alkoxy, lower alkoxy lower alkyl, halogenated alkyl, halogenated lower alkoxy, lower alkylsulfonylamino, carbamoyl, and lower alkylcarbamoyl.

$R^3$ may be a variety of substituents as far as they do not adversely affect on the pharmacological activity of Compound (I), and examples include hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino. Examples of a substituent of "optionally substituted" include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, and halogenated lower alkoxy, more preferably halogen, hydroxy, amino, lower alkylamino, lower alkyl, and lower alkoxy. $R^3$ is more preferably hydrogen, halogen, hydroxy, lower alkyl, lower alkenyl, lower alkoxy, lower alkenyloxy or optionally substituted amino, further preferably hydrogen or lower alkyl (e.g. methyl), particularly preferably hydrogen.

Preferable aspects of the present compound are exemplified below.

(1) The case where $R^1$ is hydrogen or lower alkyl; X is lower alkylene; $R^2$ is phenyl, or phenyl substituted with at least halogen; $R^3$ is hydrogen, halogen, hydroxy, lower alkyl, lower alkenyl, lower alkoxy, lower alkenyloxy or optionally substituted amino, preferably hydrogen.

(2) The case where $Z^1$ is $NR^4$ ($R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, or optionally substituted amino); $Z^2$ is optionally substituted lower alkylene or optionally substituted lower alkenylene; $R^1$ is hydrogen or lower alkyl; X is lower alkylene; $R^2$ is phenyl, or phenyl substituted with at least halogen.

(3) The case where $Z^1$ is $NR^4$ ($R^4$ is as defined in (2)); $Z^2$ is optionally substituted lower alkylene or optionally substituted lower alkenylene; $R^1$ is hydrogen or lower alkyl; X is lower alkylene; $R^2$ is phenyl, or phenyl substituted with at least halogen; $R^3$ is hydrogen, halogen, hydroxy, lower alkyl, lower alkenyl, lower alkoxy, lower alkenyloxy or optionally substituted amino, preferably hydrogen.

(4) The case where $Z^1$ is $NR^4$ ($R^4$ is hydrogen, optionally substituted lower alkyl, optionally substituted cycloalkyl, optionally substituted cycloalkyl lower alkyl, optionally substituted aryl lower alkyl, or optionally substituted heterocycle lower alkyl); $Z^2$ is optionally substituted lower alkylene or optionally substituted lower alkenylene; $R^1$ is hydrogen or lower alkyl; X is lower alkylene; $R^2$ is phenyl, or phenyl substituted with at least halogen; $R^3$ is hydrogen, halogen, hydroxy, lower alkyl, lower alkenyl, lower alkoxy, lower alkenyloxy or optionally substituted amino, preferably hydrogen.

(5) The case where $Z^1$ is $NR^4$ ($R^4$ is as defined in (2)); $Z^2$ is optionally substituted lower alkylene or optionally substituted lower alkenylene; $R^1$ is hydrogen or lower alkyl; X is lower alkylene; $R^2$ is phenyl, or phenyl substituted with at least halogen; $R^3$ is hydrogen.

(6) The case where $Z^1$ is $NR^4$ ($R^4$ is hydrogen, optionally substituted lower alkyl, optionally substituted cycloalkyl, optionally substituted cycloalkyl lower alkyl, optionally substituted aryl lower alkyl, or optionally substituted heterocycle lower alkyl); $Z^2$ is optionally substituted lower alkylene or optionally substituted lower alkenylene; $R^1$ is hydrogen or lower alkyl; X is lower alkylene; $R^2$ is phenyl, or phenyl substituted with at least halogen; $R^3$ is hydrogen.

(7) The case where a $Z^2$ part is substituted with hydroxy or oxo (e.g. Compounds (I-4) and (I-5)).

Another preferable embodiment of Compound (I) includes the following compounds.

[Chemical formula 35]

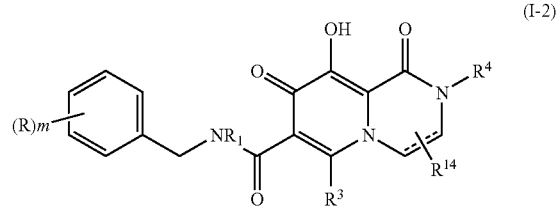

(I-2)

$R^1$ is hydrogen or lower alkyl, preferably hydrogen.

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino, preferably halogen, hydroxy, lower alkyl, or lower alkenyl, more preferably hydrogen.

R's are a group independently selected from the group consisting of halogen and Substituent group S1.

Substituent group S1: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—), lower alkoxy lower alkyl, optionally substituted amino lower alkyl (substituent: mono- or di-lower alkyl, lower alkylcarbonyl, or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, and hydroxy lower alkyl.

Herein, m is an integer of 0 to 3, preferably 0, or 1 to 2. Preferably, m is 1 to 3, and at least one R is a group selected from Substituent group S1.

When m is 1, R is preferably halogen and, when m is 2, R is preferably a group selected from halogen and Substituent group S1.

R is preferably present at a 4-position and, optionally, other position on a benzene ring.

"Optionally substituted phosphoric acid residue" is preferably represented by the formula: (P-1).

$R^4$ is as defined above, and is preferably hydrogen, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N= and =N—).

$R^{14}$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocycle carbonyl, optionally substituted heterocyclic lower alkylcarbonyl, optionally substituted heterocycleoxy carbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N=and =N—); preferably hydrogen, hydroxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue, or optionally substituted amino lower alkyl (substituent: mono- or di-lower alkyl, lower alkylcarbonyl or lower alkylsulfonyl), more preferably hydrogen or OH. Preferably, it is hydroxy, optionally substituted amino lower alkyl (substituent: mono- or di-lower alkyl, lower alkylcarbonyl or lower alkylsulfonyl), optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting CO, O, S, SO, $SO_2$, $NR^a$ ($R^a$ is hydrogen or lower alkyl), —N=and =N—).

Compound (I-2) is preferably the following embodiment.

(1) Herein, m is 1 or 2; R's are each independently halogen, halogenated lower alkyl, lower alkoxy, halogenated lower alkoxy, lower alkoxy lower alkyl, hydroxy lower alkyl, optionally substituted amino lower alkyl or optionally substituted carbamoyl (substituent: mono- or di-lower alkyl, lower alkylcarbonyl or lower alkylsulfonyl), phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue, or lower alkylsulfonylamino in which NH part is optionally substituted with lower alkyl, preferably at least one halogen; $R^1$ is hydrogen; $R^3$ is hydrogen; $R^{14}$ is hydrogen, hydroxy, or amino lower alkyl optionally substituted with mono- or di-lower alkyl; $R^4$ is hydrogen, lower alkyl, lower alkoxy lower alkyl, amino lower alkyl optionally substituted with mono- or di-lower alkyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue; phosphoric acid residue is preferably represented by the (P-1);

provided that the case where R is halogen; $R^{14}$ is hydrogen; and $R^4$ is lower alkyl or lower alkoxy lower alkyl is excluded.

(2) Herein, m is 1 or 2, R's are each independently —F, —$CF_3$, —OMe, —$OCF_3$, —$CH_2$OMe, —$CH_2$OH, —$CH_2$N$(Me)_2$, —CONHMe, —CON$(Me)_2$, —$CH_2$PO$(OEt)_2$, —PO$(OEt)_2$, —NHSO$_2$Me, or —NMeSO$_2$Me, or one of R's is —F, and a remaining is other group; $R^1$ is hydrogen; $R^3$ is hydrogen; $R^{14}$ is hydrogen, amino lower alkyl optionally substituted with mono- or di-lower alkyl (e.g. —$CH_2$N$(Me)_2$) or hydroxy; $R^4$ is hydrogen, lower alkyl (e.g. Me), lower alkoxy lower alkyl (e.g. —$(CH_2)_2$OMe), amino lower alkyl optionally substituted with mono- or di-lower alkyl (e.g. —$CH_2$N$(Me)_2$), phosphoric acid residue optionally substituted with lower alkyl (e.g. —$(CH_2)_2$PO$(OEt)_2$);

provided that the case where R is —F; $R^{14}$ is hydrogen; and $R^4$ is Me or —$(CH_2)_2$OMe is excluded.

A broken line indicates the presence or absence of a bond.

Another embodiment of Compound (I) further includes the following compounds (I-4), and (I-5).

[Chemical formula 38]

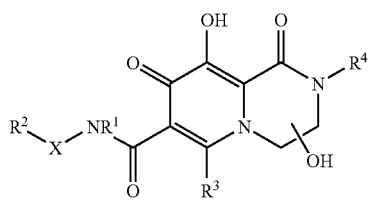

(I-4)

(wherein each symbol is as defined above)

A preferable embodiment is according to a compound (I-2).

[Chemical formula 39]

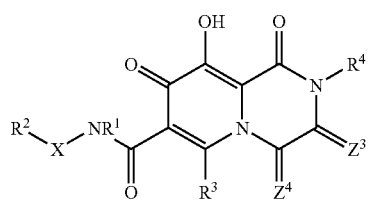

(I-5)

(wherein each symbol is as defined above)

In one preferable embodiment of $Z^3$ and $Z^4$, any one of them indicates oxo, and the other indicates two hydrogen. A preferable embodiment of other substituents is according to a compound (I-2).

Compound (I) has at least the following characteristics as its chemical structure.

(1) The main structure, condensed heterocycle, is substituted with oxo (=O), hydroxy (OH) and oxo (=O).

(2) A substituted carbamoyl group (—CONR$^1$XR$^2$) is attached to the position neighboring to the oxo group on the heterocycle.

The above structure contributes to a remarkably potent integrase inhibitory activity and/or cell-growth inhibitory activity against virus including HIV. In contrast, the structures of the other parts ($Z^1$, $Z^2$, and $R^3$) have a relatively large freedom degree, may have a variety of substituents, and may form a condensed ring, and the condensed ring may be further substituted.

The present invention provides a pharmaceutically acceptable salt or a solvate of Compound (I). All theoretically possible tautomer, geometrical isomer, optically active compound, and racemate thereof are within the scope of the invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine, meglumine, diethanolamine, or ethylenediamine salts; aralkyl amine salts such as N, N-dibenzylethylenediamine or benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararates, malates, citrates salts, or ascorbates; sulfonates such as methanesulfonates, isethionates, benzenesulfonates, or p-toluenesulfonates; and acidic amino acid salts such as aspartates or glutamates.

Solvates of a compound of the present invention include alcholates and hydrates.

A general process for producing the present compound will be exemplified below.

(Method of Preparing Raw Material)

[Chemical formula 41]

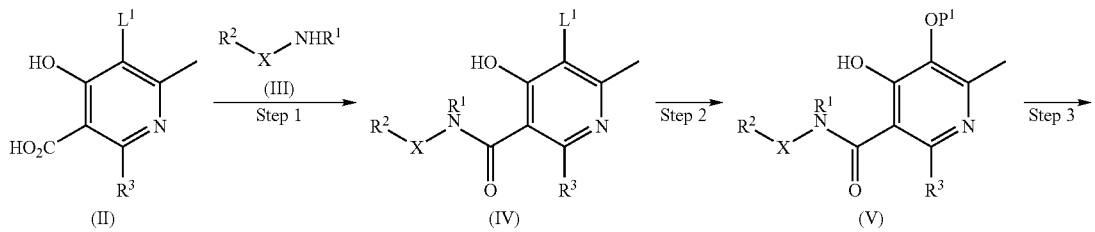

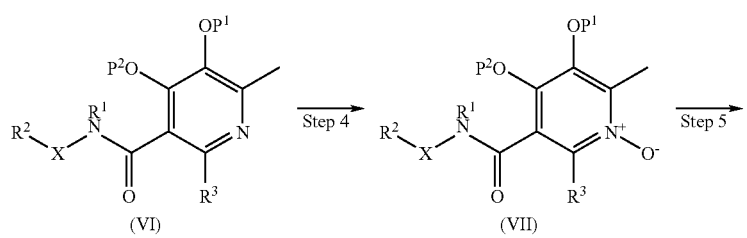

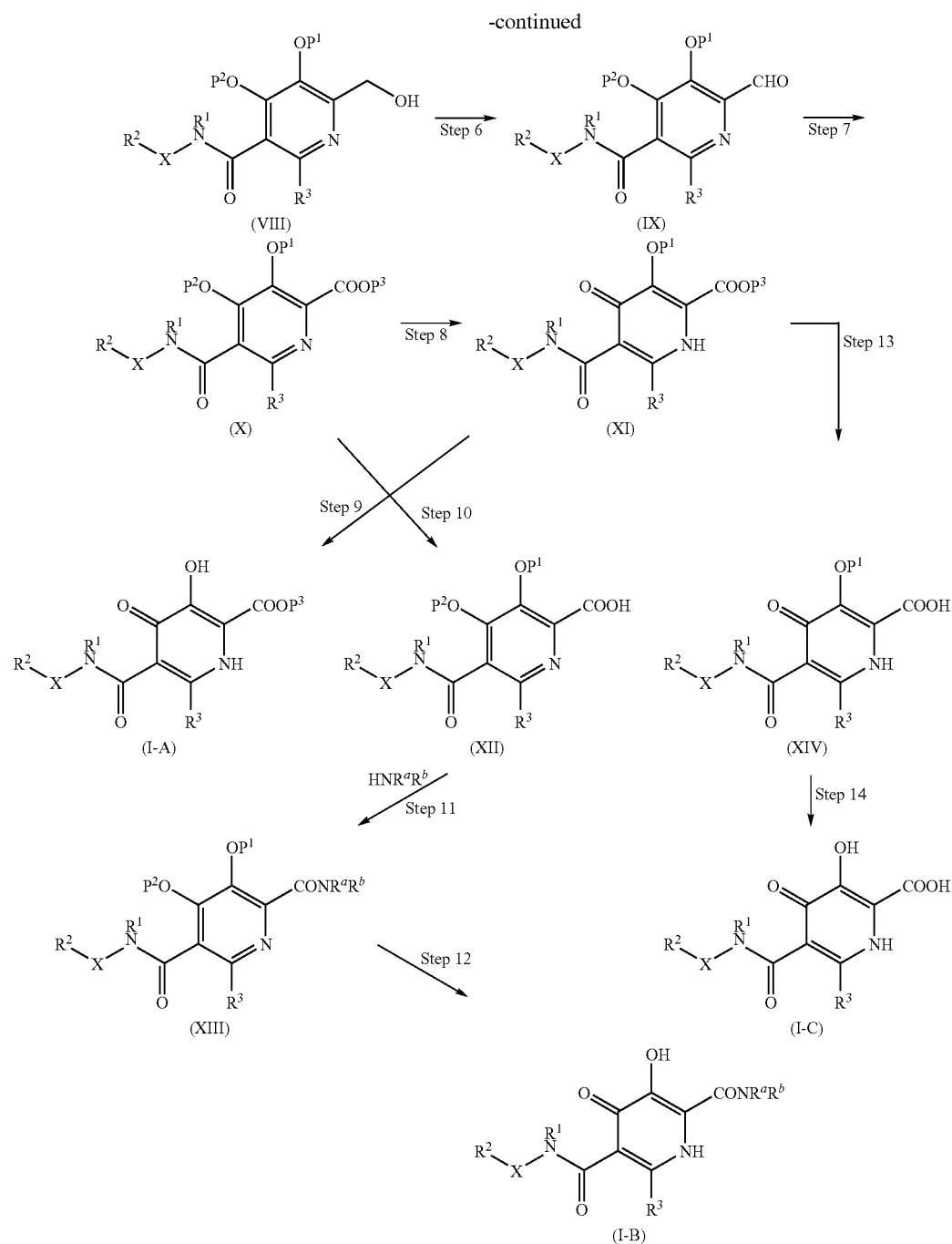

(wherein $L^1$ is a leaving group (e.g.; halogen); $P^1$ and $P^2$ are a hydroxy protecting group; $P^3$ is a carboxy protecting group (e.g.: lower alkyl); $R^a$ and $R^b$ are hydrogen or a substituent on an amino group)

Examples of a hydroxy protecting group ($P^1$, $P^2$) include acyl (e.g.: acetyl, pivaloyl, benzoyl), aralkyl (e.g.: benzyl), lower alkyl (e.g.: methyl), alkoxyalkyl (e.g.: methoxymethyl, methoxyethyl), lower alkylsulfonyl (e.g.: methanesulfonyl), arylsulfonyl (e.g.: benzenesulfonyl, toluenesulfonyl), alkoxycarbonyl (e.g.: methoxycarbonyl) and the like.

As a carboxy protecting group ($P^3$), lower alkyl (e.g.; methyl, ethyl), and aralkyl (e.g.: benzyl) are exemplified.

(First Step)

The present step is a reaction for condensing a compound (II) and a compound (III) to synthesize a compound (IV). The reaction may be performed according to the condition for a reaction of amidating carboxylic acid which is generally performed. A compound (II) may be reacted as it is, or may be reacted after converted into corresponding acid chloride or active ester. Preferably, the reaction is performed in a suitable solvent in the presence of a condensing agent.

As a condensing agent, dicyclohexylcarbodiimide, 1-ethyl-3-(3-dimethylaminopropyl)carbodiimide hydrochloride and the like may be used. If necessary, a reagent such as 1-hydroxybenzotriazole and N-hydroxysuccinimide, or a base such as triethylamine, N-methylmorpholine, and pyridine may be added.

A reaction temperature is 0 to 150° C., preferably room temperature to 70° C.

As a reaction solvent, an aprotic solvent can be broadly used, and tetrahydrofuran (THF), 1,4-dioxane, dimethylformamide (DMF), methylene chloride, chloroform and the like are preferable.

A reaction time is a few minutes to a few tens hours, preferably 9 to 17 hours.

(Second Step)

The present step is a reaction for introducing a protected hydroxy group ($OP^1$) into a compound (IV) to produce a compound (V). The reaction may be performed according to the condition for an alkoxylating reaction which is generally performed.

For example, a compound (V) in which $P^1$ is methyl can be synthesized by reacting a compound (IV) with metal alkoxide (e.g.: sodium methoxide).

A reaction temperature is 0 to 200° C., preferably 80 to 120° C.

As a reaction solvent, alcohol, dimethylformamide (DMF), and dimethyl sulfoxide (DMSO) are exemplified.

A reaction time is a few minutes to a few tens hours, preferably 5 to 10 hours.

(Third Step)

The present step is a reaction for protecting a hydroxy group of a compound (V) to produce a compound (VI). The reaction may be performed according to the condition for a reaction of protecting a hydroxy group which is generally performed. For example, by using diisopropyl azodicarboxylate or diethyl azodicarboxylate together with an alcohol and various phosphines, a compound (VI) in which $P^2$ is alkyl can be synthesized.

A reaction temperature is 0 to 100° C., preferably 0° C. to room temperature.

As a reaction solvent, THF, toluene, dichloromethane and the like are exemplified.

A reaction time is a few minutes to a few tens hours, preferably 1 to 3 hours.

(Fourth Step)

The present step is a reaction of oxidizing a nitrogen atom of a compound (VI) to produce a compound (VII). The reaction may be performed according to the condition for an oxidation reaction using an oxidizing agent which is generally performed.

A reaction temperature is 0 to 100° C., preferably under ice-cooling to room temperature.

As a reaction solvent, chloroform, methylene chloride, acetic acid and the like are exemplified.

Examples of an oxidizing agent include metachloroperbenzoic acid, hydrogen peroxide and the like.

A reaction time is a few minutes to a few tens hours, preferably 1 to 5 hours.

(Fifth Step)

The present step is a reaction for hydroxylating a methyl group of a compound (VII). Preferably, after acetoxylation by a reaction with acetic anhydride (reaction temperature: 0 to 150° C., preferably 120 to 140° C.), this may be hydrolyzed (e.g.: treatment with a base (e.g.: alkali metal hydroxide)).

A reaction time is a few minutes to a few tens hours, preferably 0.5 to 2 hours for acetoxylation, and 0.5 to 1 hour for hydrolysis.

(Sixth Step)

The present step is a reaction for oxidizing a hydroxy group of a compound (VIII) to synthesize a compound (IX).

A reaction temperature is 0 to 150° C., preferably room temperature to 70° C.

As a reaction solvent, chloroform and the like are exemplified.

As an oxidizing agent, dimethyl sulfoxide and the like are exemplified.

A reaction time is a few minutes to a few tens hours, preferably 0.1 to 1 hour.

(Seventh Step)

The present step is a reaction for oxidizing a formyl group of a compound (IX) to synthesize a compound (X).

A reaction temperature is 0 to 150° C., preferably under ice-cooling to room temperature.

As a reaction solvent, an alcohol and the like are exemplified.

As an oxidizing agent, potassium hydroxide and iodine are exemplified.

A reaction time is a few minutes to a few tens hours, preferably 0.5 to 3 hours.

(Eighth Step)

The present step is a reaction for deprotecting an $OP^2$ part of a compound (X) to synthesize a compound (XI). The reaction may be performed according to the condition for a reaction of deprotecting a hydroxy protecting group which is generally performed.

A reaction temperature is 0 to 150° C., preferably under ice-cooling to room temperature.

As a reaction solvent, acetonitrile, methylene chloride, THF and the like are exemplified.

A reaction time is a few minutes to a few tens hours, preferably 1 to 3 hours.

(Ninth Step)

The present step is a reaction for deprotecting an $OP^1$ part of a compound (XI) to synthesize a compound (I-A). The reaction may be treated preferably with a Lewis acid (e.g.: aluminum chloride).

A reaction temperature is 0 to 150° C., preferably 10 to 50° C.

As a reaction solvent, methylene chloride, THF and the like are exemplified.

A reaction time is a few minutes to a few tens hours, preferably 1 to 3 hours.

(Tenth Step)

The present step is a reaction for deprotecting an ester part ($COOP^3$) of a compound (X) to synthesize carboxylic acid (XII). Preferably, hydrolysis with an alkali (e.g.: NaOH) may be performed.

A reaction temperature is 0 to 150° C., preferably 10 to 50° C.

As a reaction solvent, methanol, water and the like are exemplified.

A reaction time is a few minutes to a few tens hours, preferably a few minutes to 2 hours.

Carboxylic acid (XII) can be converted into various derivatives (e.g.; amide).

(Eleventh Step)

The present step is a reaction for reacting a compound (XII) with various amines to synthesize a compound (XIII). The reaction may be performed according to the condition for a reaction of amidating carboxylic acid which is generally performed and, for example, the reaction may be performed as in the first step.

A reaction temperature is 0 to 150° C., preferably room temperature to 70° C.

As a reaction solvent, a non-protonic solvent can be broadly used, and tetrahydrofuran (THF), 1,4-dioxane, dimethylformamide (DMF), methylene chloride, chloroform and the like are preferable.

A reaction time is a few minutes to a few tens hours, preferably a few minutes to 3 hours.

An amide part of the resulting compound (XIII) may be further chemically modified (e.g.: N-alkylation).

(Twelfth Step)

The present step is a reaction for deprotecting $OP^1$ and $OP^2$ parts of a compound (XIII) to synthesize a compound (I-B). The reaction may be performed according to the condition for a reaction of deprotecting a hydroxy protecting group which is generally performed.

For example, when pyridine hydrochloride is used, a reaction temperature is 0 to 200° C., preferably 150 to 180 degree.

A reaction time is a few minutes to a few tens hours, preferably 1 to 5 minutes.

As a reaction solvent, methanol, water and the like are exemplified.

A reaction time is a few minutes to a few tens hours, preferably a few minutes to 3 hours.

(Fourteenth Step)

The present step is a reaction for deprotecting an $OP^1$ part of a compound (XIV) to synthesize a compound (I-C). The reaction may be treated preferably with a Lewis acid (e.g.: boron tribromide).

A reaction temperature is 0 to 150° C., preferably under ice-cooling to room temperature.

As a reaction solvent, dichloromethane and the like are exemplified.

A reaction time is a few minutes to a few tens hours, preferably a few minutes to 5 hours.

The monocyclic carbamoylpyridone derivative obtained above is derived into a bicyclic compound by the following method.

(Process 1)

[Chemical formula 42]

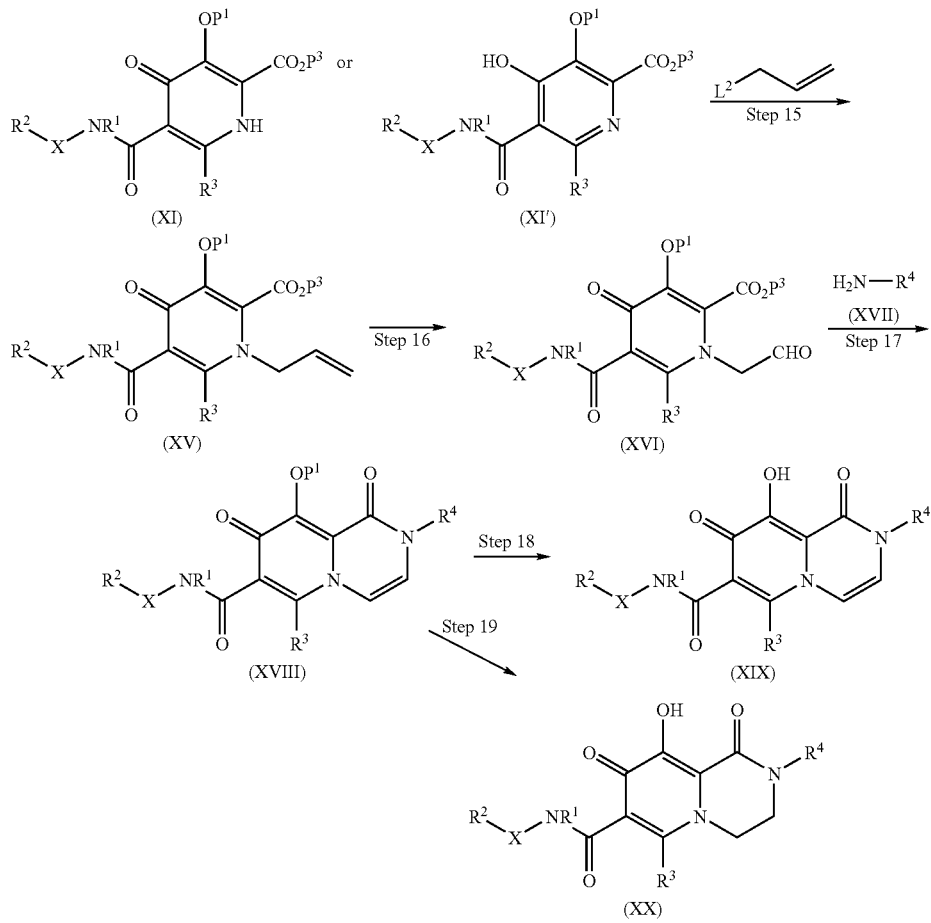

(Thirteenth Step)

The present step is a reaction for deprotecting an ester part ($COOP^3$) of a compound (XI) to synthesize carboxylic acid (XIV). Preferably, hydrolysis with an alkali (e.g.: lithium hydroxide) may be performed.

A reaction temperature is 0 to 150° C., preferably 10 to 50° C.

(wherein $R^1$, X, $R^2$, $P^1$, $P^3$ and $R^4$ are as define above, and $L^2$ is a leaving group such as halogen etc.)

(Fifteenth Step)

The present step is a reaction for reacting the compound (XI) or a compound (XI') which is a tautomer thereof with an allyl compound to synthesize a compound (XV). A compound (XI') can be synthesized, for example, according to the method of Example A-1.

The reaction is performed preferably in the presence of a base (e.g.: cesium carbonate).

A reaction temperature is 0 to 100° C., preferably 10 to 40° C.

As a reaction solvent, dimethylformamide and the like are exemplified.

A reaction time is a few minutes to a few tens hours, preferably 1 to 10 hours.

(Sixteenth Step)

The present step is a reaction for oxidizing a compound (XV) to synthesize a compound (XVI). As an oxidizing agent, osmium tetraoxide and alkali metal osmium tetraoxide (e.g.: $K_2OsO_4$) are exemplified.

A reaction temperature is 0 to 100° C., preferably 10 to 40° C.

As a reaction solvent, 1,4-dioxane, tetrahydrofuran and the like are exemplified.

A reaction time is a few minutes to a few tens hours, preferably 1 to 5 hours.

(Seventeenth Step)

The present step is a reaction for reacting a compound (XVI) with amine (XVII) to perform dehydration condensation to synthesize a compound (XVIII).

A reaction temperature is 0 to 200° C., preferably 140 to 180° C.

As a reaction solvent, methylene chloride, acetonitrile and the like are exemplified.

A reaction time is a few minutes to a few tens hours, preferably 0.5 to 1.5 hours.

(Eighteenth Step)

The present step is a reaction for deprotecting a compound (XVIII) preferably with an acid to synthesize a compound (XIX), and may be performed according to the condition for a conventional reaction of deprotecting a protected hydroxy group.

A reaction temperature is 0 to 200° C.

As an acid, pyridine hydrochloride, trifluoroacetic acid and the like are exemplified.

As a reaction solvent, the above acid and trimethylsilyl iodide are exemplified.

A reaction time is a few minutes to a few tens hours, preferably 15 minutes to 1 hour.

(Nineteenth Step)

The present step is a reaction for reducing a compound (XVIII) to synthesize a compound (XX).

As a reducing agent, $H_2/Pd.C$ and the like are exemplified.

A reaction temperature is 0 to 100° C., preferably 10 to 30° C.

As a reaction solvent, dimethylformamide, methanol, tetrahydrofuran and the like are exemplified.

A reaction time is a few minutes to a few tens hours, preferably 5 to 20 hours.

(Process 2)

The intermediate (XVIII) may be also synthesized by a method shown below.

[Chemical formula 43]

(Twentieth Step)

The present step is a reaction for reacting a compound (XIV) with a compound (XXI) to synthesize a compound (XXII). The present reaction may be performed according to the condition for a conventional amidation reaction.

A reaction temperature is 0 to 100° C., preferably 0 to 50° C.

As a reaction solvent, dimethylformamide, methylene chloride, tetrahydrofuran and the like are exemplified.

A reaction time is a few minutes to a few tens hours, preferably 1 to 10 hours.

(Twenty-First Step)

The present step is a reaction for reacting a compound (XXII) with an acid to perform deprotection and intramolecular ring closure, to synthesize a compound (XXIII). The present reaction may be performed according to the condition for a conventional reaction of deprotecting acetal.

A reaction temperature is 0 to 100° C., preferably room temperature to 80° C.

As a reaction solvent, dioxane, tetrahydrofuran and the like are exemplified.

A reaction time is a few minutes to a few tens hours, preferably 0.5 to 1 hour.

As an acid, hydrochloric acid, and paratoluenesulfonic acid are exemplified.

(Twenty-Second Step)

The present step is a reaction for dehydrating a compound (XXIII) to synthesize a compound (XXIV). The present reaction may be performed according to the condition for a conventional dehydration reaction.

A reaction temperature is 0 to 100° C., preferably room temperature to 80° C.

As a reaction solvent, acetonitrile, methylene chloride and the like are exemplified.

A reaction time is a few minutes to a few tens hours, preferably 1 to 5 hours.

In addition, the present compound obtained above may be further chemically modified to synthesize another compound. In addition, when there is a reactive functional group (e.g.: OH, COOH, $NH_2$) on a side chain part etc. in the above reaction, the group may be protected before the reaction and may be deprotected after the reaction, if desired.

The present compound is useful, for example, as a drug such as an anti-viral drug. The present compound has the remarkable inhibitory action on integrase of a virus. Therefore, the present compound can be expected to have the preventive or therapeutic effect for various diseases derived from a virus which produces at least integrase, and is grown at infection in an animal cell, and is useful as an integrase inhibiting agent for retrovirus (e.g. HIV-1, HIV-2, HTLV-1, SIV, FIV etc.), and is useful as an anti-HIV drug etc.

In addition, the present compound may be used in joint use therapy by combining an anti-HIV drug having the different action mechanism such as a reverse transcriptase inhibiter and/or a protease inhibiting agent. Particularly, currently, an integrase inhibitor is not marketed, and it is useful to use in joint use therapy by combining the present compound with a reverse transcriptase inhibiter and/or a protease inhibitor.

Further, the above use includes not only use as a medical mixture for anti-HIV, but also use as a joint use agent for increasing the anti-HIV activity of other anti-HIV drug such as cocktail therapy.

In addition, the present compound can be used in order to prevent infection with a retrovirus vector from spreading into a tissue other than an objective tissue, upon use of a retrovirus vector based on HIV or MLV in the field of gene therapy. Particularly, when a cell is infected with a vector in vitro, and the cell is returned into a body, if the present compound is administered in advance, extra infection can be prevented in a body.

The present compound can be administered orally or parenterally. In the case of oral administration, the present compound can be also used as a conventional preparation, for example, as any dosage form of a solid agent such as tablets, powders, granules, capsules and the like; an aqueous agent; an oily suspension; or a liquid agent such as syrup and elixir. In the case of parenteral administration, the present compound can be used as an aqueous or oily suspension injectable, or a nasal drop. Upon preparation of it, conventional excipients, binders, lubricants, aqueous solvents, oily solvents, emulsifiers, suspending agents, preservatives, stabilizers and the like may be arbitrarily used. As an anti-HIV-drug, particularly, an oral agent is preferable. A preparation of the present invention is prepared by combining (e.g. mixing) a therapeutically effective amount of the present compound with a pharmaceutically acceptable carrier or diluent.

A dose of the present invention is different depending on an administration method, an age, a weight and condition of a patient, and a kind of a disease and, usually, in the case of oral administration, about 0.05 mg to 3000 mg, preferably about 0.1 mg to 1000 mg may be administered per adult a day, if necessary, by dividing the dose. In addition, in the case of parenteral administration, about 0.01 mg to 1000 mg, preferably about 0.05 mg to 500 mg is administered per adult a day.

Examples are shown below.

Example A-1

9-Hydroxy-2-(2-methoxy-ethyl)-1,8-dioxo-1,8-dihydro-2H-pyrid[1,2-a]pyrazine-7-carboxylic acid 4-fluoro-banzylamide Example B-1

9-Hydroxy-2-(2-methoxy-ethyl)-1,8-dioxo-1,3,4,8-tetrahydro-2H-pyrid[1,2-a]pyrazine-7-carboxylic acid 4-fluoro-benzylamide

[Chemical formula 52]

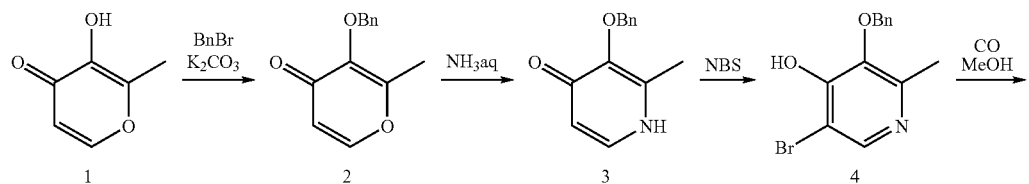

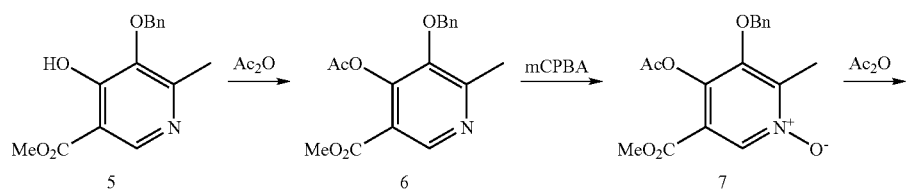

-continued
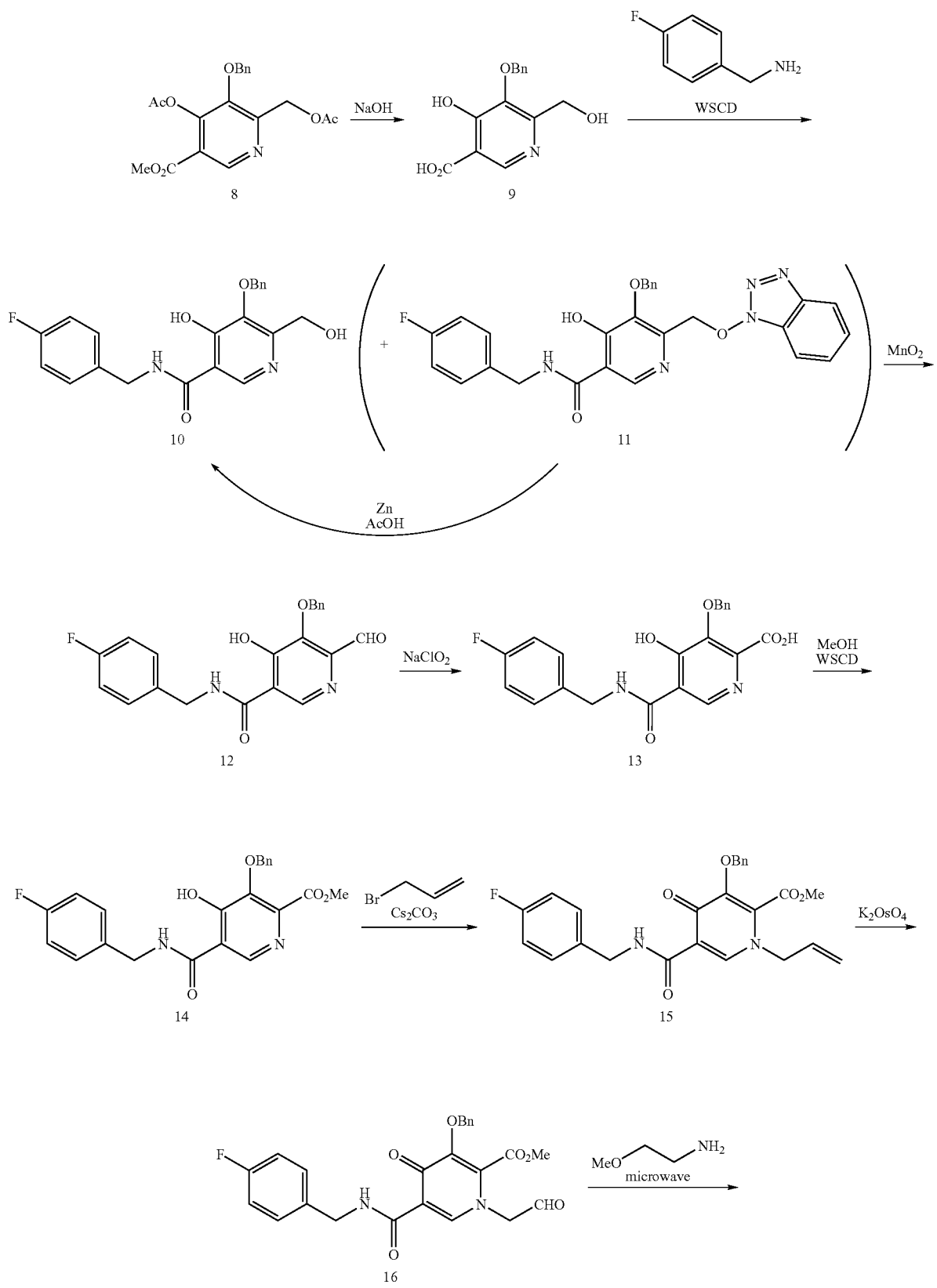

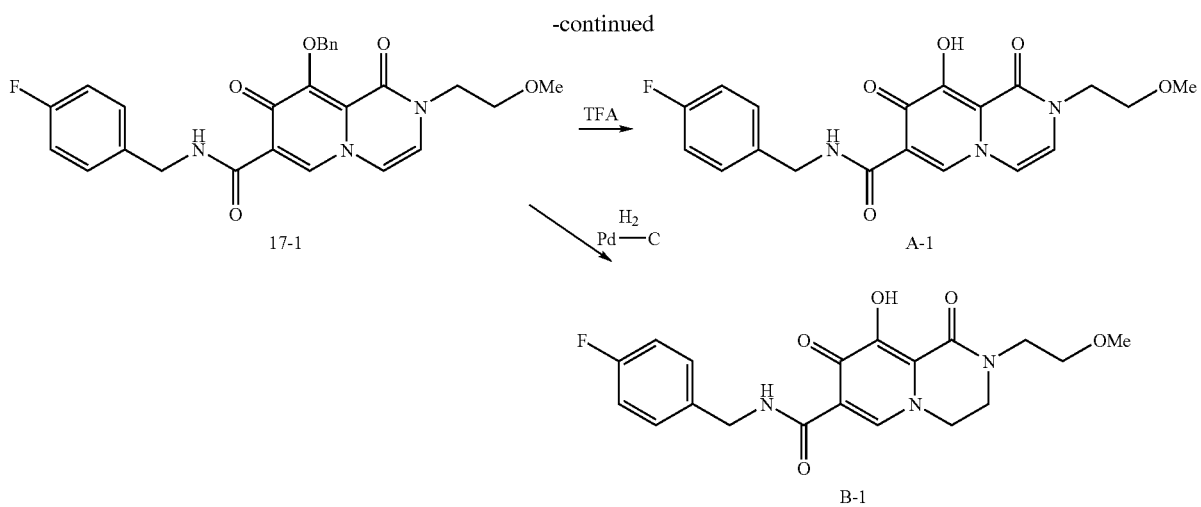

1) Maltol 1 (189 g, 1.5 mol) was dissolved in dimethylformamide (1890 ml), and benzyl bromide (184 ml, 1.5 mol) was added. After the solution was stirred at 80° C. for 15 minutes, potassium carbonate (228 g, 1.65 mol) was added, and the mixture was stirred for 1 hour. After the reaction solution was cooled to room temperature, an inorganic salt was filtered, and the filtrate was distilled off under reduced pressure. To the again precipitated inorganic salt was added tetrahydrofuran (1000 ml), this was filtered, and the filtrate was distilled off under reduced pressure to obtain the crude product (329 g, >100%) of 3-benzyloxy-2-methyl-pyran-4-one 2 as a brown oil.

NMR (CDCl$_3$) δ: 2.09 (3H, s), 5.15 (2H, s), 6.36 (1H, d, J=5.6 Hz), 7.29-7.41 (5H, m), 7.60 (1H, d, J=5.6 Hz).

2) The compound 2 (162.2 g, 750 mmol) was dissolved in ethanol (487 ml), and aqueous ammonia (28%, 974 ml) and a 6N aqueous sodium hydroxide solution (150 ml, 900 mmol) were added. After the reaction solution was stirred at 90° C. for 1 hour, this was cooled to under ice-cooling, and ammonium chloride (58 g, 1080 mmol) was added. To the reaction solution was added chloroform, this was extracted, and the organic layer was washed with an aqueous saturated sodium bicarbonate solution, and dried with anhydrous sodium sulfate. The solvent was distilled off under reduced pressure, isopropyl alcohol and diethyl ether were added to the residue, and precipitated crystals were filtered to obtain 3-benzyloxy-2-methyl-1H-pyridine-4-one 3 (69.1 g, 43%) as a pale yellow crystal.

NMR (DMSO-d$_6$) δ: 2.05 (3H, s), 5.04 (2H, s), 6.14 (1H, d, J=7.0 Hz), 7.31-7.42 (5H, m), 7.46 (1H, d, J=7.2 Hz), 11.29 (1H, brs).

3) The above compound 3 (129 g, 599 mmol) was suspended in acetonitrile (1300 ml), and N-bromosuccinic acid imide (117 g, 659 mmol) was added, followed by stirring at room temperature for 90 minutes. Precipitated crystals were filtered, and washed with acetonitrile and diethyl ether to obtain 3-benzyloxy-5-bromo-2-methyl-pyridine-4-ol 4 (154 g, 88%) as a colorless crystal.

NMR (DMSO-d$_6$) δ: 2.06 (3H, s), 5.04 (2H, s), 7.32-7.42 (5H, m), 8.03 (1H, d, J=5.5 Hz), 11.82 (1H, brs).

4) To a solution of the compound 4 (88 g, 300 mmol), palladium acetate (13.4 g, 60 mmol) and 1,3-bis(diphenylphosphino)propane (30.8 g, 516 mmol) in dimethylformamide (660 ml) were added methanol (264 ml) and triethylamine (210 ml, 1.5 mol) at room temperature. The interior of a reaction vessel was replaced with carbon monoxide, and the material was stirred at room temperature for 30 minutes, and stirred at 80 degree for 18 hours. A vessel to which ethyl acetate (1500 ml), an aqueous saturated ammonium chloride solution (1500 ml) and water (1500 ml) had been added was stirred under ice-cooling, and the reaction solution was added thereto. Precipitates were filtered, and washed with water (300 ml), ethyl acetate (300 ml) and diethyl ether (300 ml) to obtain 5-benzyloxy-4-hydroxy-6-methyl-nicotinic acid methyl ester 5 (44.9 g, 55%) as a colorless crystal.

NMR (DMSO-d$_6$) δ: 2.06 (3H, s), 3.72 (3H, s), 5.02 (2H, s), 7.33-7.42 (5H, m), 8.07 (1H, s).

5) After a solution of the compound 5 (19.1 g, 70 mmol) in acetic anhydride (134 ml) was stirred at 130° C. for 40 minutes, the solvent was distilled off under reduced pressure to obtain 4-acetoxy-5-benzyloxy-6-methyl-nicotinic acid methyl ester 6 (19.9 g, 90%) as a flesh colored crystal.

NMR (CDCl$_3$) δ: 2.29 (3H, s), 2.52 (3H, s), 3.89 (3H, s), 4.98 (2H, s), 7.36-7.41 (5H, m), 8.85 (1H, s).

6) To a solution of the compound 6 (46.2 g, 147 mmol) in chloroform (370 ml) was added metachloroperbenzoic acid (65%) (42.8 g, 161 mmol) in portions under ice-cooling, and this was stirred at room temperature for 90 minutes. To the reaction solution was added a 10% aqueous potassium carbonate solution, and this was stirred for 10 minutes, followed by extraction with chloroform. The organic layer was washed with successively with a 10% aqueous potassium carbonate solution, an aqueous saturated ammonium chloride solution, and an aqueous saturated sodium chloride solution, and dried with anhydrous sodium sulfate. The solvent was distilled off under reduced pressure, and the residue was washed with diisopropyl ether to obtain 4-acetoxy-5-benzyloxy-6-methyl-1-oxy-nicotinic acid methyl ester 7 (42.6 g, 87%) as a colorless crystal.

NMR (CDCl$_3$) δ: 2.30 (3H, s), 2.41 (3H, s), 3.90 (3H, s), 5.02 (2H, s), 7.37-7.39 (5H, m), 8.70 (1H, s).

7) To acetic anhydride (500 ml) which had been heated to stir at 130° C. was added the compound 7 (42.6 g, 129 mmol) over 2 minutes, and this was stirred for 20 minutes. The solvent was distilled off under reduced pressure to obtain 4-acetoxy- 6-acetoxymethyl-5-benzyloxy-nicotinic acid methyl ester 8 (49.6 g, >100%) as a black oil.

NMR (CDCl$_3$) δ: 2.10 (3H, s), 2.28 (3H, s), 3.91 (3H, s), 5.07 (2H, s), 5.20 (2H, s), 7.35-7.41 (5H, m), 8.94 (1H, s).

8) To a solution of the compound 8 (46.8 g, 125 mmol) in methanol (140 ml) was added a 2N aqueous sodium hydroxide solution (376 ml) under ice-cooling, and this was stirred at 50° C. for 40 minutes. To the reaction solution were added diethyl ether and 2N hydrochloric acid under ice-cooling, and precipitated crystals were filtered. Resulting crystals were washed with water and diethyl ether to obtain 5-benzyloxy-4-hydroxy-6-hydroxymethyl-nicotinic acid 9 (23.3 g, 68%) as a colorless crystal.

NMR (DMSO-d$_6$) δ: 4.49 (2H, s), 5.19 (2H, s), 5.85 (1H; brs), 7.14-7.20 (2H, m), 7.33-7.43 (7H, m), 8.30 (1H, s), 10.73 (1H, t, J=5.8 Hz), 11.96 (1H, brs).

9) To a solution of the compound 9 (131 g, 475 mmol), 1-(3-dimethylaminopropyl)-3-ethylcarbodiimide hydrochloride (219 g, 1140 mmol) and 1-hydroxybenzotriazole (128 g, 950 mmol) in dimethylformamide (1300 ml) was added 4-fluorobenzylamine (109 ml, 950 mmol), and this was stirred at 80° C. for 1.5 hours. After the reaction solution was cooled to room temperature, hydrochloric acid was added, followed by extraction with ethyl acetate. The extract was washed with a 5% aqueous potassium carbonate solution, an aqueous saturated ammonium chloride solution, and an aqueous saturated sodium chloride solution, and dried with anhydrous sodium sulfate. The solvent was distilled off under reduced pressure to obtain a mixture (175 g) of 10 and 11. The resulting mixture was dissolved in acetic acid (1050 ml) and water (1050 ml), and zinc (31.1 g, 475 mmol) was added, followed by heating to reflux for 1 hour. After the reaction solution was cooled to room temperature, a 10% aqueous potassium carbonate solution was added, followed by extraction with ethyl acetate. The extract was washed with an aqueous saturated ammonium chloride solution, and an aqueous saturated sodium chloride solution, and dried with anhydrous sodium sulfate. After the solvent was distilled off under reduced pressure, this was washed with diethyl ether to obtain 5-benzyloxy-N-(4-fluoro-benzyl)-4-hydroxy-6-hydroxymethyl-nicotinic acid amide 10 (107 g, 59%) as a colorless crystal.

NMR (DMSO-d$_6$) δ: 4.45 (2H, d, J=4.3 Hz), 4.52 (2H, d, J=5.8 Hz), 5.09 (2H, s), 6.01 (1H, brs), 7.36-7.43 (5H, m), 8.31 (1H, s), 12.63 (1H, brs).

10) After manganese dioxide (49 g) was added to a suspension of the compound 10 (9.8 g, 25.6 mmol) in chloroform (490 ml), the mixture was stirred at room temperature for 1 hour. After the reaction solution was stirred at 60° C. for 20 minutes, Celite filtration was performed, and this was washed with chloroform heated at 50° C. The filtrate was distilled off under reduced pressure to obtain 5-benzyloxy-N-(4-fluoro-benzyl)-6-formyl-4-hydroxy-nicotinic acid amide 12 (8.2 g, 84%) as a pale yellow crystal.

NMR (DMSO-d$_6$) δ: 4.53 (2H, d, J=5.8 Hz), 5.38 (2H, s), 7.15-7.21 (2H, m), 7.35-7.46 (7H, m), 8.33 (1H, s), 9.90 (1H, s), 10.35 (1H, t, J=5.8 Hz), 12.49 (1H, brs).

11) To an aqueous solution (105 ml) of sodium chlorite (7.13 g, 78.8 mmol), and sulfamic acid (7.65 g, 78.8 mmol) was added a solution of the compound 12 (15.0 g, 39.4 mmol) in tetrahydrofuran (630 ml) under ice-cooling, and the mixture was stirred at room temperature for 1 hour. After water (2500 ml) was added to the reaction solution, precipitated crystals were filtered. Washing with diethyl ether afforded 3-benzyloxy-5-(4-fluoro-benzylcarbamoyl)-4-hydroxy-pyridine-2-carboxylic acid 13 (14.0 g, 90%) as a colorless crystal.

NMR (DMSO-d$_6$) δ: 4.52 (2H, d, J=5.8 Hz), 5.13 (2H, s), 7.14-7.19 (2H, m), 7.31-7.40 (5H, m), 7.47-7.49 (2H, m), 8.31 (1H, d, J=4.5 Hz), 10.44 (1H, t, J=5.9 Hz), 12.47 (1H, brs).

12) A solution of the compound 13 (198 mg, 0.500 mmol), 1-(3-dimethylaminopropyl)-3-ethylcarbodiimide hydrochloride (115 mg, 0.600 mmol) and 1-hydroxybenzotriazole (81 mg, 0.600 mmol) in dimethylformamide (3 ml) was stirred at room temperature for 1.5 hours. Then, methanol (3 ml) and triethylamine (153 ul, 1.10 mmol) were added, and the mixture was heated to reflux for 1.5 hours. The reaction solution was diluted with ethyl acetate, washed with an aqueous saturated sodium bicarbonate solution, a 10% aqueous citric acid solution, and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-hydroxy-pyridine-2-carboxylic acid methyl ester 14 (141 mg, 69%) as a colorless crystal.

NMR (DMSO-d$_6$) δ: 3.85 (3H, s), 4.52 (2H, d, J=6.0 Hz), 5.15 (2H, s), 7.13-7.21 (2H, m), 7.31-7.47 (7H, m), 8.33 (1H, s), 10.41 (1H, t, J=6.0 Hz), 12.59 (1H, brs).

13) After 3-bromopropene (2.15 ml, 24.8 mmol) was added to a solution of the compound 14 (6.79 g, 16.5 mmol), and cesium carbonate (8.09 g, 24.8 mmol) in dimethylformamide (54 ml), the mixture was stirred at room temperature for 4.5 hours. To the reaction solution was added an aqueous ammonium chloride solution, and this was extracted with ethyl acetate, washed with water and an aqueous saturated sodium chloride solution, and dried with anhydrous sodium sulfate. The solvent was distilled off under reduced pressure, and the residue was washed with diethyl ether to obtain 1-allyl-3-benzyloxy-5-(4-fluoro-benzylcarbamoyl)-4-oxo-1,4-dihydro-pyridine-2-carboxylic acid methyl ester 15 (6.15 g, 83%) as a colorless crystal.

NMR (CDCl$_3$) δ: 3.76 (3H, s), 4.54 (2H, d, J=6.0 Hz), 4.60 (2H, d, J=6.0 Hz), 5.20-5.37 (2H, m), 5.25 (2H, s), 5.80-5.93 (1H, m), 6.98-7.04 (2H, m), 7.31-7.35 (7H, m), 8.45 (1H, s), 10.41 (1H, m).

14) To a solution of the compound 15 (7.6 g, 16.9 mmol) in 1,4-dioxane (228 ml) was added an aqueous solution (38 ml) of potassium osmate dihydrate (372 mg, 1.01 mmol), and sodium metaperiodate (14.5 g, 67.6 mmol) was further added, followed by stirring at room temperature for 2 hours. The reaction solution was added to a vessel to which ethyl acetate (300 ml) and water (300 ml) had been added, while stirring. The organic layer was washed with water, a 5% aqueous sodium hydrogen sulfite solution and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-oxo-1-(2-oxo-ethyl)-1,4-dihydro-pyridine-2-carboxylic acid methyl ester 16 (5.39 g, 71%) as a colorless crystal.

NMR (CDCl$_3$) δ: 3.74 (3H, s), 4.60 (2H, d, J=5.9 Hz), 4.87 (2H, s), 5.27 (2H, s), 6.98-7.04 (2H, m), 7.30-7.40 (7H, m), 8.39 (1H, s), 9.58 (1H, s), 10.38 (1H, s).

15) To a solution of the compound 16 (400 mg, 0.884 mmol) in methylene chloride (12 ml) were added 2-methoxyethylamine (77 ul, 0.884 mmol) and acetic acid (18 ul), and the mixture was stirred at room temperature for 5 minutes. Thereafter, the reaction was performed at 140° C. for 30 minutes in a microwave reaction apparatus. The solvent was distilled off under reduced pressure, the residue was subjected to silica gel column chromatography, and fractions eluting with toluene-acetone were concentrated under reduced pressure to obtain 9-benzyloxy-2-(2-methyl-ethyl)-1,8-dioxo-1,8-dihydro-2H-pyrid[1,2-a]pyrazine-7-carboxylic acid 4-fluoro-benzylamide 17-1 (226 mg, 54%) as a yellow solid.

NMR (CDCl$_3$) δ: 3.35 (3H, s), 3.65 (2H, t, J=5.1 Hz), 3.97 (2H, t, J=4.5 Hz), 4.63 (2H, d, J=5.7 Hz), 5.28 (2H, s), 6.56 (2H, m), 7.01 (2H, t, J=8.7 Hz), 7.38-7.30 (5H, m), 7.65 (2H, d, J=6.6 Hz), 10.63 (1H, s).

According to the similar method, the following compounds were synthesized.

Compound 17-2

9-Benzyloxy-2-(2-dimethylamino-ethyl)-1,8-dioxo-1,8-dihydro-2H-pyrid[1,2-a]pyrazine-7-carboxylic acid 7-fluoro-benzylamide NMR (CDCl$_3$) δ: 2.68 (6H, s), 3.33 (2H, t, J=6.6 Hz), 4.28 (2H, t, J=6.6 Hz), 4.62 (2H, d, J=6.0 Hz), 5.25 (2H, s), 6.85-6.92 (2H, m), 7.03 (2H, t, J=8.7 Hz), 7.31-7.40 (5H, m), 7.62 (2H, d, J=6.3 Hz), 8.65 (1H, s), 10.63 (1H, t, J=6.0 Hz).

Compound 17-3

9-Benzyloxy-2-(2-morpholin-4-yl-ethyl)-1,8-dioxo-1,8-dihydro-2H-pyrid[1,2-a]pyrazine-7-carboxylic acid 4-fluoro-benzylamide NMR (CDCl$_3$) δ: 2.59 (4H, s), 2.74 (2H, s), 3.73 (4H, s), 3.95 (2H, s), 4.62 (2H, d, J=6.0 Hz), 5.28 (1H, s), 6.53 (1H, d, J=6.0 Hz), 6.63 (1H, d, J=6.0 Hz), 7.01 (2H, t, J=8.7 Hz), 7.26-7.38 (5H, m), 7.64 (2H, d, J=6.9 Hz), 8.61 (1H, s), 10.61 (1H, t, J=5.4 Hz).

Compound 17-4

9-Benzyloxy-1,8-dioxo-2-(2-piperidin-1-yl-ethyl)-1,8-dihydro-2H-pyrid[1,2-a]pyrazine-7-carboxylic acid 4-fluoro-benzylamide NMR (CDCl$_3$) δ: 1.55-1.76 (6H, m), 2.71-2.87 (6H, m), 4.13 (2H, brs), 4.62 (2H, d, J=6 Hz), 5.28 (2H, s), 6.62 (1H, d, J=6.2 Hz), 6.77 (1H; m), 6.97-7.04 (2H, m), 7.30-7.39 (5H, m), 7.62-7.63 (2H, m), 8.59 (1H, s), 10.56-10.61 (1H, m).

Compound 17-5

9-Benzyloxy-2-(2-methyl-butyl)-1,8-dioxo-1,8-dihydro-2H-pyrid[1,2-a]pyrazine-7-carboxylic acid 4-fluoro-benzylamide NMR (CDCl$_3$) δ: 0.92-0.99 (6H, m), 1.17-1.26 (1H, m), 1.44-1.50 (1H, m), 1.88-1.92 (1H, m), 3.52-3.59 (1H, m), 3.68-3.75 (1H, m), 4.62 (2H, d, J=6 Hz), 5.29 (2H, s), 6.36 (1H, d, J=6 Hz), 6.59 (1H, d, J=6 Hz), 6.98-7.04 (2H, m), 7.29-7.37 (5H, m), 7.62-7.65 (2H, m), 8.57 (1H, s), 10.62 (1H, m).

Compound 17-6

9-Benzyloxy-2-(2-isopropoxy-ethyl)-1,8-dioxo-1,8-dihydro-2H-pyrid[1,2-a]pyrazine-7-carboxylic acid 4-fluoro-benzylamide NMR (CDCl$_3$) δ: 1.12 (6H, d, J=6 Hz), 3.51-3.59 (1H, m), 3.68 (2H, t, J=4.8 Hz), 3.96 (2H, t, J=4.8 Hz), 4.62 (2H, d, J=6 Hz), 5.28 (2H, s), 6.58-6.64 (2H, m), 6.98-7.04 (2H, m), 7.30-7.39 (5H, m), 7.64-7.66 (2H, m), 8.59 (1H, brs), 10.63 (1H, brs).

Compound 17-7

9-Benzyloxy-2-isopropyl-1,8-dioxo-1,8-dihydro-2H-pyrid[1,2-a]pyrazine-7-carboxylic acid 4-fluoro-benzylamide NMR (CDCl$_3$) δ: 1.31 (6H, d, J=6.9 Hz), 4.62 (2H, d, J=6.0 Hz), 5.08-5.17 (1H, m), 5.27 (2H, s), 6.39 (1H, d, J=6.3 Hz), 6.73 (1H, d, J=6.3 Hz), 6.98-7.04 (2H, m), 7.16-7.39 (5H, m), 7.66-7.68 (2H, m), 8.66 (1H, s), 10.67 (1H, t, J=5.5 Hz).

Compound 17-8

9-Benzyloxy-2-cyclohexyl-1,8-dioxo-1,8-dihydro-2H-pyrid[1,2-a]pyrazine-7-carboxylic acid 4-fluoro-benzylamide NMR (CDCl$_3$) δ: 1.15-1.92 (10H, m), 4.62 (2H, d, J=6.1 Hz), 4.70-4.78 (1H, m), 5.27 (2H, s), 6.43 (1H, d, J=6.4 Hz), 6.69 (1H, d, J=6.3 Hz), 7.01-7.16 (2H, m), 7.18-7.37 (5H, m), 7.66-7.68 (2H, m), 8.63 (1H, s), 10.67 (1H, t, J=5.5 Hz).

Compound 17-9

9-Benzyloxy-2-(4-fluoro-benzyl)-1,8-dioxo-1,8-dihydro-2H-pyrid[1,2-a]pyrazine-7-carboxylic acid 4-fluoro-benzylamide NMR (CDCl$_3$) δ: 4.61 (2H, d, J=6.0 Hz), 4.92 (2H, s), 5.31 (2H, s), 6.28 (1H, d, J=6.1 Hz), 6.62 (1H, d, J=6.3 Hz), 6.97-7.09 (4H, m), 7.25-7.38 (7H, m), 7.62-7.66 (2H, m), 8.60 (1H, s), 10.59 (1H, t, J=6.0 Hz).

Compound 17-10

9-Benzyloxy-1,8-dioxo-2-[2-(propyl-m-toluoyl-amino)-ethyl]-1,8-dihydro-2H-pyrid[1,2-a]pyrazine-7-carboxylic acid 4-fluoro-benzylamide NMR (CDCl$_3$) δ: 1.09 (3H, t, J=6.6 Hz), 2.29 (3H, s), 3.28-3.32 (2H, m), 3.61-3.65 (2H, m), 3.94-3.98 (2H, m), 4.62 (2H, d, J=5.7 Hz), 5.31 (2H, s), 6.21 (1H, d, J=6.0 Hz), 6.49 (1H, d, J=6.0 Hz), 6.54 (3H, brs), 6.89-7.04 (2H, m), 7.08-7.39 (6H, m), 7.66 (2H, d, J=6.3 Hz), 8.54 (1H, s), 10.57-10.62 (1H, m).

Compound 17-11

9-Benzyloxy-1,8-dioxo-2-[3-(2-oxo-pyrrolodin-1-yl)-propyl]-1,8-dihydro-2H-pyrid[1,2-a]pyrazine-7-carboxylic acid 4-fluoro-benzylamide NMR (CDCl$_3$) δ: 1.96 (2H, t, J=6.6 Hz), 2.07 (2H, t, J=7.5 Hz), 2.42 (2H, t, J=7.8 Hz), 3.36 (2H, t, J=6.6 Hz), 3.43 (2H, t, J=6.9 Hz), 3.76 (2H, t, J=6.6 Hz), 4.62 (2H, d, J=6.0 Hz), 5.28 (2H, s), 6.62 (1H, d, J=6.3 Hz), 6.78 (1H, d, J=6.3 Hz), 6.98-7.04 (2H, m), 7.30-7.38 (5H, m), 7.63-7.65 (2H, m), 8.59 (1H, s), 10.59-10.63 (1H, m).

Compound 17-12

9-Benzyloxy-1,8-dioxo-2-(2-tetrahydrofuran-2-ylmethyl)-1,8-dihydro-2H-pyrid[1,2-a]pyrazine-7-carboxylic acid 4-fluoro-benzylamide NMR (CDCl$_3$) δ: 1.48-1.62 (1H, m), 1.87-1.98 (2H, m), 2.05-2.17 (1H, m), 3.47 (1H, dd, J=14.1, 8.1 Hz), 3.73-3.82 (1H, m), 3.84-3.92 (1H, m), 4.12-4.21 (1H, m), 4.21 (1H, dd, J=13.8, 2.4 Hz), 4.62 (2H, d, J=6.0 Hz), 5.28 (2H, s), 6.58 (1H, d, J=6.2 Hz), 6.67 (1H, d, J=6.2 Hz), 6.97-7.05 (2H, m), 7.28-7.39 (5H, m), 7.62-7.66 (2H, m), 8.58 (1H, m), 10.60-10.68 (1H, m).

Compound 17-13

9-Benzyloxy-1,8-dioxo-2-pyridin-4-ylmethyl-1,8-dihydro-2H-pyrid[1,2-a]pyrazine-7-carboxylic acid 4-fluoro-benzylamide NMR (CDCl$_3$) δ: 4.63 (2H, d, J=6.0 Hz), 5.00 (2H, s), 5.31 (2H, s), 6.37 (1H, d, J=6.1 Hz), 6.68 (1H, d, J=6.1 Hz), 6.97-7.06 (2H, m), 7.28-7.38 (7H, m), 7.56-7.61 (2H, m), 8.61 (1H, s), 8.62-8.66 (2H, m), 10.50 (1H, t, J=6.0 Hz).

Compound 17-14

4-[9-Benzyloxy-7-(4-fluoro-benzylcarbamoyl)-1,8-dioxo-1,8-dihydro-2H-pyrid[1,2-a]pyrazin-2-yl]-piperidine-1-carboxylic acid ethyl ester NMR (CDCl$_3$) δ: 1.26 (3H, t, J=7.0 Hz), 1.62-1.69 (2H, m), 1.84-1.87 (2H, m), 2.88-2.96 (2H, m), 4.16 (2H, q, J=7.0 Hz), 4.35 (2H, brs), 4.62 (2H, d, J=5.9 Hz), 5.27 (2H, s), 6.37 (1H, d, J=6.3 Hz), 6.69 (1H, d, J=5.6 Hz), 6.98-7.04 (2H, m), 7.16-7.40 (5H, m), 7.64-7.67 (2H, m), 8.62 (1H, brs), 10.59 (1H, brs).

Compound 17-15

9-Benzyloxy-2-methyl-1,8-dioxo-1,8-dihydro-2H-pyrid[1,2-a]pyrazine-7-carboxylic acid 4-fluoro-benzylamide NMR (CDCl$_3$) δ: 3.40 (3H, s), 4.62 (2H, d, J=6.0 Hz), 5.27 (2H, s), 6.37 (1H, d, J=6.0 Hz), 6.64 (1H, d, J=6.0 Hz), 6.97-7.05 (2H, m), 7.28-7.40 (5H, m), 7.63-7.68 (2H, m), 8.60 (1H, brs), 10.61 (1H, brs).

Compound 17-16

2-(2-Acetylamino-ethyl)-9-benzyloxy-1,8-dioxo-1,8-dihydro-2H-pyrid[1,2-a]pyrazine-7-carboxylic acid 4-fluoro-benzylamide NMR (DMSO-d$_6$) δ: 1.76 (3H, s), 3.33 (2H, s), 3.79 (2H, s), 4.55 (2H, d, J=5.1 Hz), 5.05 (2H, s), 6.89 (1H, d, J=6.0 Hz), 7.17 (2H, t, J=8.4 Hz), 7.30-7.50 (5H, m), 7.61 (2H, d, J=5.1 Hz), 7.96 (1H, s), 8.93 (1H, s), 10.61 (1H, s).

Compound 17-17

9-Benzyloxy-2-(3-isopropoxy-propyl)-1,8-dioxo-1,8-dihydro-2H-pyrid[1,2-a]pyrazine-7-carboxylic acid 4-fluoro-benzylamide NMR (CDCl$_3$) δ: 1.15 (6H, d, J=6.1 Hz), 1.93-2.02 (2H, m), 3.45 (2H, t, J=5.7 Hz), 3.55 (1H, sep, J=6.1 Hz), 3.90 (2H, d, J=6.8 Hz), 4.62 (2H, d, J=6.0 Hz), 5.28 (2H, s), 6.49 (1H, d, J=6.3 Hz), 6.59 (1H, d, J=6.3 Hz), 6.97-7.05 (2H, m), 7.27-7.38 (5H, m), 7.62-7.65 (2H, m), 8.58 (1H, s), 10.58-10.65 (1H, m).

Compound 17-18)

9-Benzyloxy-2-(4-dimethylamino-benzyl)-1,8-dioxo-1,8-dihydro-2H-pyrid[1,2-a]pyrazine-7-carboxylic acid 4-fluoro-benzylamide NMR (CDCl$_3$) δ: 2.98 (6H, s), 4.62 (2H, d, J=6.0 Hz), 4.88 (2H, s), 5.31 (2H, s), 6.35 (1H, d, J=6.2 Hz), 6.54 (1H, d, J=6.2 Hz), 6.77 (2H, brs), 6.87-7.05 (2H, m), 7.19-7.25 (2H, m), 7.29-7.41 (2H, m), 7.65-7.70 (2H, m), 8.54 (1H, s), 10.62 (1H, t, J=5.6 Hz).

Compound 17-19

9-Benzyloxy-1,8-dioxo-2-(4-sulfamoyl-1-benzyl)-1,8-dihydro-2H-pyrid[1,2-a]pyrazine-7-carboxylic acid 4-fluoro-benzylamide NMR (CDCl$_3$) δ: 4.62 (2H, s), 5.04 (2H, s), 5.28 (2H, s), 6.51 (1H, d, J=6.3 Hz), 6.87 (1H, d, J=6.3 Hz), 7.00-7.06 (2H, m), 7.20-7.40 (5H, m), 7.44-7.47 (2H, m), 7.59-7.62 (2H, m), 7.90-7.93 (2H, m), 8.63 (1H, s).

Compound 17-20

9-Benzyloxy-2-[3-(4-methyl-piperazin-1-yl)-propyl]-1,8-dioxo-1,8-dihydro-2H-pyrid[1,2-a]pyrazine-7-carboxylic acid 4-fluoro-benzylamide NMR (CDCl$_3$) δ: 1.87-1.97 (2H, m), 2.34 (3H, s), 2.42 (2H, d, J=6.8 Hz), 2.54 (8H, brs), 3.85 (2H, d, J=6.9 Hz), 4.62 (2H, d, J=5.9 Hz), 5.28 (2H, s), 6.52 (1H, d, J=6.3 Hz), 6.60 (1H, d, J=6.3 Hz), 6.95-7.05 (2H, m), 7.28-7.38 (5H, m), 7.61-7.66 (2H, m), 8.59 (1H, s), 10.61 (1H, t, J=5.9 Hz).

Compound 17-21

9-Benzyloxy-2-(3-methoxy-propyl)-1,8-dioxo-1,8-dihydro-2H-pyrid[1,2-a]pyrazine-7-carboxylic acid 4-fluoro-benzylamide NMR (CDCl$_3$) δ: 1.99 (2H, quin, J=5.7 Hz), 3.34 (3H, s), 3.60 (2H, t, J=6.3 Hz), 3.95 (2H, t, J=6.3 Hz), 4.62 (2H, d, J=5.7 Hz), 5.28 (2H, s), 6.45 (1H, d, J=6.3 Hz), 6.61 (1H, d, J=6.3 Hz), 7.01 (2H, t, J=6.6 Hz), 7.28-7.38 (5H, m), 7.64 (2H, d, J=6.6 Hz), 8.59 (1H, s), 10.62 (1H, s).

Compound 17-22

9-Benzyloxy-1,8-dioxo-2-(2-propoxy-ethyl)-1,8-dihydro-2H-pyrid[1,2-a]pyrazine-7-carboxylic acid 4-fluoro-benzylamide NMR (CDCl$_3$) δ: 0.89 (3H, t, J=7.5 Hz), 1.55 (2H, m), 3.38 (2H, t, J=6.6 Hz), 3.68 (2H, t, J=4.8 Hz), 3.98 (2H, t, J=4.5 Hz), 4.62 (2H, d, J=5.7 Hz), 5.28 (2H, s), 6.57 (1H, d, J=5.7 Hz), 6.60 (1H, d, J=5.7 Hz), 7.01 (2H, t, J=8.7 Hz), 7.30-7.38 (5H, m), 7.65 (2H, d, J=6.9 Hz), 8.59 (1H, s), 10.63 (1H, s).

Compound 17-23

9-Benzyloxy-1,8-dioxo-2-(2-phenoxy-ethyl)-1,8-dihydro-2H-pyrid[1,2-a]pyrazine-7-carboxylic acid 4-fluoro-benzylamide NMR (CDCl$_3$) δ: 4.17-4.20 (2H, m), 4.25-4.28 (2H, m), 4.62 (2H, d, J=5.6 Hz), 5.28 (2H, s), 6.60-6.66 (1H, m), 6.86 (2H, d, J=8.0 Hz), 6.95-7.04 (2H, m), 7.28-7.37 (8H, m), 7.64 (2H, d, J=7.0 Hz), 8.59 (1H, s), 10.60 (1H, brs).

Compound 17-24

9-Benzyloxy-1,8-dioxo-2-(piperizin-3-yl-ethyl)-1,8-dihydro-2H-pyrid[1,2-a]pyrazine-7-carboxylic acid 4-fluoro-benzylamide NMR (CDCl$_3$) δ: 3.04 (2H, t, J=7.2 Hz), 4.00 (2H, t, J=7.2 Hz), 4.62 (2H, d, J=6.0 Hz), 5.29 (2H, s), 6.10 (1H, d, J=6.3 Hz), 6.52 (1H, d, J=6.3 Hz), 7.01 (2H, m), 7.24 (1H, m), 7.30-7.39 (5H, m), 7.53 (1H, m), 7.62-7.66 (2H, m), 8.46 (1H, m), 8.52 (1H, dd, J=1.5 Hz, 4.5 Hz), 8.56 (1H, s), 10.57 (1H, brt, J=6.0 Hz).

Compound 17-25

9-Benzyloxy-2-dimethylcarbamoylmethyl-1,8-dioxo-1,8-dihydro-2H-pyrid[1, 2-a]pyrazine-7-carboxylic acid 4-fluoro-benzylamide NMR (CDCl$_3$) δ: 3.01 (3H, s), 3.13 (3H, s), 4.59 (2H, s), 4.63 (2H, d, J=6.0 Hz), 5.26 (2H, s), 6.42 (1H, d, J=6.0 Hz), 6.64 (1H, d, J=6.0 Hz), 7.01 (2H, m), 7.29-7.36 (5H, m), 7.64 (2H, m), 8.60 (1H, s), 10.59 (1H, brt, J=6.0 Hz).

Compound 17-26

9-Benzyloxy-2-(2-ethoxy-ethyl)-1,8-dioxo-1,8-dihydro-2H-pyrid[1,2-a]pyrazine-7-carboxylic acid 4-fluoro-benzylamide NMR (CDCl$_3$) δ: 1.18 (3H, t, J=7.0 Hz), 3.49 (2H, q, J=7.0 Hz), 3.66-3.71 (2H, m), 3.96-4.00 (2H, m), 4.63 (2H, d, J=6.0 Hz), 5.28 (2H, s), 6.57 (1H, d, J=5.9 Hz), 6.61 (1H, d, J=5.9 Hz), 6.98-7.06 (2H, m), 7.29-7.40 (5H, m), 7.63-7.67 (2H, m), 8.59 (1H, s), 10.60-10.68 (1H, m).

Compound 17-27

9-Benzyloxy-2-furan-2-ylmethyl-1,8-dioxo-1,8-dihydro-2H-pyrid[1,2-a]pyrazine-7-carboxylic acid 4-fluoro-benzylamide NMR (DMSO-d$_6$) δ: 4.55 (2H, d, J=5.7 Hz), 4.99 (2H, s), 5.07 (2H, s), 6.44 (1H, dd, J=1.8 Hz, 3.0 Hz), 6.51 (1H, dd, J=0.9 Hz, 3.0 Hz), 6.99 (1H, d, J=6.3 Hz), 7.17 (2H, m), 7.31-7.41 (4H, m), 7.46 (1H, d, J=6.6 Hz), 7.58-7.62 (2H, m), 7.65 (1H, dd, J=0.9 Hz, 1.8 Hz), 8.89 (1H, s), 10.57 (1H, brt, J=5.7 Hz).

Compound 17-28

9-Benzyloxy-2-[2-(4-chloro-phenyl)-ethyl]-1,8-dioxo-1,8-dihydro-2H-pyrid[1,2-a]pyrazine-7-carboxylic acid 4-fluoro-benzylamide NMR (CDCl$_3$) δ: 3.00 (2H, t, J=7.2 Hz), 3.98 (2H, t, J=7.2 Hz), 4.62 (2H, d, J=5.4 Hz), 5.30 (2H, s), 6.06 (1H, d, J=6.3 Hz), 6.46 (1H, d, J=6.3 Hz), 7.01 (2H, m), 7.11 (2H, m), 7.17-7.40 (9H, m), 7.64 (2H, m), 8.53 (1H, s), 10.58 (1H, brt, J=5.4 Hz).

Compound 17-29

9-Benzyloxy-2-(1-benzyl-pyrrolidin-3-yl)-1,8-dioxo-1,8-dihydro-2H-pyrid[1,2-a]pyrazine-7-carboxylic acid 4-fluoro-benzylamide NMR (CDCl$_3$) δ: 1.75 (1H, m), 2.21 (1H, m), 2.44-2.55 (2H, m), 2.87 (1H, brd, J=10.8 Hz), 3.15 (1H, brt, J=8.7 Hz), 3.56 (1H, d, J=9.9 Hz), 3.69 (1H, d, J=9.9 Hz), 4.62 (2H, d, J=5.7 Hz), 5.25 (2H, s), 6.66 (1H, d, J=6.3 Hz), 6.98 (1H, d, J=6.3 Hz), 7.00 (2H, m), 7.15-7.38 (10H, m), 7.62-7.66 (2H, m), 8.58 (1H, s), 10.63 (1H, brt, J=5.7 Hz).

Compound 17-30

9-Benzyloxy-1,8-dioxo-2-thiophen-2-ylmethyl-1,8-dihydro-2H-pyrid[1,2-a]pyrazine-7-carboxylic acid 4-fluoro-benzylamide NMR (CDCl$_3$) δ: 4.63 (2H, d, J=5.2 Hz), 5.13 (2H, s), 5.32 (2H, s), 6.43-6.44 (1H, m), 6.58-6.60 (1H, m), 6.98-7.04 (3H, m), 7.13-7.14 (1H, m), 7.28-7.39 (6H, m), 7.65-7.67 (2H, m), 8.56 (1H, s), 10.58 (1H, brs).

Compound 17-31

9-Benzyloxy-2-(3-dimethylamino-2,2-dimethyl-propyl)-1,8-dioxo-1,8-dihydro-2H-pyrid[1,2-a]pyrazine-7-carboxylic acid 4-fluoro-benzylamide NMR (CDCl$_3$) δ: 0.99 (6H, brs), 1.62 (1H, brs), 2.22 (1H, brs), 2.33 (6H, brs), 3.83 (2H, brs), 4.62 (2H, d, J=6.0 Hz), 5.29 (2H, s), 6.56 (1H, d, J=6.3 Hz), 6.64 (1H, brs), 7.01 (2H, t, J=8.1 Hz), 7.27-7.36 (5H, m), 7.62 (2H, d, J=8.1 Hz), 8.57 (1H, s), 10.62 (1H, t, J=5.7 Hz).

Compound 17-32

9-Benzyloxy-2-(3-morpholin-4-yl-propyl)-1,8-dioxo-1,8-dihydro-2H-pyrid[1,2-a]pyrazine-7-carboxylic acid 4-fluoro-benzylamide NMR (CDCl$_3$) δ: 1.92 (2H, tt, J=6.6 Hz, 6.9 Hz), 2.39 (2H, t, J=, 6.6 Hz), 2.43 (4H, brt, J=4.8 Hz), 3.70 (4H, brt, J=4.8 Hz), 3.86 (2H, t, J=6.9 Hz), 4.62 (2H, d, J=6.0 Hz), 5.28 (2H, s), 6.50 (1H, d, J=6.3 Hz), 6.61 (1H, d, J=6.3 Hz), 7.01 (2H, m), 7.29-7.38 (5H, m), 7.62-7.65 (2H, m), 8.60 (1H, s), 10.62 (1H, brt, J=6.0 Hz).

16) To the compound 17-1 (140 mg, 0.293 mmol) was added trifluoroacetic acid (1.4 ml) under ice-cooling, and the mixture was stirred at 0° C. for 5 minutes and, then, at room temperature for 1.5 hours. The solvent was distilled off under reduced pressure, and this was diluted with chloroform, and added to ice water. This was washed with an aqueous saturated sodium bicarbonate solution, a 10% aqueous citric acid solution and water, and dried with anhydrous sodium sulfate. The solvent was distilled off under reduced pressure, and the residue was recrystallized with methylene chloride-ethanol to obtain Example A-1 (89 mg, 79%) as a yellow crystal.

melting point: 223-224° C.

NMR (DMSO-$d_6$) δ: 3.25 (3H, s), 3.58 (2H, t, J=5.4 Hz), 3.92 (2H, t, J=5.1 Hz), 4.53 (2H, d, J=5.7 Hz), 6.87 (1H, d, 6.3 Hz), 7.14 (2H, t, J=9.0 Hz), 7.33-7.38 (2H, m), 7.47 (1H, d, J=6.0 Hz), 8.77 (1H, s), 10.56 (1H, t, J=6.0 Hz), 12.00 (1H, brs).

17) The compound 17-1 (157 mg, 0.329 mmol) was dissolved in dimethylformamide (18 ml) and methanol (1 ml), 10% palladium-carbon powder (31 mg) was added, and the mixture was stirred at room temperature for 20 hours under the hydrogen atmosphere. The reaction solution was filtered with Celite, and the filtrate was concentrated under reduced pressure. The residue was dissolved in chloroform, this was filtered with Celite again, and the filtrate was concentrated under reduced pressure. The residue was recrystallized with methylene chloride-methanol to obtain Example B-1 (66 mg, 52%) as a brown crystal.

melting point: 197-199° C.

NMR (DMSO-$d_6$) δ: 3.27 (3H, s), 3.55 (2H, t, J=5.1 Hz), 3.68 (2H, t, J=5.1 Hz), 3.79 (2H, s), 4.36 (2H, s), 4.51 (2H, d, J=5.7 Hz), 7.15 (2H, t, J=8.7 Hz), 7.32-7.37 (2H, m), 8.38 (1H, s), 10.46 (1H, t, J=5.4 Hz), 12.41 (1H, s).

According to the same manner as that of Example A-1, the following Example compounds A-2 to A-29, and A-31 to A-32 were synthesized.

Example A-2

2-(2-Dimethylamino-ethyl)-9-hydroxy-1,8-dioxo-1, 8-dihydro-2H-pyrid[1,2-a]pyrazine-7-carboxylic acid 4-fluoro-benzylamide melting point: 224-225° C.

NMR (DMSO-$d_6$) δ: 2.24 (6H, s), 2.59 (2H, t, J=6.0 Hz), 3.87 (2H, t, J=6.0 Hz), 4.55 (2H, d, J=6.0 Hz), 6.94 (1H, d, J=6.3 Hz), 7.17 (2H, t, J=6.9 Hz), 7.35-7.40 (2H, m), 7.50 (1H, d, J=6.3 Hz), 8.80 (1H, s), 10.59 (1H, t, J=6.0 Hz), 12.05 (1H, s).

Example A-3

9-Hydroxy-2-(2-morpholin-4-yl-ethyl)-1,8-dioxo-1, 8-dihydro-2H-pyrid[1,2-a]pyrazine-7-carboxylic acid 4-fluoro-benzylamide melting point: 212-215° C.

NMR (DMSO-$d_6$) δ: 2.51 (4H, s), 2.38 (3H, s), 3.55 (4H, s), 3.90 (2H, s), 4.55 (2H, d, J=6.0 Hz), 6.95 (1H, d, J=6.3 Hz), 7.17 (2H, t, J=8.7 Hz), 7.35-7.40 (2H, m), 7.50 (1H, d, J=6.3 Hz), 10.58 (1H, t, J=6.3 Hz), 12.10 (1H, s).

Example A-4

9-Hydroxy-1,8-dioxo-2-(2-piperidin-1-yl-ethyl)-1,8-dihydro-2H-pyrid[1,2-a]pyrazine-7-carboxylic acid 4-fluoro-benzylamide melting point: 217-218° C.
Elementary analysis for $C_{23}H_{25}FN_4O_4$
Cal'd (%): C, 62.72; H, 5.72; F, 4.31; N, 12.72.
Found (%): C, 58.98; H, 5.46; F, 6.16; N, 11.66.
NMR (DMSO-$d_6$) δ: 1.41-1.51 (6H, m), 2.49-2.73 (6H, m), 3.91 (2H, m), 4.54 (2H, d, J=6 Hz), 6.93 (1H, d, J=6 Hz), 7.13-7.19 (2H, m), 7.35-7.39 (2H, m), 7.50 (1H, d, J=6 Hz), 8.80 (1H, s), 10.57 (1H, t, J=5.7 Hz), 12.14 (1H, brs).

Example A-5

9-Hydroxy-2-(2-methyl-butyl)-1,8-dioxo-1,8-dihydro-2H-pyrid[1,2-a]pyrazine-7-carboxylic acid 4-fluoro-benzylamide melting point: 242-243° C.
Elementary analysis for $C_{21}H_{22}FN_3O_4$
Cal'd (%): C, 63.15; H, 5.55; F, 4.76; N, 10.52.
Found (%): C, 63.14; H, 5.57; F, 4.63; N, 10.54.
NMR (DMSO-$d_6$) δ: 0.86-0.94 (6H, m), 1.08-1.20 (1H, m), 1.33-1.55 (1H, m), 1.81-1.90 (1H, m), 3.51-3.58 (1H, m), 3.65-3.71 (1H, m), 4.54 (2H, d, J=6 Hz), 6.92 (1H, d, J=6.3 Hz), 7.13-7.20 (2H, m), 7.34-7.39 (2H, m), 7.50 (1H, d, J=6.3 Hz), 8.79 (1H, s), 10.60 (1H, t, J=5.7 Hz), 12.13 (1H, brs).

Example A-6

9-Hydroxy-2-(2-isopropoxy-ethyl)-1,8-dioxo-1,8-dihydro-2H-pyrid[1,2-a]pyrazine-7-carboxylic acid 4-fluoro-benzylamide melting point: 209-210° C.
Elementary analysis for $C_{21}H_{22}FN_3O_5$
Cal'd (%): C, 60.72; H, 5.34; F, 4.57; N, 10.12.
Found (%): C, 60.78; H, 5.29; F, 4.34; N, 10.11.
NMR (DMSO-$d_6$) δ: 1.06 (6H, d, J=6.3 Hz), 3.54-3.64 (3H, m), 3.90 (2H, t, J=5.4 Hz), 6.89 (1H, d, J=6.3 Hz), 7.13-7.19 (2H, m), 7.35-7.39 (2H, m), 7.47 (1H, d, J=6.3 Hz), 8.77 (1H, s), 10.58 (1H, t, J=5.7 Hz), 12.04 (1H, brs).

Example A-7

9-Hydroxy-2-isopropyl-1,8-dioxo-1,8-dihydro-2H-pyrid[1,2-a]pyrazine-7-carboxylic acid 4-fluoro-benzylamide melting point: 282-283° C.
NMR (DMSO-$d_6$) δ: 1.29 (6H, d, J=6.9 Hz), 4.54 (2H, d, J=5.9 Hz), 4.83-4.92 (1H, m), 7.04 (1H, d, J=6.4 Hz), 7.13-7.19 (2H, m), 7.35-7.40 (2H, m), 7.56 (1H, d, J=6.4 Hz), 8.80 (1H, s), 10.61 (1H, t, J=5.8 Hz), 12.26 (1H, brs).

Example A-8

2-Cyclohexyl-9-hydroxy-1,8-dioxo-1,8-dihydro-2H-pyrid[1,2-a]pyrazine-7-carboxylic acid 4-fluoro-benzylamide melting point: >300° C.
NMR (DMSO-$d_6$) δ: 1.15-1.84 (10H, m), 4.43-4.49 (1H, m), 4.53 (2H, d, J=5.8 Hz), 7.05 (1H, d, J=6.4 Hz), 7.13-7.19

(2H, m), 7.34-7.39 (2H, m), 7.53 (1H, d, J=6.4 Hz), 8.79 (1H, s), 10.61 (1H, t, J=5.8 Hz), 12.23 (1H, brs).

Example A-9

9-Hydroxy-1,8-dioxo-2-[2-(propyl-m-toluoyl-amino)-ethyl]-1,8-dihydro-2H-pyrid[1,2-a]pyrazine-7-carboxylic acid 4-fluoro-benzylamide melting point: 190-192° C.
NMR (CDCl$_3$) δ: 1.10-1.16 (3H, m), 2.29 (3H, s), 3.29-3.38 (2H, m), 3.63-3.69 (2H, m), 3.94-3.99 (2H, m), 4.62 (2H, d, J=6.0 Hz), 6.13-6.19 (1H, m), 6.52-6.61 (4H, m), 6.96-7.40 (2H, m), 6.96-7.04 (2H, m), 7.04-7.17 (1H, m), 7.29-7.36 (2H, m), 8.47 (1H, s), 10.56 (1H, brs), 11.89 (1H, brs).

Example A-10

9-Hydroxy-1,8-dioxo-2-[3-(2-oxo-pyrrolidin-1-yl)-propyl]-1,8-dihydro-2H-pyrid[1,2-a]pyrazine-7-carboxylic acid 4-fluoro-benzylamide melting point: 262-264° C.
NMR (CDCl$_3$) δ: 1.93-2.04 (2H, m), 2.04-2.15 (2H, m), 2.39-2.46 (2H, m), 3.35-3.46 (4H, m), 3.75-3.81 (2H, m), 4.62 (2H, d, J=5.7 Hz), 6.69 (1H, d, J=6.3 Hz), 6.78 (1H, d, J=6.3 Hz), 6.95-7.04 (2H, m), 7.29-7.37 (2H, m), 8.53 (1H, s), 10.58 (1H, brs), 11.89 (1H, brs).

Example A-11

9-Hydroxy-1,8-dioxo-2-(2-tetrahydrofuran-2-ylmethyl)-1,8-dihydro-2H-pyrid[1,2-a]pyrazine-7-carboxylic acid 4-fluoro-benzylamide melting point: 248-249° C.
NMR (CDCl$_3$) δ: 1.52-1.66 (1H, m), 1.90-2.00 (2H, m), 2.06-2.18 (1H, m), 3.52-3.61 (1H, m), 3.71-3.83 (1H, m), 3.85-3.94 (1H, m), 4.12-4.24 (1H, m), 4.63 (2H, d, J=6.0 Hz), 6.59 (1H, d, J=6.5 Hz), 6.66 (1H, d, J=6.5 Hz), 6.96-7.04 (2H, m), 7.29-7.37 (2H, m), 8.52 (1H, s), 10.61 (1H, brs), 11.97 (1H, brs).

Example A-12

9-Hydroxy-1,8-dioxo-2-pyridin-4-ylmethyl-1,8-dihydro-2H-pyrid[1,2-a]pyrazine-7-carboxylic acid 4-fluoro-benzylamide melting point: 265-268° C.
NMR (DMSO-d$_6$) δ: 4.55 (2H, d, J=5.4 Hz), 5.02 (2H, s), 7.02 (1H, d, J=6.5 Hz), 7.13-7.22 (2H, m), 7.34-7.42 (4H, m), 7.56 (1H, d, J=6.51 Hz), 8.54-8.57 (2H, m), 8.83 (1H, s), 10.54-10.56 (1H, m), 11.78 (1H, s).

Example A-13

4-[7-(4-Fluoro-benzylcarbamoyl)-9-hydroxy-1,8-dioxo-1,8-dihydro-pyrid[1,2-a]pyrazin-2-yl]-piperidine-1-carboxylic acid ethyl ester melting point: 288-289° C.
NMR (CDCl$_3$) δ: 1.29 (3H, t, J=7.0 Hz), 1.64-1.75 (2H, m), 1.86-1.92 (2H, m), 2.89-2.97 (2H, m), 4.16 (2H, q, J=7.0 Hz), 4.30-4.50 (2H, m), 4.62 (2H, d, J=5.8 Hz), 4.80-4.88 (1H, m), 6.33 (1H, d, J=6.6 Hz), 6.76 (1H, d, J=6.6 Hz), 6.97-7.03 (2H, m), 7.31-7.35 (2H, m), 8.56 (1H, s), 10.57 (1H, brs), 11.98 (1H, brs).

Example A-14

9-Hydroxy-2-methyl-1,8-dioxo-1,8-dihydro-2H-pyrid[1,2-a]pyrazine-7-carboxylic acid 4-fluoro-benzylamide melting point: 276-279° C.
NMR (CDCl$_3$) δ: 3.43 (3H, s), 4.63 (2H, d, J=5.7 Hz), 6.33 (1H, d, J=6.2 Hz), 6.71 (1H, d, J=6.2 Hz), 6.86-7.05 (2H, m), 7.30-7.37 (2H, m), 8.53 (1H, s), 10.59 (1H, brs), 11.95 (1H, brs).

Example A-15

2-(2-Acetylamino-ethyl)-9-hydroxy-1,8-dioxo-1,8-dihydro-2H-pyrid[1,2-a]pyrazine-7-carboxylic acid 4-fluoro-benzylamide melting point: >300° C.
NMR (DMSO-d$_6$) δ: 1.76 (3H, s), 3.37 (2H, t, J=5.7 Hz), 3.79 (2H, t, J=5.7 Hz), 4.54 (2H, d, J=5.7 Hz), 6.85 (1H, d, J=6.3 Hz), 7.16 (2H, m), 7.37 (2H, m), 7.48 (1H, d, J=6.3 Hz), 7.95 (1H, brt, J=5.7 Hz), 8.82 (1H, s), 10.58 (1H, brt, J=5.7 Hz), 12.07 (1H, s).

Example A-16

9-Hydroxy-2-(3-isopropoxy-propyl)-1,8-dioxo-1,8-dihydro-2H-pyrid[1,2-a]pyrazine-7-carboxylic acid 4-fluoro-benzylamide melting point: 180-181° C.
NMR (CDCl$_3$) δ: 1.14 (6H, d, J=6.1 Hz), 1.94-2.04 (2H, m), 3.48 (2H, t, J=5.7 Hz), 3.55 (1H, sep, J=6.1 Hz), 3.92 (2H, t, J=6.6 Hz), 4.63 (2H, d, J=6.0 Hz), 6.42 (1H, d, J=6.2 Hz), 6.67 (1H, d, J=6.2 Hz), 6.96-7.04 (2H, m), 7.30-7.37 (2H, m), 8.52 (1H, s), 10.61 (1H, brs), 12.05 (1H, brs).

Example A-17

2-(4-Dimethylamino-benzyl)-9-hydroxy-1,8-dioxo-1,8-dihydro-2H-pyrid[1,2-a]pyrazine-7-carboxylic acid 4-fluoro-benzylamide melting point: 245-247° C.
NMR (CDCl$_3$) δ: 2.98 (6H, s), 4.62 (2H, d, J=5.7 Hz), 4.87 (2H, s), 6.32 (1H, d, J=6.2 Hz), 6.63 (1H, d, J=6.2 Hz), 6.79 (2H, brs), 6.96-7.23 (2H, m), 7.21-7.25 (2H, m), 7.30-7.36 (2H, m), 8.49 (1H, s), 10.61 (1H, t, J=5.7 Hz), 12.08 (1H, brs).

Example A-18

9-Hydroxy-2-(3-methoxy-propyl)-1,8-dioxo-1,8-dihydro-2H-pyrid[1,2-a]pyrazine-7-carboxylic acid 4-fluoro-benzylamide melting point: 197-199° C.
NMR (CDCl$_3$) δ: 1.96-2.04 (2H, m), 3.34 (3H, s), 3.45 (2H, t, J=5.4 Hz), 3.90 (2H, t, J=6.9 Hz), 4.62 (2H, d, J=5.7 Hz), 5.11 (2H, s), 6.38 (1H, d, J=6.0 Hz), 6.70 (1H, d, J=6.0 Hz), 6.97-7.03 (2H, m), 7.31-7.35 (2H, m), 8.55 (1H, s), 10.61 (1H, brs), 12.03 (1H, brs).

Example A-19

9-Hydroxy-1,8-dioxo-2-(2-propoxy-ethyl)-1,8-dihydro-2H-pyrid[1,2-a]pyrazine-7-carboxylic acid 4-fluoro-benzylamide melting point: 215-217° C.
NMR (CDCl$_3$) δ: 0.90 (3H, t, J=7.5 Hz), 1.58 (2H, m), 3.41 (2H, t, J=6.6 Hz), 3.69 (2H, t, J=4.7 Hz), 3.97 (2H, t, J=4.6 Hz), 4.63 (2H, d, J=5.8 Hz), 6.53 (1H, d, J=6.3 Hz), 6.67 (1H, d, J=6.3 Hz), 6.97-7.03 (2H, m), 7.31-7.36 (2H, m), 8.54 (1H, s), 10.62 (1H, brs), 11.97 (1H, brs).

Example A-20

9-Hydroxy-1,8-dioxo-2-(2-phenoxy-ethyl)-1,8-dihydro-2H-pyrid[1,2-a]pyrazine-7-carboxylic acid 4-fluoro-benzylamide melting point: 237-239° C.
NMR (CDCl$_3$) δ: 4.18-4.21 (2H, m), 4.26-4.29 (2H, m), 4.62 (2H, d, J=5.8 Hz), 6.57 (1H, d, J=6.3 Hz), 6.71 (1H, d, J=6.3 Hz), 6.86 (2H, d, J=8.1 Hz), 6.97-7.02 (3H, m), 7.29-7.35 (4H, m), 8.56 (1H, s), 10.58 (1H, t, J=5.7 Hz), 11.84 (1H, brs).

Example A-21

9-Hydroxy-1,8-dioxo-2-(2-pyridin-3-yl-ethyl)-1,8-dihydro-2H-pyrid[1,2-a]pyrazine-7-carboxylic acid 4-fluoro-benzylamide melting point: 256-257° C.
NMR (CDCl$_3$) δ: 3.00 (2H, t, J=7.5 Hz), 4.02 (2H, t, J=7.5 Hz), 4.54 (2H, d, J=6.0 Hz), 6.89 (1H, d, J=6.3 Hz), 7.16 (2H, m), 7.30-7.39 (3H, m), 7.48 (1H, d, J=6.3 Hz), 7.70 (1H, m), 8.44 (1H, dd, J=1.8 Hz, 5.1 Hz), 8.48 (1H, m), 8.78 (1H, s), 10.56 (1H, t, J=6.0 Hz), 11.98 (1H, s).

Example A-22

2-Dimethylcarbamoylmethyl-9-hydroxy-1,8-dioxo-1,8-dihydro-2H-pyrid[1,2-a]pyrazine-7-carboxylic acid 4-fluoro-benzylamide melting point: >300° C.
NMR (DMSO-d$_6$) δ: 2.87 (3H, s), 3.03 (3H, s), 4.55 (2H, d, J=6.0 Hz), 4.71 (2H, s), 6.80 (1H, d, J=6.3 Hz), 7.16 (2H, m), 7.38 (2H, m), 7.48 (1H, d, J=6.3 Hz), 8.82 (1H, s), 10.54 (1H, brt, J=6.0 Hz), 11.83 (1H, s).

Example A-23

2-(2-Ethoxy-ethyl)-9-hydroxy-1,8-dioxo-1,8-dihydro-2H-pyrid[1,2-a]pyrazine-7-carboxylic acid 4-fluoro-benzylamide melting point: 212-214° C.
NMR (CDCl$_3$) δ: 1.19 (3H, t, J=7.0 Hz), 3.51 (2H, q, J=7.0 Hz), 3.67-3.72 (2H, m), 3.95-4.01 (2H, m), 4.63 (2H, d, J=5.7 Hz), 6.54 (1H, d, J=6.0 Hz), 6.65 (1H, d, J=6.0 Hz), 6.96-7.02 (2H, m), 7.29-7.36 (2H, m), 8.52 (1H, s), 10.62 (1H, brs), 11.97 (1H, brs).

Example A-24

2-Furan-2-ylmethyl-9-hydroxy-1,8-dioxo-1,8-dihydro-2H-pyrid[1,2-a]pyrazine-7-carboxylic acid 4-fluoro-benzylamide melting point: 234-237° C.
NMR (DMSO-d$_6$) δ: 4.54 (2H, d, J=6.0 Hz), 4.98 (2H, s), 6.45 (1H, dd, J=2.1 Hz, 3.3 Hz), 6.53 (1H, dd, J=0.6 Hz, 3.3 Hz), 6.93 (1H, d, J=6.3 Hz), 7.16 (2H, m), 7.36 (2H, m), 7.47 (1H, d, J=6.3 Hz), 7.65 (1H, dd, J=0.6 Hz, 2.1 Hz), 8.74 (1H, s), 10.56 (1H, brt, J=6.0 Hz), 11.85 (1H, s).

Example A-25

2-[2-(4-Chloro-phenyl)-ethyl]-9-hydroxy-1,8-dioxo-1,8-dihydro-2H-pyrid[1,2-a]pyrazine-7-carboxylic acid 4-fluoro-benzylamide melting point: 288-291° C.
NMR (DMSO-d$_6$) δ: 2.96 (2H, t, J=7.5 Hz), 2.98 (2H, t, J=7.5 Hz), 4.54 (2H, d, J=6.0 Hz), 6.87 (1H, d, J=6.3 Hz), 7.16 (2H, m), 7.30 (2H, m), 7.34-7.39 (4H, m), 7.47 (1H, d, J=6.3 Hz), 8.78 (1H, s), 10.57 (1H, brt, J=6.0 Hz), 12.01 (1H, s).

Example A-26

2-(1-Benzyl-pyrrolidin-3-yl)-9-hydroxy-1,8-dioxo-1,8-dihydro-2H-pyrid[1,2-a]pyrazine-7-carboxylic acid 4-fluoro-benzylamide melting point: 218-219° C.
NMR (CDCl$_3$) δ: 1.82 (1H, m), 2.24 (1H, q, J=8.4 Hz), 2.36 (1H, m), 2.56 (1H, m), 2.83 (1H, m), 3.00 (1H, m), 3.63 (2H, s), 4.54 (2H, d, J=6.0 Hz), 5.19 (1H, m), 7.11 (1H, d, J=6.3 Hz), 7.16 (2H, m), 7.23-7.39 (7H, m), 7.56 (1H, d, J=6.3 Hz), 8.78 (1H, s), 10.58 (1H, t, J=6.0 Hz), 12.14 (1H, s).

Example A-27

9-Hydroxy-1,8-dioxo-2-thiophen-2-ylmethyl-1,8-dihydro-2H-pyrid[1,2-a]pyrazine-7-carboxylic acid 4-fluoro-benzylamide melting point: 233-236° C.
NMR (CDCl$_3$) δ: 4.61 (2H, d, J=6.0 Hz), 5.11 (2H, s), 6.37 (1H, d, J=6.3 Hz), 6.72 (1H, d, J=6.3 Hz), 6.96-7.04 (3H, m), 7.15 (1H, d, J=3.3 Hz), 7.32-7.36 (3H, m), 8.56 (1H, s), 10.56 (1H, brs), 11.87 (1H, brs).

Example A-28

2-(3-Dimethylamino-2,2-dimethyl-propyl)-9-hydroxy-1,8-dioxo-1,8-dihydro-2H-pyrid[1,2-a]pyrazine-7-carboxylic acid 4-fluoro-benzylamide melting point: 208-210° C.
NMR (DMSO-d$_6$) δ: 0.91 (6H, s), 2.17 (2H, s), 2.25 (6H, s), 3.70 (2H, s), 4.54 (2H, d, J=5.7 Hz), 6.84 (1H, d, J=6.0 Hz), 7.14-7.19 (2H, m), 7.35-7.39 (2H, m), 7.46 (1H, d, J=6.0 Hz), 8.81 (1H, s), 10.60 (1H, t, J=6.3 Hz), 12.18 (1H, brs).

Example A-29
9-Hydroxy-2-(3-morpholin-4-yl-propyl)-1,8-dioxo-1,8-dihydro-2H-pyrid[1,2-a]pyrazine-7-carboxylic acid 4-fluoro-benzylamide
melting point: 197-198° C.
NMR (CDCl$_3$) δ: 1.81 (2H, tt, J=6.3 Hz, 6.9 Hz), 2.31 (4H, brs), 2.33 (2H, t, J=6.3 Hz), 3.49 (4H, brt, J=4.5 Hz), 3.80 (2H, t, J=6.9 Hz), 4.54 (2H, d, J=6.0 Hz), 6.95 (1H, d, J=6.3 Hz), 7.16 (2H, m), 7.34 (2H, m), 7.50 (1H, d, J=6.3 Hz), 8.80 (1H, s), 10.59 (1H, t, J=6.0 Hz), 12.16 (1H, s).
Example A-30
2-(4-Fluorobenzyl)-9-hydroxy-1,8-dioxo-1,8-dihydro-2H-pyrid[1,2-a]pyrazine-7-carboxylic acid 4-fluoro-benzylamide
[Chemical formula 53]
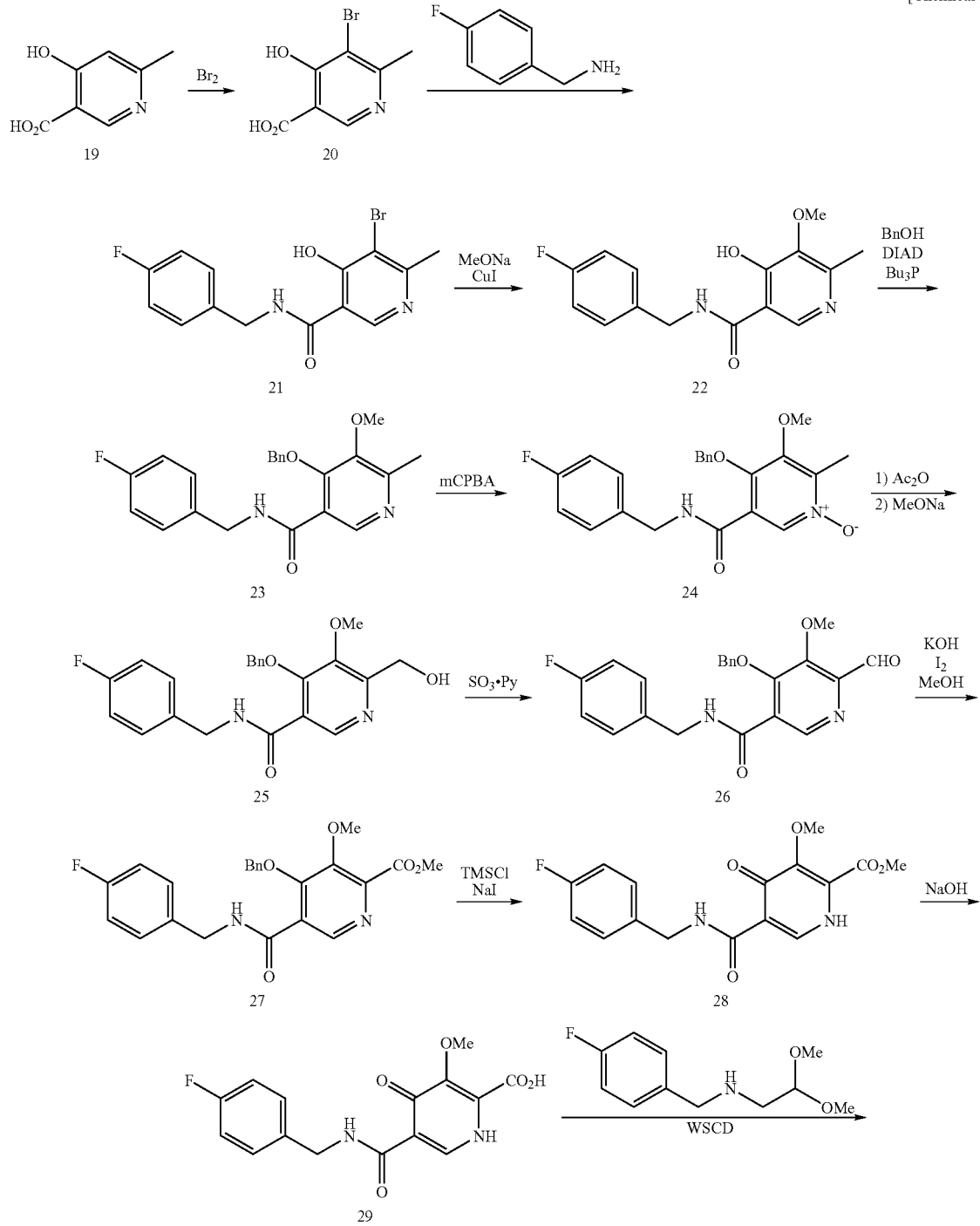

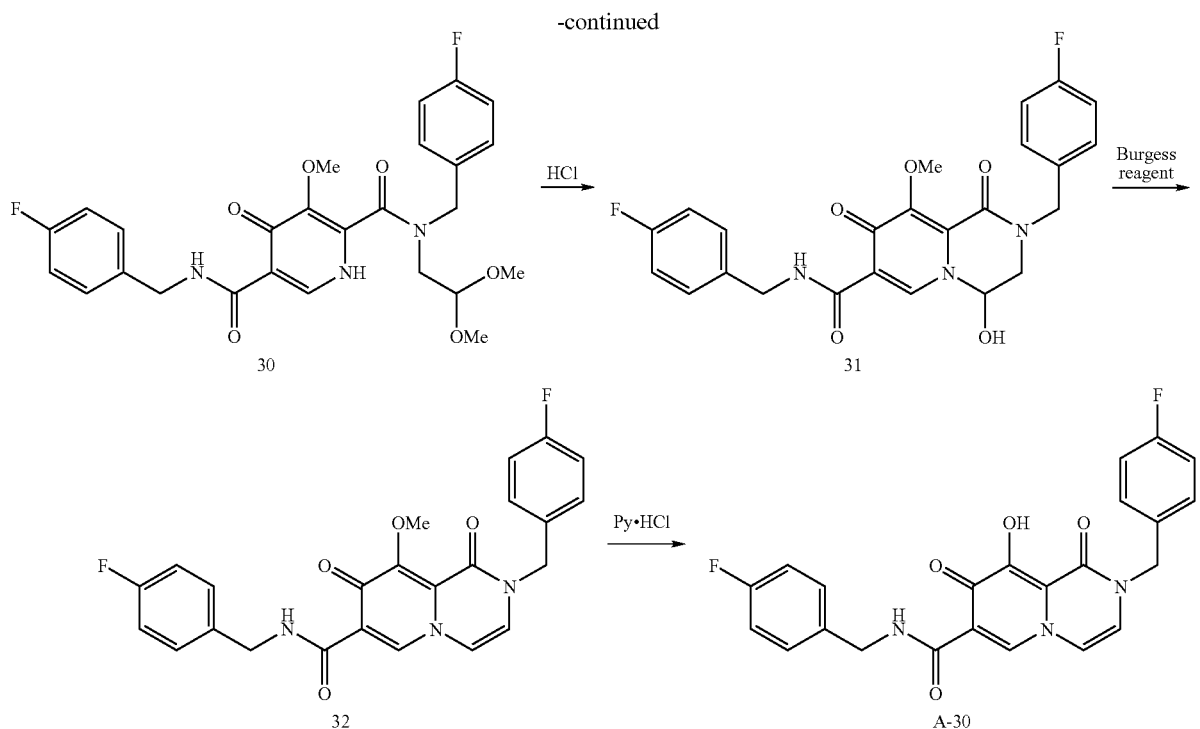

1) 4-Hydroxy-6-methylnicotinic acid 19 (95.6 g, 0.625 mol) was dissolved in acetic acid (950 ml) and water (190 ml), and bromine (39 ml, 0.750 mol) was added over 15 minutes. After the solution was stirred at 60° C. for 5 hours, the solvent was distilled off under reduced pressure, methanol (200 ml) was added and, crystals were collected by filtration. The solution was distilled off under reduced pressure, methanol was added again to the residue, and crystals were collected by filtration. A total of 142.2 g (98%) of 5-bromo-4-hydroxy-6-methylnicotinic acid 20 was obtained as a colorless crystal.

NMR (DMSO-$d_6$) δ: 2.53 (3H, s), 8.56 (1H, s), 13.45 (1H, brs), 14.80 (1H, brs).

2) The compound 20 (138 g, 0.596 mol), 1-ethyl-3-(3-dimethylaminopropyl)carbodiimide hydrochloride (148 g, 0.775 mol), and 1-hydroxybenzotriazole (100 g, 0.656 mol) were dissolved in methylformamide (970 ml), and 4-fluorobenzylamine (79 ml, 0.715 mol) was added. After the reaction solution was stirred at room temperature for 9 hours, water (2000 ml) was added, and crystals were collected by filtration, followed by washing with ether. 5-Bromo-N-(4-fluorobenzyl)-4-hydroxy-6-methylnicotinamide 21 (156 g, 77%) was obtained as a colorless crystal.

NMR (DMSO-$d_6$) δ: 2.47 (3H, s), 4.50 (2H, d, J=5.9 Hz), 7.12-7.20 (m, 2H), 7.32-7.39 (m, 2H), 8.38 (1H, s), 10.50 (1H, t, J=5.9 Hz), 12.72 (1H, brs).

3) The compound 21 (75.2 g, 222 mmol) and copper (I) iodide (21.1 g, 111 mmol) were dissolved in dimethylformamide (750 ml), a 28% sodium methoxide-methanol solution (216 ml, 888 mmol) was added, and the mixture was stirred at 105° C. for 100 minutes. After cooling, ice-water (800 ml) was added, and unnecessary matter were filtered. To the solution was added 2M hydrochloric acid (443 ml), and crystals were collected by filtration. N-(4-fluorobenzyl)-4-hydroxy-5-methoxy-6-methylnicotinamide 22 (56.0 g, 870%) was obtained as a colorless crystal.

NMR (DMSO-$d_6$) δ: 2.26 (3H, s), 3.74 (3H, s), 4.49 (2H, d, J=6.0 Hz), 7.10-7.19 (2H, m), 7.30-7.38 (2H, m), 8.24 (1H, s), 10.68 (1H, t, J=6.0 Hz), 12.21 (1H, brs).

4) To a solution of the compound 22 (100 g, 344 mmol), benzyl alcohol (46 ml, 447 mmol), and tributylphosphine (128 ml, 516 mmol) in tetrahydrofuran (1000 ml) was added a 40% diisopropyl azodicarboxylate-toluene solution (280 ml, 516 mmol) under ice-cooling over 30 minutes. After stirred for 30 minutes under ice-cooling, a temperature was raised to room temperature, followed by stirring for 2 hours. The solvent was distilled off under reduced pressure, to the residue were added toluene (100 ml) and hexane (2000 ml), and precipitated crystals were filtered. The solvent was distilled off under reduced pressure, to the residue were added diethyl ether (200 ml) and hexane (2000 ml), and precipitated crystals were filtered. The solvent was distilled off under reduced pressure, and the residue was purified by silica gel column chromatography (hexane/ethyl acetate). 4-Benzyloxy-N-(4-fluorobenzyl)-5-methoxy-6-methylnicotinamide 23 (68.5 g, 52%) was obtained as a colorless crystal.

NMR (CDCl$_3$) δ: 2.58 (3H, s), 3.86 (3H, s), 4.40 (2H, d, J=5.7 Hz), 5.21 (2H, s), 6.91-7.00 (2H, m), 7.08-7.14 (2H, m), 7.19-7.27 (2H, m), 7.32-7.40 (3H, m), 7.87 (1H, brs), 8.97 (1H, s).

5) To a solution of the compound 23 (67.5 g, 177 mmol) in chloroform (350 ml) was added a solution of metachloroperbenzoic acid (65%) (49.5 g, 186 mmol) in chloroform (350 ml) over 30 minutes under ice-cooling. After stirred for 45 minutes under ice-cooling, a temperature was raised to room temperature, followed by stirring for 75 minutes. To the reaction solution was added an aqueous saturated sodium bicarbonate solution, followed by extraction with chloroform. The organic layer was washed with an aqueous saturated sodium bicarbonate solution, and dried with anhydrous sodium sulfate. The solvent was distilled off under reduced pressure, to the residue was added diethyl ether (200 ml), and precipitated crystals (47.8 g) were collected by filtration. The solvent was distilled off under reduced pressure, and the residue was purified by silica gel column chromatography (toluene/acetone) to obtain 2.65 g of crystals. A total of 50.5 g (72%) of 4-benzyloxy-N-(4-fluorobenzyl)-5-methoxy-6-methyl-1-oxynicotinamide 24 was obtained as a colorless crystal.

NMR (CDCl$_3$) δ: 2.55 (3H, s), 3.90 (3H, s), 4.40 (2H, d, J=5.7 Hz), 5.16 (2H, s), 6.93-6.70 (2H, s), 6.90-7.19 (5H, m), 7.30-7.38 (2H, m), 7.94 (1H, brs), 8.81 (1H, s).

6) The compound 24 (49.4 g, 125 mmol) was dissolved in acetic anhydride (350 ml), and this was stirred at 80° C. for 30 minutes. The solvent was distilled off under reduced pressure, this was dissolved in methanol (500 ml), and a 28% sodium methoxide-methanol solution (7.5 ml, 31.3 mmol) was added under ice-cooling, followed by stirring at room temperature for 1 hour. To the reaction solution was added Amberlite (registered trade mark) IR-120B until the solution became neutral, and a solid matter was filtered. The solvent was distilled off under reduced pressure, and the residue was purified by silica gel column chromatography (hexane/ethyl acetate). 4-Benzyloxy-N-(4-fluorobenzyl)-6-hydroxymethyl-5-methoxynicotinamide 25 (25.4 g, 51%) was obtained as a colorless crystal.

NMR (CDCl$_3$) δ: 3.42 (1H, brs), 3.89 (3H, s), 4.41 (2H, d, J=5.7 Hz), 4.83 (2H, s), 5.23 (2H, s), 6.92-6.99 (2H, m), 7.09-7.14 (2H, m), 7.19-7.23 (2H, m), 7.28-7.37 (3H, m), 7.85 (1H, brs), 9.03 (1H, s).

7) To a solution of the compound 25 (25.0 g, 63.1 mmol), dimethyl sulfoxide (44.8 ml, 631 mmol), and triethylamine (44.3 ml, 378 mmol) in chloroform (250 ml) was added a sulfur trioxide pyridine complex (50.2 g, 315 mmol) under ice-cooling, and the mixture was stirred at room temperature for 20 minutes. To the reaction solution was added water, chroloform was distilled off under reduced pressure, and the residue was extracted with ethyl acetate. The extract was washed with water, and dried with anhydrous sodium sulfate. The solvent was distilled off under reduced pressure, to the residue was added diethyl ether, and crystals (17.7 g) were collected by filtration. The solvent was distilled off under reduced pressure, and the residue was purified by silica gel column chromatography to obtain 3.16 g of crystals. A total of 20.9 g (84%) of 4-benzyloxy-N-(4-fluorobenzyl)-6-formyl-5-methoxynicotinamide 26 was obtained as a colorless crystal.

NMR (CDCl$_3$) δ: 4.02 (3H, s), 4.41 (2H, d, J=5.7 Hz), 5.30 (2H, s), 6.93-6.70 (2H, m), 7.09-7.15 (2H, m), 7.20-7.27 (2H, m), 7.31-7.40 (3H, m), 7.83 (1H, brs), 9.20 (1H, s), 10.26 (1H, s).

8) To a solution of the compound 26 (300 mg, 0.761 mmol) in methanol (1 ml) was added a solution of potassium hydroxide (111 mg, 1.99 mmol) in methanol (1 ml) under ice-cooling, and a solution of iodine (251 mg, 1.00 mmol) in methanol (4 ml) was further added, followed by stirring at the same temperature for 1 hour. To the reaction solution were added a 5% aqueous sodium hydrogen sulfite solution and water, and precipitated crystals were collected by filtration. Methyl 4-benzyloxy-5-(4-fluorobenzylcarbamoyl)-3-methoxypyridine-2-carboxylate 27 (275 mg, 85%) was obtained as a colorless crystal.

NMR (CDCl$_3$) δ: 3.99 (3H, s), 4.02 (3H, s), 7.40 (2H, d, J=5.7 Hz), 5.26 (2H, s), 6.92-6.99 (2H, m), 7.10-7.15 (2H, m), 7.19-7.23 (2H, m), 7.25-7.39 (3H, m), 7.81 (1H, brs), 9.09 (1H, s).

9) To a suspension of sodium iodide (5.51 g, 36.8 mmol) in acetonitrile (50 ml) was added chlorotrimethylsilane (4.66 ml, 36.8 mmol), and the mixture was stirred at room temperature for 10 minutes. After to this solution was added the compound 27 (2.60 g, 6.13 mmol) under ice-cooling, this was stirred at the same temperature for 20 minutes. To the reaction solution was added a 5% sodium hydrogen sulfite solution, followed by extraction with ethyl acetate. The extract was washed with an aqueous saturated sodium bicarbonate solution and an aqueous saturated sodium chlorite solution, and dried with anhydrous sodium sulfate. The solvent was distilled off under reduced pressure, and the resulting solid matter was recrystallized to obtain (acetone-diisopropyl ether) and methyl 5-(4-fluorobenzylcarbamoyl)-3-methoxy-4-oxo-1,4-dihydropyridine-2-carboxylate 28 (1.73 g, 84%) as a colorless crystal.

NMR (CDCl$_3$) δ: 4.04 (6H, s), 4.60 (2H, d, J=6.0 Hz), 6.96-7.03 (2H, m), 7.29-7.35 (2H, m), 8.63 (1H, s), 9.68 (1H, brs), 10.34 (1H, brs).

10) The compound 28 (900 mg, 2.12 mmol) was dissolved in methanol (8 ml), and a 2N aqueous sodium hydroxide solution (4 ml) was added. The solution was stirred at room temperature for 2 hours, 2M hydrochloric acid (3 ml) was added, and crystals were collected by filtration. 4-Benzyloxy-5-(4-fluoro-benzylcarbamoyl)-3-methoxy-pyridine-2-carboxylic acid 29 (474 mg, 54%) was obtained as a colorless crystal.

NMR (CDCl$_3$) δ: 4.05 (3H, s), 4.40 (2H, d, J=5.6 Hz), 5.36 (2H, s), 6.94-7.01 (2H, m), 7.08-7.12 (2H, m), 7.21-7.24 (2H, m), 7.29-7.41 (3H, m), 7.87 (1H, brs), 9.03 (1H, s).

11) From the compound 29 (641 mg, 2 mmol), a crude compound 30 (932 mg) was obtained according to the method of the step 21. To this dioxane (6 ml) solution was added 2N hydrochloric acid (3 ml) at room temperature, thereafter, this was warmed to 70° C. for 30 minutes, and cooled to room temperature, and sodium hydrogen carbonate was added. Precipitated crystals were washed with water, and dried to obtain a compound 31 (513 mg, 61%).

1H-NMR (DMSO-d$_6$) δ: 3.58 (1H, brs), 3.82 (3H, s), 3.83 (1H, brs), 4.51 (2H, d, J=6.0 Hz), 4.60 (1H, brs), 4.70 (1H, brs), 5.84 (1H, brs), 7.10-7.20 (4H, m), 7.30-7.42 (4H, m), 7.68 (1H, brs), 8.57 (1H, s), 10.41 (1H, brs).

12) To a solution of the compound 31 (513 mg, 1.1 mmol) in acetonitrile (5 ml) was added a Burgess reagent (520 mg, 2.2 mmol), and this was warmed at 70° C. for 1.5 hours. After cooled to room temperature, water was added to stop the reaction, and this was extracted with chloroform, washed with water, and dried with magnesium sulfate. The solvent was distilled off under reduced pressure, the residue was subjected to silica gel column chromatography, and fractions eluted with chloroform-methanol were concentrated under reduced pressure to obtain a compound 32 (95 mg, 19%).

1H-NMR (CDCl$_3$) δ: 4.08 (3H, s), 4.60 (2H, d, J=5.8 Hz), 4.95 (2H, s), 6.38 (1H, d, J=6.1 Hz), 6.62 (1H, d, J=6.1 Hz), 6.95-7.10 (4H, m), 7.27-7.40 (4H, m), 8.57 (1H, s), 10.54 (1H, brs).

13) To the compound 32 (95 mg, 0.2 mmol) was added pyridine hydrochloride (2 g), and this was warmed at 180° C. for 5 minutes. After cooled to room temperature, water was added, and precipitated crystals were washed with water, and dried to obtain Example A-30 (86 mg, 93%).

melting point: 290-293° C.
Elementary analysis for $C_{23}H_{17}F_2N_3O_4$
Cal'd (%): C, 63.16; H, 3.92; F, 8.69; N, 9.61.
Found (%): C, 62.97; H, 3.87; F, 8.36; N, 9.65.

1H-NMR (DMSO-d$_6$) δ: 4.54 (2H, d, J=5.6 Hz), 4.95 (2H, s), 7.02 (1H, d, J=5.6 Hz), 7.10-7.22 (4H, m), 7.30-7.57 (5H, m), 8.78 (1H, s), 10.57 (1H, t, J=5.9 Hz), 11.9 (1H, brs).

Example A-31

2-[3-(3-Chloro-5-trifluoromethyl-pyridin-2-ylamino)-propyl]-9-hydroxy-1,8-dioxo-1,8-dihydro-2H-pyrid[1,2-a]pyrazine-7-carboxylic acid 4-fluoro-benzylamide melting point: 281-283° C.
NMR (DMSO-d$_6$) δ: 1.97-2.00 (2H, m), 3.43-3.51 (2H, m), 3.83 (2H, t, J=6.8 Hz), 4.54 (2H, d, J=5.6 Hz), 6.97 (1H, d, J=6.0 Hz), 7.14-7.18 (2H, m), 7.30 (1H, t, J=5.2 Hz), 7.35-7.39 (2H, m), 7.50 (1H, d, J=6.0 Hz), 7.93 (1H, s), 8.27 (1H, s), 8.78 (1H, s), 10.58 (1H, t, J=5.6 Hz), 12.05 (1H, s).

Example A-32

2-(2-Benzyloxy-ethyl)-9-hydroxy-1,8-dioxo-1,8-dihydro-2H-pyrid[1,2-a]pyrazine-7-carboxylic acid 4-fluoro-benzylamide melting pint: 191° C.
NMR (DMSO-d$_6$) δ: 3.76 (2H, t, J=5.0 Hz), 3.98 (2H, t, J=5.2 Hz), 4.52 (2H, s), 4.63 (2H, d, J=5.8 Hz), 6.49 (1H, d, J=6.4 Hz), 6.63 (1H, d, J=6.3 Hz), 6.98-7.03 (2H, m), 7.25-7.36 (7H, m), 8.53 (1H, s), 10.60-10.64 (1H, m), 11.92 (1H, brs).

Example A-33

9-Hydroxy-2-(2-hydroxy-ethyl)-1,8-dioxo-1,8-dihydro-2H-pyrid[1,2-a]pyrazine-7-carboxylic acid 4-fluoro-benzylamide melting point: 287° C.
NMR (DMSO-d$_6$) δ: 3.63-3.68 (2H, m), 3.81-3.84 (2H, m), 4.54 (2H, d, J=5.8 Hz), 4.95 (1H, t, J=5.5 Hz), 6.90 (1H, d, J=5.9 Hz), 7.14-7.20 (2H, m), 7.35-7.38 (2H, m), 7.48 (1H, d, J=5.8 Hz), 8.81 (1H, s), 10.60 (1H, t, J=5.9 Hz), 12.12 (1H, brs).

According to the same manner as that of Example B-1, the following Examples compounds B-2 to B-28 were synthesized.

Example B-2

2-(2-Dimethylamino-ethyl)-9-hydroxy-1,8-dioxo-1,3,4,8-tetrahydro-2H-pyrid[1,2-a]pyrazine-7-carboxylic acid 4-fluoro-benzylamide melting point: 218-220° C.
NMR (DMSO-d$_6$) δ: 2.19 (6H, s), 3.60 (2H, t, J=6.3 Hz), 3.79 (2H, s), 4.37 (2H, s), 4.52 (2H, d, J=4.5 Hz), 7.15 (2H, t, J=9.0 Hz), 7.32-7.37 (2H, m), 8.40 (1H, s), 10.45 (1H, t, J=6.3 Hz), 12.40 (1H, s).

Example B-3

9-Hydroxy-2-(2-morpholin-4-yl-ethyl)-1,8-dioxo-1,3,4,8-tetrahydro-2H-pyrid[1,2-a]pyrazine-7-carboxylic acid 4-fluoro-benzylamide melting point: 205-207° C.
NMR (DMSO-d$_6$) δ: 2.43 (2H, s), 2.50 (4H, s), 3.54 (4H, s), 3.63 (2H, s), 3.81 (2H, s), 4.40 (2H, s), 4.52 (2H, d, J=6.0 Hz), 7.16 (2H, t, J=9.0 Hz), 7.33-7.37 (2H, m), 8.43 (1H, s), 10.45 (1H, t, J=5.7 Hz), 12.48 (1H, s).

Example B-4

9-Hydroxy-1,8-dioxo-2-(2-piperidin-1-yl-ethyl)-1,3,4,8-tetrahydro-2H-pyrid[1,2-a]pyrazine-7-carboxylic acid 4-fluoro-benzylamide melting point: 232-235° C.
Elementary analysis for C$_{23}$H$_{27}$FN$_4$O$_4$
Cal'd (%): C, 62.43; H, 6.15; F, 4.29; N, 12.66.
Found (%): C, 61.78; H, 5.76; F, 4.04; N, 12.50.
NMR (DMSO-d$_6$) δ: 1.37-1.46 (6H, m), 2.38-2.50 (6H, m), 3.61 (2H, t, J=6.6 Hz), 3.79 (2H, m), 4.37 (2H, m), 4.52 (2H, d, J=6 Hz), 7.12-7.18 (2H, m), 7.32-7.37 (2H, m), 8.41 (1H, s), 10.44 (1H, t, J=6 Hz), 12.50 (1H, brs).

Example B-5

9-Hydroxy-2-(2-methyl-butyl)-1,8-dioxo-1,8-dihydro-1,3,4,8-tetrahydro-2H-pyrid[1,2-a]pyrazine-7-carboxylic acid 4-fluoro-benzylamide melting point: 278-280° C.
Elementary analysis for C$_{21}$H$_{24}$FN$_3$O$_4$
Cal'd (%): C, 62.83; H, 6.03; F, 4.73; N, 10.47.
Found (%): C, 62.45; H, 6.00; F, 4.50; N, 10.43.
NMR (DMSO-d$_6$) δ: 0.86-0.93 (6H, m), 1.08-1.18 (1H, m), 1.37-1.44 (1H, m), 1.78-1.84 (1H, m), 3.30-3.38 (2H, m), 3.73-3.77 (2H, m), 4.37-4.44 (2H, m), 4.52 (2H, d, J=6 Hz), 7.12-7.18 (2H, m), 7.32-7.37 (2H, m), 8.41 (1H, s), 10.46 (1H, t, J=6 Hz), 12.54 (1H, brs).

Example B-6

9-Hydroxy-2-(2-isopropoxy-ethyl)-1,8-dioxo-1,3,4,8-tetrahydro-2H-pyrid[1,2-a]pyrazine-7-carboxylic acid 4-fluoro-benzylamide melting point: 210-212° C.
Elementary analysis for C$_{21}$H$_{24}$FN$_3$O$_5$
Cal'd (%): C, 60.42; H, 5.80; F, 4.55; N, 10.07.
Found (%): C, 59.77; H, 5.66; F, 4.42; N, 10.01.
NMR (DMSO-d$_6$) δ: 1.08 (6H, d, J=6 Hz), 3.54-3.66 (5H, m), 3.79-3.83 (2H, m), 4.35-4.39 (2H, m), 4.52 (2H, d, J=6 Hz), 7.12-7.18 (2H, m), 7.32-7.37 (2H, m), 8.40 (1H, s), 10.44 (1H, t, J=6 Hz), 12.42 (1H, brs).

Example B-7

9-Hydroxy-2-isopropyl-1,8-dioxo-1,3,4,8-tetrahydro-2H-pyrid[1,2-a]pyrazine-7-carboxylic acid 4-fluoro-benzylamide melting point: 286-287° C.
NMR (DMSO-d$_6$) δ: 1.17 (6H, d, J=6.9 Hz), 3.64-3.70 (2H, m), 4.36-4.38 (2H, m), 4.52 (2H, d, J=6.0 Hz), 4.70-4.79 (1H, m), 7.13-7.19 (2H, m), 7.33-7.37 (2H, m), 8.43 (1H, s), 10.47 (1H, t, J=6.0 Hz), 12.60 (1H, brs).

Example B-8)

2-Cyclohexyl-9-hydroxy-1,8-dioxo-1,3,4,8-tetrahydro-2H-pyrid[1,2-a]pyrazine-7-carboxylic acid 4-fluoro-benzylamide melting point: >300° C.
NMR (DMSO-$d_6$) δ: 1.03-1.81 (10H, m), 3.69-3.72 (2H, m), 4.29-4.36 (3H, m), 4.52 (2H, d, J=6.1 Hz), 7.13-7.19 (2H, m), 7.33-7.37 (2H, m), 8.43 (1H, s), 10.47 (1H, t, J=5.8 Hz), 12.59 (1H, brs).

Example B-9

2-(4-Fluoro-benzyl)-9-hydroxy-1,8-dioxo-1,3,4,8-tetrahydro-2H-pyrid[1,2-a]pyrazine-7-carboxylic acid 4-fluoro-benzylamide melting point: 271-272° C.
NMR (DMSO-$d_6$) δ: 3.71-3.75 (2H, m), 4.37-4.41 (2H, m), 4.52 (2H, d, J=6.0 Hz), 4.71 (2H, s), 7.13-7.23 (4H, m), 7.33-7.45 (4H, m), 8.41 (1H, s), 10.44 (1H, t, J=5.9 Hz), 12.36 (1H, brs).

Example B-10

9-Hydroxy-1,8-dioxo-2-[2-(propyl-m-toluoyl-amino)-ethyl]-1,3,4,8-tetrahydro-2H-pyrid[1,2-a]pyrazine-7-carboxylic acid 4-fluoro-benzylamide melting point: 185-188° C.
NMR (CDCl$_3$) δ: 1.12-1.18 (3H, m), 2.26 (3H, s), 3.30-4.40 (10H, m), 4.60 (2H, d, J=5.4 Hz), 6.57 (2H, brs), 6.97-7.02 (2H, m), 7.04-7.16 (1H, m), 7.26-7.34 (3H, m), 8.23 (1H, s), 10.43 (1H, brs), 12.29 (1H, brs).

Example B-11

9-Hydroxy-1,8-dioxo-2-[3-(2-oxo-pyrrolidin-1-yl)-propyl]-1,3,4,8-tetrahydro-2H-pyrid[1,2-a]pyrazine-7-carboxylic acid 4-fluoro-benzylamide melting point: 207-209° C.
NMR (CDCl$_3$) δ: 1.92-1.96 (2H, m), 2.05-2.10 (2H, m), 2.40 (2H, t, J=8.1 Hz), 3.35 (2H, t, J=6.6 Hz), 3.43 (2H, t, J=6.9 Hz), 3.55 (2H, t, J=6.6 Hz), 3.82-3.86 (2H, m), 4.26-4.30 (2H, m), 4.60 (2H, d, J=6.0 Hz), 6.96-7.02 (2H, m), 7.30-7.35 (2H, m), 8.32 (1H, s), 10.43-10.47 (1H, m), 12.26 (1H, brs).

Example B-12

9-Hydroxy-1,8-dioxo-2-(2-tetrahydrofuran-2-ylmethyl)-1,3,4,8-tetrahydro-2H-pyrid[1,2-a]pyrazine-7-carboxylic acid 4-fluoro-benzylamide melting point: 250-251° C.
NMR (CDCl$_3$) δ: 1.50-1.59 (2H, m), 1.89-1.98 (2H, m), 2.03-2.14 (1H, m), 3.25 (1H, dd, J=8.4 Hz, 13.8 Hz), 4.25-3.73 (7H, m), 4.59 (2H, d, J=5.1 Hz), 7.00 (2H, d, J=8.4 Hz), 7.32 (2H, dd, J=5.4 Hz, 8.4 Hz), 8.31 (1H, s), 10.47 (1H, t, 5.1 Hz), 12.29 (1H, brs).

Example B-13

4-[7-(4-Fluoro-benzylcarbamoyl)-9-hydroxy-1,8-dioxo-1,3,4,8-tetrahydro-pyrid[1,2-a]pyrazine-2-yl]-piperidine-1-carboxylic acid ethyl ester melting point: 258-260° C.
NMR (CDCl$_3$) δ: 1.28 (3H, t, J=7.2 Hz), 1.54-1.92 (4H, m), 4.14-4.43 (6H, m), 4.60 (2H, d, J=5.4 Hz), 6.97-7.05 (2H, m), 7.29-7.34 (2H, m), 8.32 (1H, s), 10.43 (1H, t, J=5.4 Hz), 12.27 (1H, brs).

Example B-14

2-(2-Acetylamino-ethyl)-9-hydroxy-1,8-dioxo-1,3,4,8-tetrahydro-2H-pyrid[1, 2-a]pyrazine-7-carboxylic acid 4-fluoro-benzylamide melting point: 249-251° C.
NMR (CDCl$_3$) δ: 1.93 (3H, s), 3.48-3.52 (2H, m), 3.67-3.71 (2H, m), 3.82-3.86 (2H, m), 4.28-4.32 (2H, m), 4.59 (2H, s), 6.99-7.04 (2H, m), 7.30-7.33 (2H, m), 8.30 (1H, s).

Example B-15

9-Hydroxy-2-(3-isopropoxy-propyl)-1,8-dioxo-1,3,4,8-tetrahydro-2H-pyrid[1, 2-a]pyrazine-7-carboxylic acid 4-fluoro-benzylamide melting point: 239-241° C.
NMR (CDCl$_3$) δ: 1.10 (6H, d, J=6.0 Hz), 1.88-1.96 (2H, m), 3.48-3.57 (3H, m), 3.69 (2H, t, J=6.6 Hz), 3.77-3.81 (2H, m), 4.21-4.24 (2H, m), 4.60 (2H, d, J=5.7 Hz), 6.96-7.02 (2H, m), 7.30-7.35 (2H, m), 8.30 (1H, s), 10.45-10.49 (1H, m), 12.42 (1H, brs).

Example B-16

2-(4-Dimethylamino-benzyl)-9-hydroxy-1,8-dioxo-1,3,4,8-tetrahydro-2H-pyrid[1,2-a]pyrazine-7-carboxylic acid 4-fluoro-benzylamide melting point: 260-262° C.
NMR (CDCl$_3$) δ: 2.97 (6H, s), 3.59-3.63 (2H, m), 4.09-4.13 (2H, m), 4.59 (2H, d, J=5.7 Hz), 4.67 (2H, s), 6.70-6.78 (2H, m), 6.96-7.02 (2H, m), 7.19 (2H, d, J=8.7 Hz), 7.29-7.34 (2H, m), 8.27 (1H, s), 10.46 (1H, t, J=5.7 Hz), 12.45 (1H, brs).

Example B-17

9-Hydroxy-1,8-dioxo-2-(4-sulfamoyl-1-benzyl)-1,3,4,8-tetrahydro-2H-pyrid[1,2-a]pyrazine-7-carboxylic acid 4-fluoro-benzylamide melting point: 266-270° C.
NMR (DMSO-$d_6$) δ: 3.75-3.81 (2H, m), 4.41-4.45 (2H, m), 4.52 (2H, d, J=6.0 Hz), 4.80 (2H, s), 7.13-7.19 (2H, m), 7.33-7.37 (4H, m), 7.56 (2H, d, J=8.1 Hz), 7.81 (2H, d, J=8.1 Hz), 8.44 (1H, s), 10.44 (1H, t, J=6.0 Hz), 12.28 (1H, brs).

Example B-18

9-Hydroxy-2-(3-methoxy-propyl)-1,8-dioxo-1,3,4,8-tetrahydro-2H-pyrid[1,2-a]pyrazine-7-carboxylic acid 4-fluoro-benzylamide melting point: 238-240° C.
NMR (CDCl$_3$) δ: 1.93 (2H, quin, J=5.7 Hz), 3.31 (3H, s), 3.47 (2H, t, J=5.7 Hz), 3.68 (2H, t, J=6.9 Hz), 3.75-3.79 (2H, m), 4.21-4.24 (2H, m), 4.60 (2H, d, J=5.7 Hz), 6.97-7.02 (2H, m), 7.30-7.35 (2H, m), 8.31 (1H, s), 10.46 (1H, t, J=7.8 Hz), 12.38 (1H, brs).

Example B-19

9-Hydroxy-1,8-dioxo-2-(2-propoxy-ethyl)-1,3,4,8-tetrahydro-2H-pyrid[1,2-a]pyrazine-7-carboxylic acid 4-fluoro-benzylamide melting point: 196-197° C.
NMR (CDCl$_3$) δ: 0.91 (3H, t, J=7.5 Hz), 1.52-1.63 (2H, m), 3.41 (2H, t, J=7.5 Hz), 3.67 (2H, t, J=4.2 Hz), 3.76 (2H, t, J=4.2 Hz), 3.88-3.92 (2H, m), 4.19-4.23 (2H, m), 4.60 (2H, d, J=6.0 Hz), 6.97-7.03 (2H, m), 7.30-7.35 (2H, m), 8.32 (1H, s), 10.47 (1H, t, J=5.7 Hz), 12.29 (1H, brs).

Example B-20

9-Hydroxy-1,8-dioxo-2-(2-phenoxy-ethyl)-1,3,4,8-tetrahydro-2H-pyrid[1,2-a]pyrazine-7-carboxylic acid 4-fluoro-benzylamide melting point: 200-201° C.
NMR (CDCl$_3$) δ: 3.96-4.02 (4H, m), 4.20-4.28 (4H, m), 4.60 (2H, d, J=6.0 Hz), 6.86-6.89 (2H, m), 6.96-7.02 (3H, m), 7.28-7.34 (4H, m), 8.31 (1H, s), 10.43 (1H, brs), 12.15 (1H, brs).

Example B-21

2-Dimethylcarbamoylmethyl-9-hydroxy-1,8-dioxo-1,3,4,8-tetrahydro-2H-pyrid[1,2-a]pyrazine-7-carboxylic acid 4-fluoro-benzylamide melting point: 245° C.
NMR (CDCl$_3$) δ: 3.00 (3H, s), 3.08 (3H, s), 3.83-3.87 (2H, m), 4.37-4.41 (2H, m), 4.42 (2H, s), 4.60 (2H, s), 6.98-7.04 (2H, m); 7.30-7.34 (2H, m), 8.33 (1H, s).

Example B-22

2-(2-Ethoxy-ethyl)-9-hydroxy-1,8-dioxo-1,3,4,8-tetrahydro-2H-pyrid[1,2-a]pyrazine-7-carboxylic acid 4-fluoro-benzylamide melting point: 201-202° C.
NMR (CDCl$_3$) δ: 1.19 (3H, t, J=7.2 Hz), 3.51 (2H, q, J=7.2 Hz), 3.67 (2H, t, J=5.4 Hz), 3.76 (2H, t, J=5.4 Hz), 3.88-3.92 (2H, m), 4.20-4.23 (2H, m), 4.60 (2H, d, J=5.7 Hz), 6.96-7.02 (2H, m), 7.30-7.34 (2H, m), 8.31 (1H, s), 10.46 (1H, brs), 12.28 (1H, brs).

Example B-23

9-Hydroxy-1,8-dioxo-2-phenethyl-1,3,4,8-tetrahydro-2H-pyrid[1,2-a]pyrazine-7-carboxylic acid 4-fluoro-benzylamide melting point: 241° C.
NMR (CDCl$_3$) δ: 3.00 (2H, t, J=6.3 Hz), 3.41 (2H, brs), 3.82 (2H, t, J=6.6 Hz), 3.97 (2H, brs), 4.59 (2H, d, J=5.1 Hz), 6.96-7.02 (2H, m), 7.22-7.36 (7H, m), 8.24 (1H, brs), 10.45 (1H, brs), 12.31 (1H, brs).

Example B-24

2-(3-Dimethylamino-2,2-dimethyl-propyl)-9-hydroxy-1,8-dioxo-1,3,4,8-tetrahydro-2H-pyrid[1,2-a]pyrazine-7-carboxylic acid 4-fluoro-benzylamide melting point: 212-214° C.
NMR (CDCl$_3$) δ: 1.03 (6H, s), 2.25 (2H, brs), 2.37 (6H, s), 3.55 (2H, s), 3.86-3.90 (2H, m), 4.20-4.24 (2H, m), 4.60 (2H, d, J=6.0 Hz), 6.96-7.02 (2H, m), 7.29-7.34 (2H, m), 8.30 (1H, s), 10.46 (1H, t, J=4.5 Hz), 12.43 (1H, brs).

Example B-25

9-Hydroxy-2-(3-morpholin-4-yl-propyl)-1,8-dioxo-1,3,4,8-tetrahydro-2H-pyrid[1,2-a]pyrazine-7-carboxylic acid 4-fluoro-benzylamide melting point: 181-185° C.
NMR (CDCl$_3$) δ: 2.08 (2H, brs), 2.73 (6H, brs), 3.67 (2H, t, J=6.6 Hz), 3.80-3.84 (6H, m), 4.22-4.26 (2H, m), 4.61 (2H, d, J=6.0 Hz), 6.98-7.04 (2H, m), 7.33-7.38 (2H, m), 8.28 (1H, s), 10.41 (1H, t, J=6.0 Hz), 12.19 (1H, brs).

Example B-26)

Diethyl {2-[7-(4-fluorobenzylcarbamoyl)-9-hydroxy-1,8-dioxo-1,3,4,8-tetrahydropyrid[1,2-a]pyrazin-2-yl]ethyl}phosphonate NMR (DMSO-d$_6$) δ: 1.24 (6H, d, J=7.0 Hz), 2.1-2.23 (2H, m), 3.64-3.72 (2H, m), 3.79-3.82 (2H, m), 3.99-4.06 (4H, m), 4.37-4.41 (2H, m), 7.52 (2H, d, J=5.7 Hz), 7.12-7.18 (2H, m), 7.33-7.38 (2H, m), 8.42 (1H, s), 10.43 (1H, t, J=5.7 Hz), 12.34 (1H, s).

Example B-27

2-(3-Tert-butylamino-propyl)-9-hydroxy-1,8-dioxo-1,3,4,8-tetrahydro-2H-pyrid[1,2-a]pyrazine-7-carboxylic acid 4-fluoro-benzylamide melting point: 216° C.
NMR (DMSO-d$_6$) δ: 1.40 (9H, s), 2.18 (2H, s), 2.92 (2H, s), 3.40 (2H, s), 3.90 (2H, s), 4.39 (2H, s), 4.59 (2H, s), 7.01 (2H, t, J=11.6 Hz), 7.31 (2H, m), 8.34 (1H, s), 10.48 (1H, s).

Example B-28

9-Hydroxy-2-(2-hydroxy-ethyl)-1,8-dioxo-1,3,4,8-tetrahydro-2H-pyrid[1,2-a]pyrazine-7-carboxylic acid 4-fluoro-benzylamide melting point: 213° C.

NMR (DMSO-d$_6$) δ: 3.57-3.63 (4H, m), 3.80-3.84 (2H, m), 4.36-4.41 (2H, m), 4.52 (2H, d, J=5.8 Hz), 4.89 (1H, t, J=5.5 Hz), 7.13-7.20 (2H, m), 7.32-7.38 (2H, m), 8.42 (1H, s), 10.46 (1H, t, J=5.8 Hz), 12.52 (1H, brs).

Compound 10 can be also synthesized by the following method.

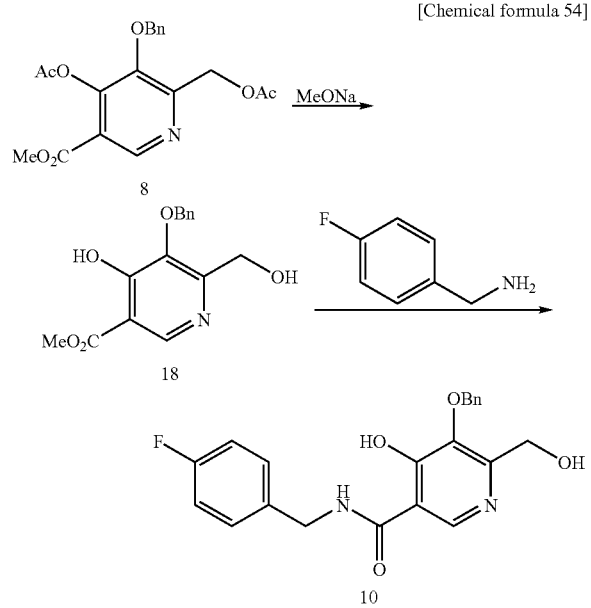

18) The compound 8 (9.5 g, 25.4 mmol) was dissolved in methanol (50 ml), and a sodium methylate methanol solution (7.35 ml, 38.1 mmol) was added. The solution was stirred at room temperature for 1 hour, an aqueous saturated ammonium chloride solution was added, and crystals were collected by filtration. Washing with water and diethyl ether afforded 5-benzyloxy-4-hydroxy-6-hydroxymethyl-nicotinic acid methyl ester 18 (4.68 g, 64%) as a colorless crystal.

NMR (DMSO-d$_6$) δ: 3.72 (2H, s), 4.37 (2H, s), 5.06 (2H, s), 5.72 (1H, brs), 7.34-7.40 (5H, m), 11.47 (1H, brs).

19) The compound 18 (3.76 g, 13.0 mmol) was dissolved in dimethylformamide (38 ml), and 4-fluorobenzylamine (2.44 ml, 21.3 mmol) was added, followed by stirring at 120° C. for 2 hours. The reaction solution was cooled to room temperature, and the solvent was distilled off under reduced pressure, followed by dilution with ethyl acetate. Thereafter, this was washed with 2N hydrochloric acid and water, and dried with anhydrous sodium sulfate. The solvent was distilled off under reduced pressure, and the residue was washed with diethyl ether to obtain 5-benzyloxy-N-(4-fluoro-benzyl)-4-hydroxy-6-hydroxymethyl-nicotinic acid amide 10 (3.59 g, 72%) as a beige crystal.

Example D-1

3,9-Dihydroxy-2-(2-methoxy-ethyl)-1,8-dioxo-1,3,4,8-tetrahydro-2H-pyrid[1,2-a]pyrazine-7-carboxylic acid 4-fluoro-benzylamide

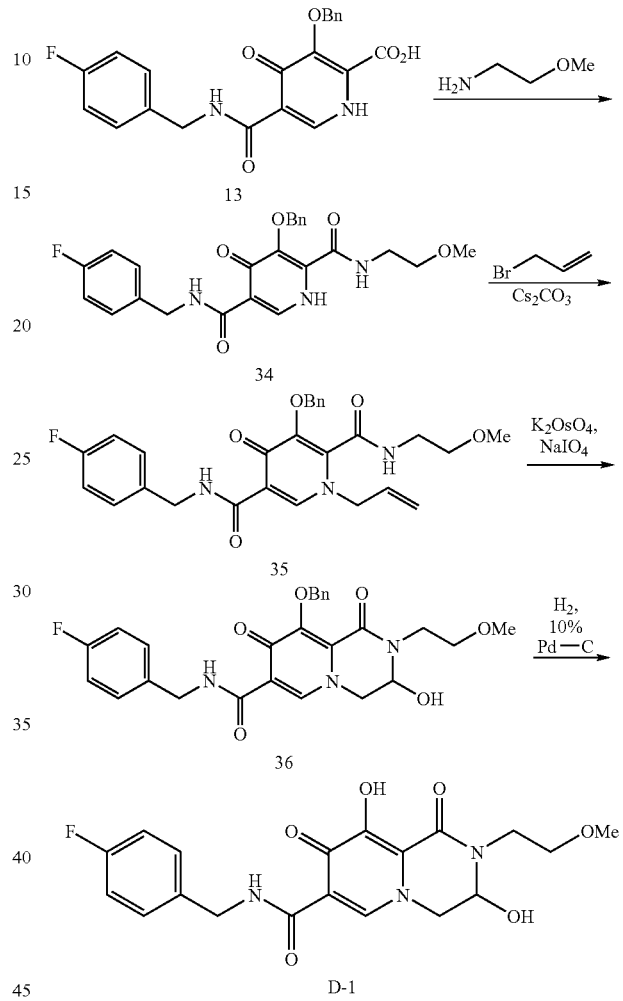

1) Using a compound 13, a compound 34 was synthesized according to the method of synthesizing a compound 10.

1H-NMR (CDCl$_3$) δ: 3.27 (3H, s), 3.76-3.40 (2H, m), 3.47-3.52 (2H, m), 4.63 (2H, d, J=6.1 Hz), 5.48 (2H, s), 6.99-7.05 (2H, m), 7.33-7.45 (7H, m), 8.54-8.58 (1H, m), 8.62 (1H, d, J=6.7 Hz), 10.44-10.48 (1H, m).

2) Using a compound 34, a compound 35 was synthesized according to the method of synthesizing a compound 15.

1H-NMR (CDCl$_3$) δ: 3.21 (3H, s), 3.32-3.35 (2H, m), 3.38-3.45 (2H, m), 4.58-4.61 (4H, m), 5.14-5.30 (4H, s), 5.82-5.93 (1H, m), 6.72 (1H, brs), 6.98-7.04 (2H, m), 7.30-7.39 (7H, m), 8.41 (1H, s), 10.43-10.47 (1H, m).

3) Using a compound 35, a compound 36 was synthesized according to the method of synthesizing a compound 16.

1H-NMR (CDCl$_3$) δ: 3.07-3.17 (1H, s), 3.42 (3H, s), 3.44-3.49 (1H, m), 3.61-3.69 (1H, m), 4.11-4.17 (4H, m), 4.26-4.31 (1H, m), 4.43-4.49 (1H, m), 4.59-4.62 (2H, m), 5.00-5.08 (2H, m), 5.20 (1H, d, J=9.9 Hz), 5.34 (1H, d, J=9.9 Hz), 6.98-7.04 (2H, m), 7.30-7.35 (5H, m), 7.60-7.63 (1H, s), 8.38 (1H, s), 10.45-10.49 (1H, m).

4) According to the method of synthesizing Example B-1, Example D-1 was synthesized.

melting point: 163-164° C.

1H-NMR (CDCl$_3$) δ: 3.24-3.32 (1H, m), 3.46 (3H, s), 3.52-3.57 (1H, m), 3.72-3.80 (1H, m), 4.17-4.39 (3H, m), 4.62 (2H, d, J=5.8 Hz), 5.12 (1H, t, J=2.1 Hz), 6.97-7.03 (2H, m), 7.30-7.35 (2H, m), 8.32 (1H, s), 10.36-10.38 (1H, m), 12.02 (1H, brs).

According to the same manner as that of Example D-1, the following Example compounds D-2 to D-35 were synthesized.

Example D-2)

2-Cyclohexylmethyl-3,9-dihydroxy-1,8-dioxo-1,3,4,8-tetrahydro-2H-pyrid[1,2-a]pyrazine-7-carboxylic acid 4-fluoro-benzylamide melting point: 240-241° C.

1H-NMR (DMSO-d$_6$) δ: 0.96-1.71 (11H, m), 3.06 (1H, dd, J=6.6 Hz, 12.9 Hz), 3.67 (1H, dd, J=6.9 Hz, 13.5 Hz), 4.36 (1H, d, J=13.2 Hz), 4.47 (1H, d, J=13.2 Hz), 4.52 (2H, d, J=5.7 Hz), 5.22 (1H, s), 6.94 (1H, s), 7.15 (2H, t, bJ=8.71 Hz), 7.35 (2H, dd, J=6.0 Hz, 8.7 Hz), 8.46 (1H, s), 10.45 (1H, s), 12.35 (1H, s).

Example D-3

3,9-Dihydroxy-2-methyl-1,8-dioxo-1,3,4,8-tetrahydro-2H-pyrid[1,2-a]pyrazine-7-carboxylic acid 4-fluoro-benzylamide melting point: 200-201° C.

1H-NMR (DMSO-d$_6$) δ: 3.09 (3H, s), 4.37 (1H, d, J=12.8 Hz), 4.47 (1H, d, J=12.8 Hz), 4.52 (2H, d, J=6.0 Hz), 5.25 (1H, s), 7.00 (1H, d, J=6.4 Hz), 7.15 (2H, t, J=9.6 Hz), 7.35 (2H, dd, J=5.6 Hz, 8.4 Hz), 8.32 (1H, s), 10.46 (1H, s), 12.33 (1H, s).

Example D-4)

Diethyl {2-[7-(4-fluorobenzylcarbamoyl)-3,9-dihydroxy-1-8-dioxo-1,3,4,8-tetrahydropyrid[1,2-a]pyrazin-2-yl]ethyl}phosphonate 1H-NMR (DMSO-d$_6$) δ: 1.26 (6H, td, J=7.2, 1.6 Hz), 2.09-2.33 (2H, m), 3.46-3.55 (1H, m), 3.84-3.91 (1H, m), 3.98-4.07 (4H, m), 4.32 (1H, d, J=12.4 Hz), 4.47-4.54 (3H, m), 5.37-5.40 (1H, m), 7.04 (1H, d, J=6.4 Hz), 7.13-7.18 (2H, m), 7.33-7.38 (2H, m), 8.50 (1H, s), 10.39 (1H, t, J=6.0 Hz), 12.05 (1H, s).

Example D-5

3,9-Dihydroxy-2-(2-isopropoxy-ethyl)-1,8-dioxo-1,3,4,8-tetrahydro-2H-pyrid[1,2-a]pyrazine-7-carboxylic acid 4-fluoro-benzylamide NMR (DMSO-d$_6$) δ: 1.08-1.10 (6H, m), 3.41-3.46 (1H, m), 3.55-3.62 (2H, m), 3.87-3.91 (1H, m), 4.31 (1H, d, J=12.8 Hz), 4.49-4.53 (3H, m), 5.33 (1H, s), 6.91 (1H, d, J=6.0 Hz), 7.13-7.18 (2H, m), 7.34-7.37 (2H, m), 8.49 (1H, s), 10.40 (1H, t, J=6.0 Hz), 12.16 (1H, s).

Example D-6

3,9-Dihydroxy-2-(3-isopropoxy-propyl)-1,8-dioxo-1,3,4,8-tetrahydro-2H-pyrid[1,2-a]pyrazine-7-carboxylic acid 4-fluoro-benzylamide NMR (DMSO-d$_6$) δ: 1.07-1.09 (6H, m), 1.80-1.87 (2H, m), 3.34-3.43 (3H, m), 3.48-3.55 (1H, m), 3.76-3.83 (1H, m), 4.34 (1H, d, J=12.8 Hz), 4.46-4.53 (3H, m), 5.28 (1H, s), 6.94 (1H, s), 7.13-7.18 (2H, m), 7.34-7.37 (2H, m), 8.48 (1H, s), 10.42-10.48 (1H, m), 12.30 (1H, s).

Example D-7

2-Dimethylcarbamoylmethyl-3,9-dihydroxy-1,8-dioxo-1,3,4,8-tetrahydro-2H-pyrid[1,2-a]pyrazine-7-carboxylic acid 4-fluoro-benzylamide NMR (DMSO-d$_6$) δ: 2.87 (3H, s), 3.03 (3H, s), 4.28 (1H, d, J=16.8 Hz), 4.39 (1H, d, J=12.0 Hz), 4.50 (1H, d, J=12.4 Hz), 4.49-4.54 (3H, m), 4.72 (1H, d, J=16.8 Hz), 5.19 (1H, s), 6.92 (1H, d, J=4.8 Hz), 7.13-7.18 (2H, m), 7.32-7.38 (2H, m), 8.50 (1H, s), 10.40-10.46 (1H, m), 12.20 (1H, s).

Example D-8

4-[7-(4-Fluoro-benzylcarbamoyl)-3,9-dihydroxy-1,8-dioxo-1,3,4,8-tetrahydro-2H-pyrid[1,2-a]pyrazine-1-carboxylic acid ethyl ester NMR (DMSO-d$_6$) δ: 1.19 (3H, t, J=6.8 Hz), 1.68-1.81 (4H, m), 2.81-2.89 (2H, m), 4.02-4.11 (4H, m), 4.23-4.38 (2H, m), 4.45-4.53 (3H, m), 5.41 (1H, d, J=7.6 Hz), 6.73 (1H, d, J=6.8 Hz), 7.13-7.18 (2H, m), 7.34-7.37 (2H, m), 8.49 (1H, s), 10.40-10.45 (1H, m), 12.18 (1H, s).

Example D-9

2-(3-Dimethylamino-2,2-dimethyl-propyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-d$_6$) δ: 0.91 (6H, d, J=8.0 Hz), 1.04 (2H, d, J=6.0 Hz), 3.10 (1H, d, J=13.2 Hz), 3.83 (1H, d, J=13.2 Hz), 4.48-4.53 (3H, m), 5.25 (1H, s), 7.13-7.18 (2H, m), 7.34-7.38 (2H, m), 8.49 (1H, s), 10.42-10.47 (1H, m).

Example D-10

3,9-Dihydroxy-1,8-dioxo-2-pyridin-3-ylmethyl-1,3,4,8-tetrahydro-2H-pyrid[1,2-a]pyrazine-7-carboxylic acid 4-fluoro-benzylamide NMR (DMSO-d$_6$) δ: 4.41-4.57 (5H, m), 4.50 (1H, d, J=15.6 Hz), 5.36 (1H, d, J=6.8 Hz), 7.08 (1H, d, J=6.8 Hz), 7.13-7.19 (2H, m), 7.13-7.18 (2H, m), 7.34-7.40 (3H, m), 7.78-7.83 (1H, m), 8.49-8.51 (2H, m), 8.62 (1H, s), 10.38-10.42 (1H, m), 12.19 (1H, s).

Example D-11

2-[2-(4-Fluoro-phenyl)-ethyl]-3,9-dihydroxy-1,8-dioxo-1,3,4,8-tetrahydro-2H-pyrid[1,2-a]pyrazine-7-carboxylic acid 4-fluoro-benzylamide NMR (DMSO-d$_6$) δ: 2.94 (2H, t, J=7.2 Hz), 3.47-3.54 (1H, m), 3.92-3.99 (1H, m), 4.25 (1H, d, J=12.8 Hz), 4.48 (1H, d, J=13.2 Hz), 4.53 (2H, d, J=6.0 Hz), 5.22 (1H, d, J=6.4 Hz), 7.02 (1H, d, J=6.4 Hz), 7.11-7.18 (4H, m), 7.32-7.38 (4H, m), 8.50 (1H, s), 10.41 (1H, t, J=6.0 Hz), 12.20 (1H, s).

Example D-12

3,9-Dihydroxy-1,8-dioxo-2-(2,2,2-trifluoro-ethyl)-1,3,4,8-tetrahydro-2H-pyrid[1,2-a]pyrazine-7-carboxylic acid 4-fluoro-benzylamide NMR (DMSO-$d_6$) δ: 4.13-4.23 (1H, m), 4.43 (1H, d, J=13.2 Hz), 4.53-4.68 (4H, m), 5.38 (1H, s), 7.13-7.18 (3H, m), 7.35-7.38 (2H, m), 8.53 (1H, s), 10.35 (1H, t, J=6.0 Hz), 11.50 (1H, s).

Example D-13

3,9-Dihydroxy-1,8-dioxo-2-(1,1,3,3-tetramethyl-butyl)-1,3,4,8-tetrahydro-2H-pyrid[1,2-a]pyrazine-7-carboxylic acid 4-fluoro-benzylamide NMR (DMSO-$d_6$) δ: 0.95 (9H, s), 1.56 (6H, d, J=21.6 Hz), 2.50 (2H, s), 4.20 (1H, d, J=13.2 Hz), 4.47 (1H, d, J=12.9 Hz), 4.53 (2H, d, J=6.0 Hz), 5.63 (1H, s), 6.72 (1H, s), 7.13-7.18 (2H, m), 7.34-7.37 (2H, m), 8.46 (1H, s), 10.48 (1H, t, J=6.0 Hz), 12.62 (1H, s).

Example D-14

2-(2,2-Dimethyl-propyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 0.95 (9H, s), 2.93 (1H, d, J=13.6 Hz), 3.82 (1H, d, J=12.9 Hz), 4.48-4.54 (4H, m), 5.22 (1H, s), 7.07 (1H, s), 7.13-7.18 (2H, m), 7.34-7.38 (2H, m), 8.45 (1H, s), 10.48 (1H, t, J=6.0 Hz), 12.45 (1H, s).

Example D-15

3,9-Dihydroxy-1,8-dioxo-2-trimethylsilanylmethyl-1,3,4,8-tetrahydro-2H-pyrid[1,2-a]pyrazine-7-carboxylic acid 4-fluoro-benzylamide NMR (DMSO-$d_6$) δ: 0.10 (9H, s), 2.95 (1H, d, J=14.8 Hz), 3.27 (1H, d, J=14.8 Hz), 4.36-4.53 (4H, m), 5.14 (1H, s), 7.04 (1H, s), 7.13-7.17 (2H, m), 7.33-7.37 (2H, m), 8.48 (1H, s), 10.47 (1H, t, J=6.0 Hz), 12.45 (1H, s).

Example D-16

2-Fluoromethyl-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 3.56-3.70 (1H, m), 3.89-4.11 (1H, m), 4.36 (1H, d, J=13.2 Hz), 4.46-4.75 (5H, m), 5.32 (1H, s), 6.99 (1H, s), 7.13-7.19 (2H, m), 7.32-7.37 (2H, m), 8.46 (1H, s), 10.42 (1H, t, J=6.0 Hz), 12.04 (1H, s).

Example D-17

2-(2-Ethoxy-ethyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 1.11 (3H, t, J=6.8 Hz), 3.47 (2H, q, J=6.8 Hz), 3.53-3.63 (2H, m), 3.88-3.93 (1H, m), 4.32 (1H, d, J=11.6 Hz), 4.48-4.53 (3H, m), 5.33 (1H, d, J=6.0 Hz), 6.92 (1H, d, J=6.0 Hz), 7.13-7.18 (2H, m), 7.34-7.37 (2H, m), 8.49 (1H, s), 10.40 (1H, t, J=6.0 Hz), 12.16 (1H, s).

Example D-18

3,9-Dihydroxy-2-(3-methoxy-propyl)-1,8-dioxo-1,3,4,8-tetrahydro-2H-pyrid[1,2-a]pyrazine-7-carboxylic acid 4-fluoro-benzylamide NMR (DMSO-$d_6$) δ: 1.82-1.91 (2H, m), 3.24 (3H, s), 3.35-3.40 (3H, m), 3.74-3.81 (1H, m), 4.35 (1H, d, J=12.4 Hz), 4.48 (1H, d, J=14.0 Hz), 4.52 (2H, d, J=5.6 Hz), 5.27 (1H, d, J=6.4 Hz), 6.95 (1H, d, J=6.4 Hz), 7.13-7.18 (2H, m), 7.34-7.37 (2H, m), 8.50 (1H, s), 10.42 (1H, t, J=6.0 Hz), 12.28 (1H, s).

Example D-19

3,9-Dihydroxy-1,8-dioxo-2-(2-propoxy-ethyl)-1,3,4,8-tetrahydro-2H-pyrid[1,2-a]pyrazine-7-carboxylic acid 4-fluoro-benzylamide NMR (DMSO-$d_6$) δ: 0.86 (3H, t, J=6.8 Hz), 1.47-1.56 (2H, m), 3.36-3.39 (2H, m), 3.40-3.50 (1H, m), 3.53-3.63 (2H, m), 3.91-3.94 (1H, m), 4.32 (1H, d, J=12.4 Hz), 4.49-4.53 (3H, m), 5.33 (1H, d, J=6.0 Hz), 6.92 (1H, d, J=6.4 Hz), 7.13-7.18 (2H, m), 7.34-7.37 (2H, m), 8.49 (1H, s), 10.40 (1H, t, J=6.0 Hz), 12.16 (1H, s).

Example D-20

3,9-Dihydroxy-2-methylcarbamoylmethyl-1,8-dioxo-1,3,4,8-tetrahydro-2H-pyrid[1,2-a]pyrazine-7-carboxylic acid 4-fluoro-benzylamide NMR (DMSO-$d_6$) δ: 2.63 (3H, d, J=4.4 Hz), 3.98 (1H, d, J=16.4 Hz), 4.37 (1H, d, J=16.4 Hz), 4.42-4.53 (4H, m), 5.27 (1H, s), 7.03 (1H, s), 7.13-7.18 (2H, m), 7.34-7.38 (2H, m), 8.06 (1H, d, J=4.0 Hz), 8.50 (1H, s), 10.40 (1H, t, J=6.0 Hz), 11.88 (1H, s).

Example D-21

2-(3-Chloro-2-fluoro-benzyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 4.42-4.64 (5H, m), 5.02 (1H, d, J=15.6 Hz), 5.30-5.35 (1H, m), 7.10-7.24 (4H, m), 7.34-7.55 (4H, m), 8.52 (1H, s), 10.39 (1H, t, J=6.0 Hz), 11.91 (1H, s).

Example D-22

2-(3-Fluoro-benzyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 4.42-4.54 (5H, m), 5.04 (1H, d, J=15.6 Hz), 5.29 (1H, s), 7.08-7.43 (9H, m), 8.51 (1H, s), 10.42 (1H, t, J=6.0 Hz), 12.02 (1H, s).

Example D-23

3,9-Dihydroxy-1,8-dioxo-2-(3-phenyl-propyl)-1,3,4,8-tetrahydro-2H-pyrid[1,2-a]pyrazine-7-carboxylic acid 4-fluoro-benzylamide NMR (DMSO-$d_6$) δ: 1.85-2.02 (2H, m), 2.63 (2H, t, J=7.6 Hz), 3.33-3.46 (2H, m), 4.32 (1H, d, J=12.4 Hz), 4.47 (1H, d, J=12.8 Hz), 4.53 (2H, d, J=6.0 Hz), 5.30 (1H, s), 6.94 (1H, s), 7.13-7.37 (9H, m), 8.48 (1H, s), 10.44 (1H, t, J=6.0 Hz), 12.30 (1H, s).

Example D-24

3,9-Dihydroxy-1,8-dioxo-2-(4-phenyl-butyl)-1,3,4,8-tetrahydro-2H-pyrid[1,2-a]pyrazine-7-carboxylic acid 4-fluoro-benzylamide NMR (DMSO-$d_6$) δ: 1.55-1.70 (4H, m), 2.58-2.64 (2H, m), 3.71-3.76 (2H, m), 4.33 (1H, d, J=13.6 Hz), 4.45-4.53 (3H, m), 5.28 (1H, s), 6.92 (1H, s), 7.13-7.37 (9H, m), 8.49 (1H, s), 10.41 (1H, t, J=6.0 Hz), 12.31 (1H, s).

Example D-25

3,9-Dihydroxy-1,8-dioxo-2-(4-trifluoromethyl-benzyl)-1,3,4,8-tetrahydro-2H-pyrid[1,2-a]pyrazine-7-carboxylic acid 4-fluoro-benzylamide NMR (DMSO-$d_6$) δ: 4.43-4.62 (5H, m), 5.08 (1H, d, J=16 Hz), 5.32 (1H, s), 7.09-7.18 (3H, m), 7.34-7.38 (2H, m), 7.62 (2H, d, J=8.0 Hz), 7.72 (2H, d, J=8.0 Hz), 8.52 (1H, s), 10.39 (1H, t, J=6.0 Hz), 11.90 (1H, s).

Example D-26

3,9-Dihydroxy-1,8-dioxo-2-propyl-1,3,4,8-tetrahydro-2H-pyrid[1,2-a]pyrazine-7-carboxylic acid 4-fluoro-benzylamide NMR (DMSO-$d_6$) δ: 0.90 (3H, t, J=7.2 Hz), 1.60-1.69 (2H, m), 3.25-3.32 (1H, m), 3.64-3.71 (1H, m), 4.35 (1H, d, J=12.4 Hz), 4.47-4.53 (3H, m), 5.30 (1H, s), 6.93 (1H, s), 7.13-7.18 (2H, m), 7.34-7.37 (2H, m), 8.50 (1H, s), 10.43 (1H, t, J=6.0 Hz), 12.33 (1H, s).

Example D-27

3,9-Dihydroxy-2-(3-methoxy-benzyl)-1,8-dioxo-1,3,4,8-tetrahydro-2H-pyrid[1,2-a]pyrazine-7-carboxylic acid 4-fluoro-benzylamide NMR (DMSO-$d_6$) δ: 3.75 (3H, s), 4.38 (2H, d, J=14.4 Hz), 4.49-4.54 (3H, m), 5.08 (1H, d, J=14.4 Hz), 5.23 (1H, s), 6.86-6.88 (1H, m), 6.94-6.96 (2H, m), 7.08-7.38 (6H, m), 8.50 (1H, s), 10.42 (1H, t, J=6.0 Hz), 12.12 (1H, s).

Example D-28

3,9-Dihydroxy-1,8-dioxo-2-(2-phenoxy-ethyl)-1,3,4,8-tetrahydro-2H-pyrid[1,2-a]pyrazine-7-carboxylic acid 4-fluoro-benzylamide NMR (DMSO-$d_6$) δ: 3.66-3.75 (1H, m), 4.11-4.35 (4H, m), 4.50-4.53 (3H, m), 5.44 (1H, s), 6.93-7.18 (6H, m), 7.28-7.37 (4H, m), 8.49 (1H, s), 10.41 (1H, t, J=6.0 Hz), 12.08 (1H, s).

Example D-29

2-(2-Cyano-ethyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 2.90 (2H, t, J=6.8 Hz), 3.62-3.71 (1H, m), 3.89-3.99 (1H, m), 4.36 (1H, d, J=13.2 Hz), 4.50-4.53 (3H, m), 5.39 (1H, s), 7.04 (1H, s), 7.13-7.18 (2H, m), 7.34-7.37 (2H, m), 8.49 (1H, s), 10.38 (1H, t, J=6.0 Hz), 11.89 (1H, s).

Example D-30

3,9-Dihydroxy-2-isobutyl-1,8-dioxo-1,3,4,8-tetrahydro-2H-pyrid[1,2-a]pyrazine-7-carboxylic acid 4-fluoro-benzylamide NMR (DMSO-$d_6$) δ: 0.89 (3H, d, J=6.4 Hz), 0.93 (3H, d, J=6.8 Hz), 2.01-2.08 (1H, m), 3.04-3.09 (1H, m), 3.62-3.67 (1H, m), 4.38 (1H, d, J=12.4 Hz), 4.48-4.53 (3H, m), 5.26 (1H, s), 6.95-6.96 (1H, m), 7.13-7.18 (2H, m), 7.34-7.37 (2H, m), 8.51 (1H, s), 10.43 (1H, t, J=6.0 Hz), 12.34 (1H, s).

Example D-31

2-(2-Ethyl-butyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 0.87 (6H, q, J=8.0 Hz), 1.24-1.34 (4H, m), 1.68-1.73 (1H, m), 3.12-3.17 (1H, m), 3.72-3.77 (1H, m), 4.36 (1H, d, J=13.2 Hz), 4.49-4.54 (3H, m), 5.25 (1H, s), 7.00 (1H, s), 7.13-7.18 (2H, m), 7.34-7.38 (2H, m), 8.50 (1H, s), 10.42 (1H, t, J=6.0 Hz), 12.36 (1H, s).

Example D-32

2-(3-Ethoxy-propyl)-3,9-dihydroxy-1,8-dioxo-1,3,4,8-tetrahydro-2H-pyrid[1,2-a]pyrazine-7-carboxylic acid 4-fluoro-benzylamide NMR (DMSO-$d_6$) δ: 1.11 (3H, t, J=7.2 Hz), 1.83-1.89 (2H, m), 3.35-3.43 (5H, m), 3.76-3.82 (1H, m), 4.34 (1H, d, J=12.8 Hz), 4.46-4.53 (3H, m), 5.28 (1H, s), 6.94 (1H, s), 7.13-7.18 (2H, m), 7.34-7.37 (2H, m), 8.48 (1H, s), 10.43 (1H, t, J=6.0 Hz), 12.30 (1H, s).

Example D-33

[7-(4-Fluoro-benzylcarbamoyl)-3,9-dihydroxy-1,8-dioxo-1,3,4,8-tetrahydro-2H-pyrid[1,2-a]pyrazin-2-yl]-acetic acid tertiary butyl ester NMR (DMSO-$d_6$) δ: 1.44 (9H, s), 4.09 (1H, d, J=17.6 Hz), 4.32-4.40 (2H, m), 4.49-4.54 (3H, m), 5.29 (1H, s), 6.98 (1H, s), 7.13-7.18 (2H, m), 7.34-7.38 (2H, m), 8.50 (1H, s), 10.38 (1H, t, J=6.0 Hz), 11.72 (1H, s).

Example D-34

3,9-Dihydroxy-1,8-dioxo-2-(2-tetrahydropyran-4-yl)-1,3,4,8-tetrahydro-2H-pyrid[1,2-a]pyrazine-7-carboxylic acid 4-fluoro-benzylamide NMR (DMSO-$d_6$) δ: 1.57-1.64 (1H, m), 1.72-1.77 (1H, m), 1.86-1.98 (2H, m), 3.37-3.46 (2H, m), 3.94 (2H, d, J=10.4

Hz), 4.25-4.53 (5H, m), 5.43 (1H, s), 6.70 (1H, s), 7.13-7.18 (2H, m), 7.34-7.37 (2H, m), 8.46 (1H, s), 10.46 (1H, t, J=6.0 Hz), 12.22 (1H, s).

Example D-35

3,9-Dihydroxy-1,8-dioxo-2-(2-tetrahydropyran-4-ylmethyl)-1,3,4,8-tetrahydro-2H-pyrid[1,2-a]pyrazine-7-carboxylic acid 4-fluoro-benzylamide NMR (DMSO-d$_6$) δ: 1.15-1.31 (2H, m), 1.59 (2H, d, J=11.6 Hz), 1.94-2.03 (1H, m), 3.12-3.17 (1H, m), 3.23-3.36 (2H, m), 3.67-3.72 (1H, m), 3.85 (2H, d, J=10.0 Hz), 4.37-4.53 (4H, m), 5.26 (1H, s), 6.96 (1H, s), 7.13-7.18 (2H, m), 7.34-7.37 (2H, m), 8.47 (1H, s), 10.44 (1H, t, J=6.0 Hz), 12.28 (1H, s).

Amine used in the step 2) of synthesizing a compound 10 was changed to 2-chloro-3-fluoro-benzylamine and, thereafter, according to the method of synthesizing Example D-1, the following Example compounds D-36 to D-38 were synthesized.

Example D-36

2-(2-Ethoxy-ethyl)-3,9-dihydroxy-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 1.11 (3H, t, J=6.0 Hz), 3.45-3.62 (5H, m), 3.88-3.93 (1H, m), 4.30-4.33 (1H, m), 4.48-4.51 (1H, m), 4.62 (2H, d, J=5.6 Hz), 5.33 (1H, s), 6.91-6.93 (1H, m), 7.18-7.22 (1H, m), 7.30-7.36 (1H, m), 7.47-7.51 (1H, m), 8.48 (1H, s), 10.45 (1H, t, J=5.6 Hz), 12.17 (1H, s).

Example D-37

3,9-Dihydroxy-2-(3-isopropoxy-propyl)-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 1.08 (6H, d, J=6.0 Hz), 1.83 (2H, t, J=6.4 Hz), 3.40-3.42 (2H, m), 3.51-3.54 (1H, m), 3.76-3.81 (1H, m), 4.33-4.36 (1H, m), 4.46-4.49 (1H, m), 4.58-4.63 (3H, m), 5.28 (1H, s), 6.93-6.98 (1H, m), 7.18-7.22 (1H, m), 7.30-7.36 (1H, m), 7.48-7.52 (1H, m), 8.48 (1H, s), 10.47 (1H, t, J=5.6 Hz), 12.31 (1H, s).

Example D-38

3,9-Dihydroxy-2-isopropyl-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 1.27 (6H, dd, J=12.8, 6.8 Hz), 4.25-4.28 (1H, m), 4.46-4.63 (4H, m), 5.41 (1H, d, J=6.8 Hz), 6.70 (1H, d, J=6.8 Hz), 7.18-7.22 (1H, m), 7.30-7.34 (1H, m), 7.48-7.51 (1H, m), 8.47 (1H, s), 10.49 (1H, t, J=6.0 Hz), 12.35 (1H, s).

Example D-39

2-(4-Fluorobenzyl)-3,9-dihydroxy-1,8-dioxo-1,3,4,8-tetrahydro-2H-pyrid[1,2-a]pyrazine-7-carboxylic acid 4-fluoro-benzylamide 1H-NMR (DMSO-d$_6$) δ: 4.35-4.49 (3H, m), 4.53 (2H, d, J=6.0 Hz), 5.30 (1H, d, J=15.2 Hz), 5.27 (1H, d, J=6.4 Hz), 7.08 (1H, d, J=6.8 Hz), 7.13-7.21 (4H, m), 7.33-7.38 (2H, m), 7.42-7.46 (2H, m), 8.51 (1H, s), 10.40 (1H, t, J=5.8 Hz), 12.07 (1H, s).

Example D-40

3,9-Dihydroxy-2-isopropyl-1,8-dioxo-1,3,4,8-tetrahydro-2H-pyrid[1,2-a]pyrazine-7-carboxylic acid 4-fluoro-benzylamide 1H-NMR (DMSO-d$_6$) δ: 1.26 (3H, d, J=6.8 Hz), 1.29 (3H, d, J=6.8 Hz), 4.26 (1H, d, J=13.2 Hz), 4.48 (1H, d, J=13.2 Hz), 4.52 (2H, d, J=6.0 Hz), 4.50-4.57 (1H, m), 5.42 (1H, d, J=6.6 Hz), 6.68 (1H, d, J=6.6 Hz), 7.13-7.18 (2H, m), 7.33-7.38 (2H, m), 8.49 (1H, s), 10.44 (1H, t, J=6.0 Hz), 12.34 (1H, s).

Example D-41

4,9-Dihydroxy-2-(2-methoxy-ethyl)-1,8-dioxo-1,3,4,8-tetrahydro-2H-pyrid[1,2-a]pyrazine-7-carboxylic acid 4-fluoro-benzylamide

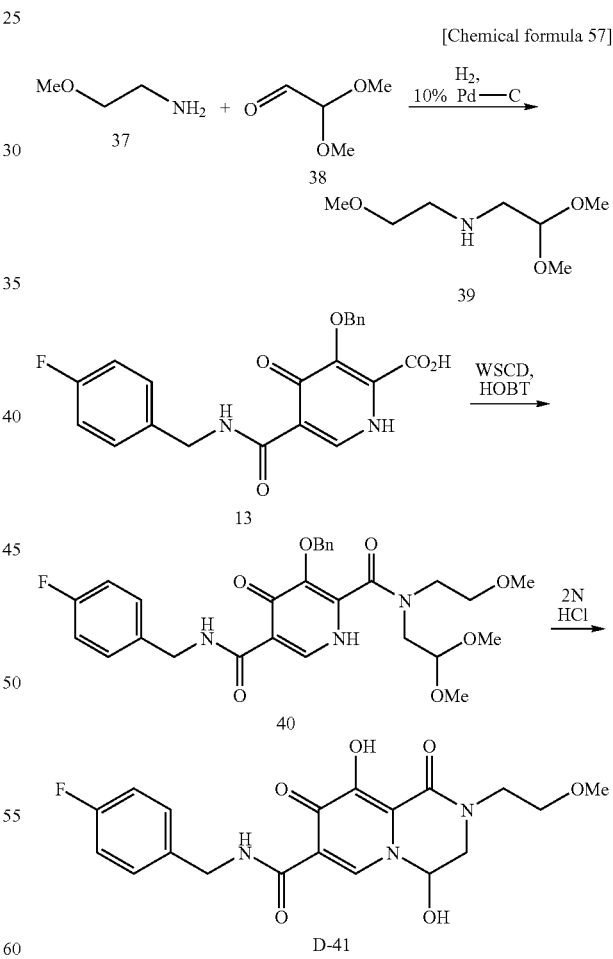

1) To a solution of 2-methoxyethylamine 37 (869 ul, 10 mmol) in methanol (2.6 ml) were added a solution of glyoxal-1,1-dimethylacetal 38 in t-butyl methyl ether (2.57 ml, 10 mmol), and 10% palladium carbon (100 mg), and the mixture was stirred for 1 hour under the hydrogen atmosphere. A catalyst was filtered, and the solvent was distilled off under reduced pressure to obtain a compound 39 (1.26 g).

1H-NMR (CDCl$_3$) δ: 2.76 (2H, d, J=5.6 Hz), 2.81 (2H, t, J=5.2 Hz), 3.36 (3H, s), 3.39 (6H, s), 3.49 (2H, d, J=5.2 Hz), 4.48 (1H, t, J=5.5 Hz).

2) Using a compound 39, a compound 40 was synthesized according to the method of synthesizing a compound 10, and Example D-41 was further obtained according to the method of synthesizing a compound 31.

melting point: 242-243° C.

1H-NMR (DMSO-d$_6$) δ: 3.27 (3H, s), 3.53-3.58 (2H, m), 3.61-3.65 (1H, m), 3.70-3.80 (2H, m), 3.94-3.99 (1H, m), 4.52 (2H, d, J=6.4 Hz), 5.90 (1H, brs), 7.13-7.19 (2H, m), 7.33-7.37 (2H, m), 7.65 (1H, d, J=5.2 Hz), 8.51 (1H, s), 10.36 (1H, t, J=5.9 Hz), 12.46 (1H, brs).

According to the same manner as that of Example D-41, the following Example compounds D-42, D-43, D-45, and D-47 were synthesized.

Example D-42

4,9-Dihydroxy-1,8-dioxo-1,3,4,8-tetrahydro-2H-pyrid[1,2-a]pyrazine-7-carboxylic acid 4-fluoro-benzylamide melting point: 280-282° C.

1H-NMR (DMSO-d$_6$) δ: 3.48 (1H, ddd, J=3.1, 4.5, 13.7 Hz), 3.75 (1H, d, J=11.9 Hz), 4.52 (2H, d, J=6.1 Hz), 5.89 (1H, dd, J=2.4, 5.0 Hz), 7.13-7.20 (2H, m), 7.32-7.38 (2H, m), 7.63 (1H, d, J=5.2 Hz), 8.55 (1H, s), 9.20 (1H, d, J=3.8 Hz), 10.38 (1H, m), 12.57 (1H, s).

Example D-43

4,9-Dihydroxy-2-(3-isopropoxy-propyl)-1,8-dioxo-1,3,4,8-tetrahydro-2H-pyrid[1,2-a]pyrazine-7-carboxylic acid 4-fluoro-benzylamide NMR (DMSO-d$_6$) δ: 1.05 (6H, d, J=6.4 Hz), 1.78 (2H, t, J=6.4 Hz), 3.42-3.66 (6H, m), 3.94-3.97 (1H, m), 4.52 (2H, d, J=5.2 Hz), 5.92 (1H, s), 7.13-7.18 (2H, m), 7.33-7.37 (2H, m), 7.63-7.64 (1H, m), 8.51 (1H, s), 10.37 (1H, t, J=6.0 Hz), 12.56 (1H, s).

Example D-45)

2-Cyclohexylmethyl-4,9-dihydroxy-1,8-dioxo-1,3,4,8-tetrahydro-2H-pyrid[1,2-a]pyrazine-7-carboxylic acid 4-fluoro-benzylamide NMR (DMSO-d$_6$) δ: 0.93-0.99 (2H, m), 1.12-1.22 (3H, m), 1.59-1.74 (6H, m), 3.25-3.30 (1H, m), 3.40-3.45 (1H, m), 3.64-3.68 (1H, m), 3.93-3.96 (1H, m), 4.52 (2H, d, J=6.0 Hz), 5.92 (1H, s), 7.13-7.18 (2H, m), 7.33-7.37 (2H, m), 7.61 (1H, d, J=4.8 Hz), 8.51 (1H, s), 10.37 (1H, t, J=6.0 Hz), 12.59 (1H, s).

Example D-47

2-(4-Fluoro-benzyl)-4,9-dihydroxy-1,8-dioxo-1,3,4,8-tetrahydro-2H-pyrid[1,2-a]pyrazine-7-carboxylic acid 4-fluoro-benzylamide NMR (DMSO-d$_6$) δ: 3.63-3.66 (1H, m), 3.91-3.94 (1H, m), 4.53 (2H, d, J=4.4 Hz), 4.73 (2H, dd, J=18.4, 15.2 Hz), 5.93 (1H, s), 7.13-7.22 (4H, m), 7.34-7.37 (2H, m), 7.43-7.46 (2H, m), 7.64 (1H, s), 8.51 (1H, s), 10.35 (1H, t, J=5.6 Hz), 12.38 (1H, s).

After amine used in the step 2) of synthesizing a compound 10 was changed to 2-chloro-3-fluoro-benzylamine, the following Example compounds D-42, D-44, and D-46 were synthesized according to the method of synthesizing Example D-39.

Example D-44

4,9-Dihydroxy-2-(3-isopropoxy-propyl)-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 1.05 (6H, d, J=6.0 Hz), 1.78 (2H, t, J=6.4 Hz), 3.42-3.66 (6H, m), 3.94-3.97 (1H, m), 4.62 (2H, d, J=6.0 Hz), 5.92 (1H, s), 7.18-7.22 (1H, m), 7.29-7.33 (1H, m), 7.48-7.51 (1H, m), 7.63-7.64 (1H, m), 8.50 (1H, s), 10.40 (1H, t, J=5.6 Hz), 12.58 (1H, s).

Example D-46

2-Cyclohexylmethyl-4,9-dihydroxy-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 0.94-0.98 (2H, m), 1.12-1.22 (3H, m), 1.62-1.73 (6H, m), 3.22-3.27 (1H, m), 3.40-3.45 (1H, m), 3.63-3.67 (1H, m), 3.92-3.96 (1H, m), 4.62 (2H, d, J=5.6 Hz), 5.91 (1H, s), 7.18-7.22 (1H, m), 7.29-7.33 (1H, m), 7.48-7.51 (1H, m), 7.60 (1H, d, J=4.8 Hz), 8.49 (1H, s), 10.42 (1H, t, J=5.6 Hz), 12.60 (1H, s).

Example D-48

2-(4-Fluoro-benzyl)-4,9-dihydroxy-1,8-dioxo-1,3,4,8-tetrahydro-2H-pyrid[1,2-a]pyrazine-7-carboxylic acid 2-chloro-3-fluoro-benzylamide NMR (DMSO-d$_6$) δ: 3.59-3.66 (1H, m), 3.84-3.92 (1H, m), 4.62 (2H, d, J=5.6 Hz), 4.72 (2H, d, J=15.2 Hz), 5.92 (1H, s), 7.17-7.22 (3H, m), 7.30-7.33 (1H, m), 7.43-7.51 (3H, m), 7.65 (1H, s), 8.49 (1H, s), 10.40 (1H, t, J=5.6 Hz), 12.38 (1H, brs).

Example D-49

5,9-Dihydroxy-6,10-dioxo-1,2,3,4,6,9,9a,10-octahydro-2,4-a,8a-triaza-anthracene-7-carboxylic acid 4-fluorobenzylamide 1H-NMR (DMSO-d$_6$) δ: 2.58-2.65 (1H, m), 2.70-3.20 (4H, m), 3.19-3.23 (1H, m), 3.65-3.70 (0.5H, m), 3.80-3.90 (0.5H, m), 4.13 (0.5H, d, J=12.4 Hz), 4.24 (0.5H, d, J=12.4 Hz), 4.47-4.54 (2H, m), 5.50 (0.5H, brs), 5.80 (0.5H, brs), 7.15 (1H, t, J=8.4 Hz), 7.33-7.36 (2H, m), 7.56 (0.5H, brs), 8.17 (0.5H, brs), 8.45 (0.5H, s), 8.58 (0.5H, s), 10.35-10.39 (1H, m).

Example E-1

3,9-Dihydroxy-2-(2-methoxy-ethyl)-1,8-dioxo-1,3,4,8-tetrahydro-2H-pyrid[1,2-a]pyrazine-7-carboxylic acid 4-fluoro-2-methoxymethyl-benzylamide

[Chemical formula 58]

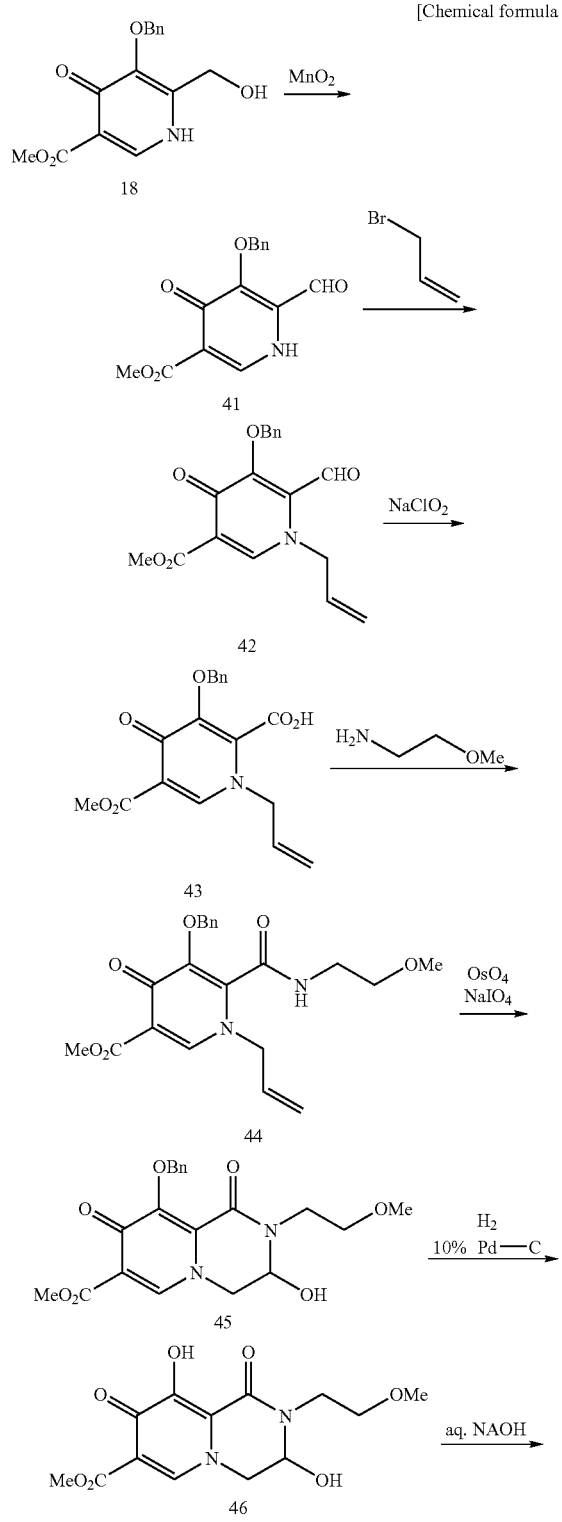

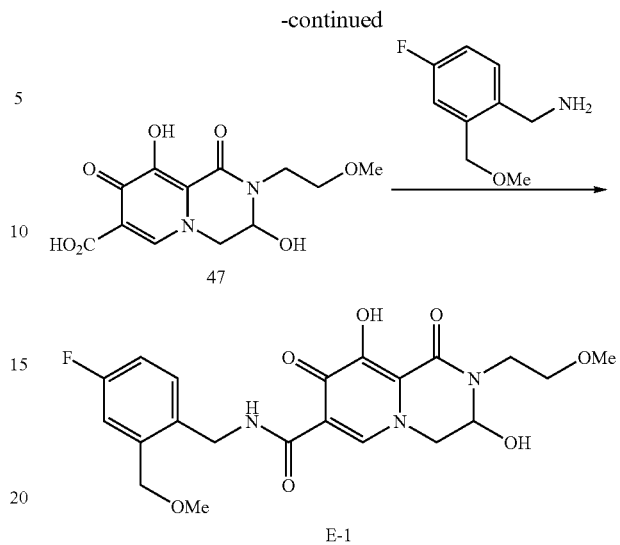

1) According to the method of the step 10) of Example A-1, and from a compound 18 (100 g), a compound 41 was obtained as a pale yellow crystal (77.6 g) at a yield of 78%.

1H-NMR (DMSO-d$_6$) δ: 3.75 (3H, s), 5.36 (2H, s), 7.34-7.46 (5H, m), 8.10 (1H, s), 9.88 (1H, s), 12.05 (1H, br s).

2) According to the method of the step 13) of Example A-1, and from a compound 41 (77 g), a compound 42 was obtained as a pale brown solid (80.3 g) at a yield of 92%.

1H-NMR (CDCl$_3$) δ: 3.95 (3H, s), 4.86 (2H, dt, J=5.2, 1.4 Hz), 4.96 (1H, d, J=17.1 Hz), 5.21 (1H, d, J=10.5 Hz), 5.55 (2H, s), 5.77-5.91 (1H, m), 7.32-7.39 (5H, m), 8.12 (1H, s), 10.00 (1H, s).

3) According to the method of the step 11) of Example A-1, and from a compound 42 (53.2 g), a compound 43 was obtained as a colorless crystal (36.1 g) at a yield of 65%.

1H-NMR (DMSO-d$_6$) δ: 3.75 (3H, s), 4.65 (2H, d, J=5.6 Hz), 5.08 (2H, s), 5.17 (1H, dd, J=17.0, 1.1 Hz), 5.29 (1H, dd, J=10.5, 1.1 Hz), 5.96 (1H, ddt, J=17.0, 10.5, 5.6 Hz), 7.29-7.44 (5H, m), 8.36 (1H, s), 14.78 (1H, br s).

4) According to the method of the step 21) of Example A-9, and from a compound 43 (50 g), a compound 44 was obtained as a colorless crystal (54 g) at a yield of 92%.

1H-NMR (CDCl$_3$) δ: 3.25 (3H, s), 3.34-3.46 (4H, m), 3.87 (3H, s), 4.58 (2H, d, J=6.0 Hz), 5.13 (2H, s), 5.27 (1H, d, J=16.8 Hz), 5.33 (1H, dd, J=10.5, 0.9 Hz), 5.95 (1H, ddt, J=16.8, 10.5, 6.0 Hz), 7.29-7.39 (5H, m), 7.40 (1H, br s), 8.04 (1H, s).

5) According to the method of the step 14) of Example A-1, and from a compound 44 (53.5 g), a compound 45 was obtained as a colorless crystal (45.0 g) at a yield of 84%.

1H-NMR (CDCl$_3$) δ: 3.13-3.22 (1H, m), 3.45-3.50 (1H, m), 3.59-3.69 (1H, m), 3.71 (3H, s), 3.91 (3H, s), 4.07 (1H, dd, J=12.8, 2.1 Hz), 4.26 (1H, dd, J=12.5, 2.1 Hz), 4.40 (1H, dt, J=13.9, 2.7 Hz), 5.04 (1H, t, J=2.1 Hz), 5.19 (1H, d, J=9.9 Hz), 5.42 (1H, d, J=9.9 Hz), 7.29-7.38 (3H, m), 7.65-7.68 (2H, m), 8.10 (1H, s).

6) According to the method of the step 17) of Example B-1, and from a compound 45 (1.61 g), a crude product (2.50 g) of a compound 46 was obtained.

7) According to the method of the step 8) of Example A-1, and from a crude product (2.50 g) of a compound 46, a compound 47 was obtained as a colorless crystal (607 mg) at a yield of 54%.

1H-NMR (DMSO-$d_6$) δ: 3.29 (3H, s), 3.45-3.63 (3H, m), 3.90-3.99 (1H, m), 4.40 (1H, dd, J=13.9, 1.8 Hz), 4.60 (1H, dd, J=13.8, 2.1 Hz), 5.36-5.38 (1H, m), 7.04 (1H, d, J=6.6 Hz), 8.68 (1H, s), 12.48 (1H, brs).

8) According to the method of the step 21) of Example A-9, and from a compound 47 (149 mg), Example E-1 was obtained as a colorless crystal (92 mg) at a yield of 41%.

melting point: 175-177° C.

1H-NMR (DMSO-$d_6$) δ: 3.29 (3H, s), 3.34 (3H, s), 3.40-3.60 (3H, m), 3.89-3.95 (1H, m), 4.29-4.35 (1H, m), 4.48-4.54 (5H, m), 5.32 (1H, d, J=6.3 Hz), 6.94 (1H, d, J=6.3 Hz), 7.08-7.20 (2H, m), 7.32-7.37 (1H, m), 8.49 (1H, s), 10.33 (1H, t, J=5.9 Hz), 12.15 (1H, brs).

According to the same manner as that of Example E-1, the following Example compounds E-2 to E-22 were synthesized.

Example E-2

3,9-Dihydroxy-2-(2-methoxy-ethyl)-1,8-dioxo-1,3,4,8-tetrahydro-2H-pyrid[1,2-a]pyrazine-7-carboxylic acid 4-fluoro-2-trifluoromethyl-benzylamide melting point: 240-241° C.

NMR (DMSO-$d_6$) δ: 3.24 (3H, s), 3.44-3.61 (3H, m), 3.90-3.96 (1H, m), 4.31-4.34 (1H, m), 4.48-4.51 (1H, m), 4.69 (2H, d, J=5.6 Hz), 5.32 (1H, d, J=6.0 Hz), 6.93 (1H, d, J=6.0 Hz), 7.52-7.65 (3H, m), 8.48 (1H, s), 10.50 (1H, t, J=6.0 Hz), 12.17 (1H, brs).

Example E-3

3,9-Dihydroxy-2-(2-methoxy-ethyl)-1,8-dioxo-1,3,4,8-tetrahydro-2H-pyrid[1,2-a]pyrazine-7-carboxylic acid 4-fluoro-3-trifluoromethyl-benzylamide melting point: 223-224° C.

NMR (DMSO-$d_6$) δ: 3.24 (3H, s), 3.44-3.61 (3H, m), 3.90-3.96 (1H, m), 4.30-4.33 (1H, m), 4.48-4.51 (1H, m), 4.59 (2H, d, J=6.0 Hz), 5.32 (1H, d, J=6.4 Hz), 6.93 (1H, d, J=6.0 Hz), 7.45-7.50 (1H, m), 7.68-7.74 (2H, m), 8.50 (1H, s), 10.47 (1H, t, J=6.0 Hz), 12.19 (1H, s).

Example E-4

3,9-Dihydroxy-2-(2-methoxy-ethyl)-1,8-dioxo-1,3,4,8-tetrahydro-2H-pyrid[1,2-a]pyrazine-7-carboxylic acid 2-difluoromethoxy-benzylamide melting point: 220-221° C.

NMR (DMSO-$d_6$) δ: 3.29 (3H, s), 3.40-3.62 (3H, m), 3.90-3.98 (1H, m), 4.33 (1H, d, J=12.4 Hz), 4.50 (1H, d, J=12.4 Hz), 4.57 (1H, d, J=6.0 Hz), 5.33 (1H, d, J=6.0 Hz), 6.93 (1H, d, J=6.4 Hz), 7.07-7.47 (5H, m), 8.49 (1H, s), 10.42 (1H, t, J=6.0 Hz), 12.18 (1H, s).

Example E-5

3,9-Dihydroxy-2-(2-methoxy-ethyl)-1,8-dioxo-1,3,4,8-tetrahydro-2H-pyrid[1,2-a]pyrazine-7-carboxylic acid 2-methoxy-benzylamide NMR (DMSO-$d_6$) δ: 3.29 (3H, s), 3.41-3.60 (3H, m), 3.84 (3H, s), 3.91-3.94 (1H, m), 4.31 (1H, d, J=13.2 Hz), 4.47-4.51 (3H, m), 5.31 (1H, d, J=6.0 Hz), 6.86-6.96 (2H, m), 7.02 (1H, d, J=8.0 Hz), 7.20 (1H, d, J=7.2 Hz), 7.25-7.28 (1H, m), 8.47 (1H, s), 10.34-10.36 (1H, m), 12.15 (1H, s).

Example E-6

3,9-Dihydroxy-2-(2-methoxy-ethyl)-1,8-dioxo-1,3,4,8-tetrahydro-2H-pyrid[1,2-a]pyrazine-7-carboxylic acid 4-methoxy-benzylamide NMR (DMSO-$d_6$) δ3.29 (3H, s), 3.44-3.60 (3H, m), 3.73 (3H, s), 3.90-3.94 (1H, m), 4.32 (1H, d, J=12.4 Hz), 4.45-4.51 (3H, m), 5.32 (1H, d, J=6.4 Hz), 6.90 (2H, d, J=8.4 Hz), 6.93 (1H, d, J=5.6 Hz), 7.24 (2H, d, J=8.4 Hz), 8.49 (1H, s), 10.33-10.34 (1H, m), 12.14 (1H, s).

Example E-7

3,9-Dihydroxy-2-(2-methoxy-ethyl)-1,8-dioxo-1,3,4,8-tetrahydro-2H-pyrid[1,2-a]pyrazine-7-carboxylic acid 2-trifluoromethoxy-benzylamide NMR (DMSO-$d_6$) δ: 3.29 (3H, s), 3.50-3.60 (3H, m), 3.82-3.95 (1H, m), 4.26 (1H, d, J=13.2 Hz), 4.41 (1H, d, J=12.0 Hz), 4.61 (2H, d, J=4.8 Hz), 5.27 (1H, s), 6.98-7.10 (1H, m), 7.36-7.48 (4H, m), 8.26 (1H, s), 10.58 (1H, s), 12.20 (1H, s).

Example E-8

3,9-Dihydroxy-2-(2-methoxy-ethyl)-1,8-dioxo-1,3,4,8-tetrahydro-2H-pyrid[1,2-a]pyrazine-7-carboxylic acid 3-trifluoromethoxy-benzylamide NMR (DMSO-$d_6$) δ: 3.29 (3H, s), 3.45-3.62 (3H, m), 3.90-3.96 (1H, m), 4.33 (1H, d, J=12.4 Hz), 4.51 (1H, d, J=13.2 Hz), 4.60 (2H, d, J=6.0 Hz), 5.33 (1H, d, J=6.0 Hz), 6.95 (1H, d, J=6.0 Hz), 7.25 (1H, d, J=8.0 Hz), 7.29 (1H, s), 7.35 (1H, d, J=8.0 Hz), 7.48 (1H, t, J=8.0 Hz), 8.51 (1H, s), 10.48 (1H, t, J=6.0 Hz), 12.20 (1H, s).

Example E-9

3,9-Dihydroxy-2-(2-methoxy-ethyl)-1,8-dioxo-1,3,4,8-tetrahydro-2H-pyrid[1,2-a]pyrazine-7-carboxylic acid 4-trifluoromethoxy-benzylamide NMR (DMSO-$d_6$) δ: 3.29 (3H, s), 3.45-3.62 (3H, m), 3.91-3.96 (1H, m), 4.34 (1H, d, J=13.2 Hz), 4.52 (1H, d, J=13.6 Hz), 4.58 (2H, d, J=5.6 Hz), 5.34 (1H, d, J=5.2 Hz), 6.95 (1H, d, J=6.0 Hz), 7.33 (2H, d, J=8.0 Hz), 7.45 (2H, d, J=8.0 Hz), 8.52 (1H, s), 10.47 (1H, t, J=6.0 Hz), 12.20 (1H, s).

Example E-10

3,9-Dihydroxy-2-(2-methoxy-ethyl)-1,8-dioxo-1,3,4,8-tetrahydro-2H-pyrid[1,2-a]pyrazine-7-carboxylic acid 2-trifluoromethyl-benzylamide NMR (DMSO-$d_6$) δ: 3.29 (3H, s), 3.45-3.62 (3H, m), 3.90-3.96 (1H, m), 4.33 (1H, d, J=12.4 Hz), 4.51 (1H, d, J=13.2

Hz), 4.73 (2H, d, J=5.6 Hz), 5.32 (1H, s), 6.94 (1H, s), 7.50 (1H, t, J=7.6 Hz), 7.55 (1H, d, J=8.0 Hz), 7.66 (1H, t, J=8.0 Hz), 7.75 (1H, d, J=8.0 Hz), 8.50 (1H, s), 10.51 (1H, t, J=6.0 Hz), 12.13 (1H, s).

Example E-11

3,9-Dihydroxy-2-(2-methoxy-ethyl)-1,8-dioxo-1,3,4, 8-tetrahydro-2H-pyrid[1,2-a]pyrazine-7-carboxylic acid 3-trifluoromethyl-benzylamide NMR (DMSO-$d_6$) δ: 3.29 (3H, s), 3.46-3.61 (3H, m), 3.90-3.96 (1H, m), 4.32 (1H, d, J=13.6 Hz), 4.50 (1H, d, J=12.8 Hz), 4.64 (2H, d, J=6.0 Hz), 5.32 (1H, d, J=6.0 Hz), 6.94 (1H, d, J=5.6 Hz), 7.54-7.67 (4H, m), 8.51 (1H, s), 10.49 (1H, t, J=6.0 Hz), 12.19 (1H, s).

Example E-12

3,9-Dihydroxy-2-(2-methoxy-ethyl)-1,8-dioxo-1,3,4, 8-tetrahydro-2H-pyrid[1,2-a]pyrazine-7-carboxylic acid 4-trifluoromethyl-benzylamide NMR (DMSO-$d_6$) δ: 3.29 (3H, s), 3.44-3.62 (3H, m), 3.90-3.96 (1H, m), 4.33 (1H, d, J=12 Hz), 4.50 (1H, d, J=13.2 Hz), 4.64 (2H, d, J=6.0 Hz), 5.32 (1H, d, J=6.0 Hz), 6.95 (1H, d, J=6.4 Hz), 7.52 (2H, d, J=7.6 Hz), 7.70 (2H, d, J=8.0 Hz), 8.50 (1H, s), 10.51 (1H, t, J=6.0 Hz), 12.20 (1H, s).

Example E-13

3,9-Dihydroxy-2-(2-methoxy-ethyl)-1,8-dioxo-1,3,4, 8-tetrahydro-2H-pyrid[1,2-a]pyrazine-7-carboxylic acid 2-ethoxy-benzylamide NMR (DMSO-$d_6$) δ: 3.29 (3H, s), 3.44-3.61 (3H, m), 3.90-3.96 (1H, m), 4.09 (2H, q, J=6.8 Hz), 4.31 (1H, d, J=12.4 Hz), 4.48-4.51 (3H, m), 5.32 (1H, s), 6.87-6.97 (2H, m), 6.99 (1H, d, J=8.0 Hz), 7.20-7.26 (2H, m), 8.47 (1H, s), 10.38 (1H, t, J=6.0 Hz), 12.06 (1H, brs).

Example E-14

3,9-Dihydroxy-2-(2-methoxy-ethyl)-1,8-dioxo-1,3,4, 8-tetrahydro-2H-pyrid[1,2-a]pyrazine-7-carboxylic acid 2,4-dimethoxy-benzylamide NMR (DMSO-$d_6$) δ: 3.29 (3H, s), 3.44-3.61 (3H, m), 3.75 (3H, s), 3.83 (3H, s), 3.90-3.96 (1H, m), 4.31 (1H, d, J=12.8 Hz), 4.40 (2H, d, J=5.6 Hz), 4.49 (1H, d, J=12.8 Hz), 5.32 (1H, d, J=6.0 Hz), 6.47 (1H, dd, J=2.4, 8.4 Hz), 7.52 (2H, d, J=7.6 Hz), 6.58-6.59 (1H, m), 6.93 (1H, d, J=6.0 Hz), 7.12 (1H, d, J=8.0 Hz), 8.47 (1H, s), 10.27 (1H, t, J=5.6 Hz), 12.14 (1H, s).

Example E-15

3,9-Dihydroxy-2-(2-methoxy-ethyl)-1,8-dioxo-1,3,4, 8-tetrahydro-2H-pyrid[1,2-a]pyrazine-7-carboxylic acid 4-methoxymethyl-benzylamide NMR (DMSO-$d_6$) δ: 3.28 (3H, s), 3.42-3.60 (3H, m), 3.88-3.93 (1H, m), 4.23 (1H, d, J=12.8 Hz), 4.38-4.41 (3H, m), 5.26-5.29 (3H, m), 6.92 (1H, d, J=6.0 Hz), 7.32 (2H, d, J=7.6 Hz), 7.45 (2H, d, J=7.6 Hz), 8.35 (1H, s), 12.10 (1H, brs).

Example E-16

3,9-Dihydroxy-2-(2-methoxy-ethyl)-1,8-dioxo-1,3,4, 8-tetrahydro-2H-pyrid[1,2-a]pyrazine-7-carboxylic acid 4-tertiary-butyl-benzylamide NMR (DMSO-$d_6$) δ: 1.27 (9H, s), 3.29 (3H, s), 3.44-3.61 (3H, m), 3.90-3.96 (1H, m), 4.33 (1H, d, J=11.6 Hz), 4.49-4.52 (3H, m), 5.32 (1H, s), 6.94 (1H, s), 7.24 (2H, d, J=8.4 Hz), 7.35 (2H, d, J=8.4 Hz), 8.50 (1H, s), 10.37 (1H, t, J=6.0 Hz), 12.16 (1H, s).

Example E-17

3,9-Dihydroxy-2-(2-methoxy-ethyl)-1,8-dioxo-1,3,4, 8-tetrahydro-2H-pyrid[1,2-a]pyrazine-7-carboxylic acid 3-chloro-2-fluoro-benzylamide NMR (DMSO-$d_6$) δ: 3.29 (3H, s), 3.44-3.62 (3H, m), 3.90-3.96 (1H, m), 4.32 (1H, d, J=11.6 Hz), 4.50 (1H, d, J=12.4 Hz), 4.62 (2H, d, J=5.6 Hz), 5.32 (1H, s), 6.95 (1H, s), 7.20 (1H, t, J=8.0 Hz), 7.32 (1H, t, J=7.2 Hz), 7.50 (1H, t, J=8.0 Hz), 8.49 (1H, s), 10.46 (1H, t, J=6.0 Hz), 12.06 (1H, s).

Example E-18

3,9-Dihydroxy-2-(2-methoxy-ethyl)-1,8-dioxo-1,3,4, 8-tetrahydro-2H-pyrid[1,2-a]pyrazine-7-carboxylic acid 2,4-difluoro-benzylamide NMR (DMSO-$d_6$) δ: 3.29 (3H, s), 3.44-3.61 (3H, m), 3.90-3.96 (1H, m), 4.32 (1H, d, J=12.4 Hz), 4.50 (1H, d, J=13.6 Hz), 4.55 (2H, d, J=5.6 Hz), 5.32 (1H, d, J=6.4 Hz), 6.94 (1H, d, J=6.4 Hz), 7.03-7.09 (1H, m), 7.21-7.27 (1H, m), 7.38-7.44 (1H, m), 8.49 (1H, s), 10.41 (1H, t, J=6.0 Hz), 12.18 (1H, s).

Example E-19

3,9-Dihydroxy-2-(2-methoxy-ethyl)-1,8-dioxo-1,3,4, 8-tetrahydro-2H-pyrid[1,2-a]pyrazine-7-carboxylic acid 4-fluoro-2-methanesulfonylamino-benzylamide NMR (DMSO-$d_6$) δ: 3.08 (3H, s), 3.28 (3H, s), 3.43-3.61 (3H, m), 3.90-3.95 (1H, m), 4.31 (1H, d, J=12.0 Hz), 4.50-4.57 (3H, m), 5.32 (1H, d, J=6.0 Hz), 6.95 (1H, d, J=6.0 Hz), 7.03-7.07 (1H, m), 7.18-7.22 (1H, m), 7.47-7.50 (1H, m), 8.52 (1H, s), 10.57 (1H, t, J=6.0 Hz), 12.21 (1H, s).

Example E-20

3,9-Dihydroxy-2-(2-methoxy-ethyl)-1,8-dioxo-1,3,4, 8-tetrahydro-2H-pyrid[1,2-a]pyrazine-7-carboxylic acid 4-fluoro-2-methoxy-benzylamide NMR (DMSO-$d_6$) δ: 3.29 (3H, s), 3.44-3.61 (3H, m), 3.86 (3H, s), 3.90-3.96 (1H, m), 4.32 (1H, d, J=12.0 Hz), 4.44 (2H, d, J=6.0 Hz), 4.49 (1H, d, J=12.8 Hz), 5.32 (1H, d, J=5.2 Hz), 6.70-6.75 (1H, m), 6.91-6.95 (2H, m), 7.22 (1H, t, J=7.6 Hz), 8.47 (1H, s), 10.35 (1H, t, J=6.0 Hz), 12.16 (1H, s).

Example E-21

3,9-Dihydroxy-2-(2-methoxy-ethyl)-1,8-dioxo-1,3,4, 8-tetrahydro-2H-pyrid[1,2-a]pyrazine-7-carboxylic acid 4-fluoro-3-methoxy-benzylamide NMR (DMSO-$d_6$) δ: 3.29 (3H, s), 3.45-3.62 (3H, m), 3.82 (3H, s), 3.90-3.96 (1H, m), 4.33 (1H, d, J=13.2 Hz), 4.50-4.52 (3H, m), 5.32 (1H, s), 6.85-6.89 (1H, m), 6.96 (1H, d, J=6.0 Hz), 7.13-7.18 (2H, m), 8.51 (1H, s), 10.42 (1H, t, J=6.8 Hz), 12.18 (1H, s).

Example E-22

3,9-Dihydroxy-2-(2-methoxy-ethyl)-1,8-dioxo-1,3,4,8-tetrahydro-2H-pyrid[1,2-a]pyrazine-7-carboxylic acid 4-fluoro-3-methoxymethyl-benzylamide NMR (DMSO-$d_6$) δ: 3.29 (3H, s), 3.30 (3H, s), 3.45-3.62 (3H, m), 3.91-3.96 (1H, m), 4.33 (1H, d, J=13.2 Hz), 4.44 (2H, s), 4.50-4.54 (3H, m), 5.33 (1H, s), 6.95 (1H, s), 7.13-7.17 (2H, m), 7.28-7.32 (1H, m), 7.37-7.39 (1H, m), 8.51 (1H, s), 10.42 (1H, t, J=6.0 Hz), 12.18 (1H, s).

Example G-1

9-Hydroxy-2-(2-methoxy-ethyl)-1,8-dioxo-1,3,4,8-tetrahydro-2H-pyrid[1,2-a]pyrazine-7-carboxylic acid 4-fluoro-3-methoxy-benzylamide

[Chemical formula 60]

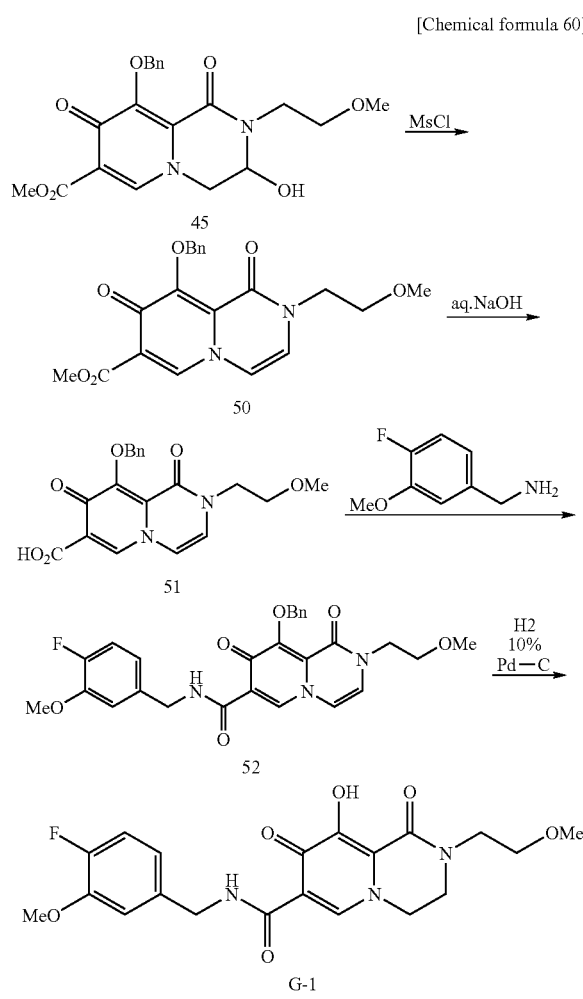

1) To a solution of a compound 45 (25 g, 62.1 mmol) in tetrahydrofuran (375 ml) were added triethylamine (21.6 ml, 155 mmol) and methanesulfonyl chloride (5.8 ml, 74.5 mmol) under ice-cooling, and the mixture was stirred at room temperature for 1 hour. Triethylamine (4.3 ml, 31.1 mmol) and methanesulfonyl chloride (1.45 ml, 18.6 mmol) were further added, and the mixture was further stirred for 30 minutes. Water was added to the reaction solution, followed by extraction with ethyl acetate. The organic layer was dried with anhydrous sodium sulfate, and the solvent was distilled off under reduced pressure. The residue was washed with ether to obtain a crude product (31 g). Recrystallization with acetone and diisopropyl ether afforded a compound 50 (21.5 g) at a yield of 90%.

2) According to the method of Example A-18), and from a compound 50 (14 g), a crystal (12.2 g) of a compound 51 was obtained at a yield of 90%.

3) According to the method of synthesizing a compound 21, and from a compound 51 (250 mg), a compound 52 (207 mg) was obtained at a yield of 60%.

4) According to the method of synthesizing Example B-1, and from a compound 52 (207 mg), a compound G-1 (102 mg) was obtained at a yield of 60%.

melting point: 197° C.

NMR (DMSO-$d_6$) δ: 3.28 (3H, s), 3.54-3.57 (2H, m), 3.67-3.69 (2H, m), 3.79-3.82 (5H, m), 4.35-4.38 (2H, m), 4.50 (2H, d, J=6.0 Hz), 6.83-6.89 (1H, m), 7.12-7.18 (2H, m), 8.40 (1H, s), 10.37-10.47 (1H, m), 12.42 (1H, s).

According to the same manner as that of Example G-1, the following Example compounds G-2 to G-15 were synthesized.

Example G-2

9-Hydroxy-2-(2-methoxy-ethyl)-1,8-dioxo-1,3,4,8-tetrahydro-2H-pyrid[1,2-a]pyrazine-7-carboxylic acid 4-fluoro-2-trifluoromethyl-benzylamide melting point: 276° C.

NMR (DMSO-$d_6$) δ: 3.27 (3H, s), 3.53-3.57 (2H, m), 3.66-3.70 (2H, m), 3.77-3.81 (2H, m), 4.34-4.38 (2H, m), 4.68 (2H, d, J=6.4 Hz), 7.54-7.56 (3H, m), 8.37 (1H, brs), 10.54-10.55 (1H, m), 12.44 (1H, s).

Example G-3

9-Hydroxy-2-(2-methoxy-ethyl)-1,8-dioxo-1,3,4,8-tetrahydro-2H-pyrid[1,2-a]pyrazine-7-carboxylic acid 4-fluoro-3-trifluoromethyl-benzylamide melting point: 225° C.

NMR (DMSO-$d_6$) δ: 3.27 (3H, s), 3.55 (2H, t, J=5.6 Hz), 3.68 (2H, t, J=5.2 Hz), 3.78-3.81 (2H, m), 4.35-4.38 (2H, m), 4.59 (2H, d, J=6.0 Hz), 7.46-7.50 (1H, m), 7.67-7.73 (2H, m), 8.41 (1H, s), 10.52 (1H, t, J=6.0 Hz), 12.45 (1H, s).

Example G-4

9-Hydroxy-2-(2-methoxy-ethyl)-1,8-dioxo-1,3,4,8-tetrahydro-2H-pyrid[1,2-a]pyrazine-7-carboxylic acid 4-methyl-benzylamide melting point: 180° C.

NMR (DMSO-$d_6$) δ: 2.28 (3H, s), 3.28 (3H, s), 3.56 (2H, t, J=5.2 Hz), 3.68 (2H, t, J=5.2 Hz), 3.78-3.82 (2H, m), 4.35-4.39 (2H, m), 4.49 (2H, d, J=5.6 Hz), 7.14 (2H, d, J=8.0 Hz), 7.19 (2H, d, J=7.6 Hz), 8.40 (1H, s), 10.40 (1H, t, J=5.6 Hz), 12.42 (1H, brs).

Example G-5

9-Hydroxy-2-(2-methoxy-ethyl)-1,8-dioxo-1,3,4,8-tetrahydro-2H-pyrid[1,2-a]pyrazine-7-carboxylic acid 2-difluoromethoxy-benzylamide melting point: 201° C.

NMR (DMSO-d$_6$) δ: 3.28 (3H, s), 3.56 (2H, t, J=5.6 Hz), 3.68 (2H, t, J=5.6 Hz), 3.80 (2H, J=5.6 Hz), 4.37 (2H, t, J=5.6 Hz), 4.56 (2H, d, J=5.6 Hz), 7.25 (1H, t, J=74 Hz), 7.20-7.23 (2H, m), 7.33-7.37 (2H, m), 8.40 (1H, s), 10.43 (1H, t, J=5.6 Hz), 12.43 (1H, s).

Example G-6

9-Hydroxy-2-(2-methoxy-ethyl)-1,8-dioxo-1,3,4,8-tetrahydro-2H-pyrid[1,2-a]pyrazine-7-carboxylic acid 2-methoxy-benzylamide melting point: 181° C.

NMR (DMSO-d$_6$) δ: 3.27 (3H, s), 3.56 (2H, t, J=5.2 Hz), 3.68 (2H, t, J=5.2 Hz), 3.80 (2H, t, J=5.6 Hz), 3.84 (3H, s), 4.37 (2H, t, J=5.6 Hz), 4.48 (2H, d, J=5.6 Hz), 6.90 (1H, t, J=7.6 Hz), 7.01 (1H, d, J=8.4 Hz), 7.20 (1H, d, J=7.2 Hz), 7.26 (1H, t, J=7.6 Hz), 8.38 (1H, s), 10.38 (1H, t, J=6.0 Hz), 12.41 (1H, brs).

Example G-7

9-Hydroxy-2-(2-methoxy-ethyl)-1,8-dioxo-1,3,4,8-tetrahydro-2H-pyrid[1,2-a]pyrazine-7-carboxylic acid 3-methoxy-benzylamide melting point: 134° C.

NMR (DMSO-d$_6$) δ: 3.28 (3H, s), 3.56 (2H, t, J=5.2 Hz), 3.68 (2H, t, J=5.2 Hz), 3.73 (3H, s), 3.80 (2H, t, J=5.2 Hz), 4.37 (2H, t, J=5.6 Hz), 4.51 (2H, d, J=5.6 Hz), 6.82-6.89 (3H, m), 7.25 (1H, t, J=8.0 Hz), 8.41 (1H, s), 10.43 (1H, t, J=5.6 Hz), 12.42 (1H, brs).

Example G-8

9-Hydroxy-2-(2-methoxy-ethyl)-1,8-dioxo-1,3,4,8-tetrahydro-2H-pyrid[1,2-a]pyrazine-7-carboxylic acid 4-methoxy-benzylamide melting point: 172° C.

NMR (DMSO-d$_6$) δ: 3.27 (3H, s), 3.56 (2H, t, J=5.2 Hz), 3.68 (2H, t, J=5.2 Hz), 3.73 (3H, s), 3.80 (2H, t, J=5.2 Hz), 4.38 (2H, t, J=5.6 Hz), 4.46 (2H, d, J=5.6 Hz), 6.89 (2H, d, J=8.4 Hz), 7.24 (2H, d, J=8.4 Hz), 8.41 (1H, s), 10.36 (1H, t, J=5.6 Hz), 12.41 (1H, brs).

Example G-9

9-Hydroxy-2-(2-methoxy-ethyl)-1,8-dioxo-1,3,4,8-tetrahydro-2H-pyrid[1,2-a]pyrazine-7-carboxylic acid 2-trifluoromethyl-benzylamide melting point: 251° C.

NMR (DMSO-d$_6$) δ: 3.28 (3H, s), 3.56 (2H, t, J=5.2 Hz), 3.69 (2H, t, J=5.2 Hz), 3.80 (2H, t, J=5.2 Hz), 4.38 (2H, t, J=5.6 Hz), 4.72 (2H, d, J=5.6 Hz), 7.48-7.55 (2H, m), 7.66 (1H, t, J=7.6 Hz), 7.74 (1H, d, J=8.0 Hz), 8.40 (1H, s), 10.49-10.58 (1H, m), 12.44 (1H, s).

Example G-10

9-Hydroxy-2-(2-methoxy-ethyl)-1,8-dioxo-1,3,4,8-tetrahydro-2H-pyrid[1,2-a]pyrazine-7-carboxylic acid 3-trifluoromethyl-benzylamide melting point: 209° C.

NMR (DMSO-d$_6$) δ: 3.28 (3H, s), 3.56 (2H, t, J=5.2 Hz), 3.68 (2H, t, J=5.2 Hz), 3.80 (2H, t, J=5.2 Hz), 4.37 (2H; t, J=5.6 Hz), 4.63 (2H, d, J=6.0 Hz), 7.55-7.66 (4H, m), 8.40 (1H, s), 10.49-10.58 (1H, m), 12.45 (1H, brs).

Example G-11

9-Hydroxy-2-(2-methoxy-ethyl)-1,8-dioxo-1,3,4,8-tetrahydro-2H-pyrid[1,2-a]pyrazine-7-carboxylic acid 4-trifluoromethyl-benzylamide melting point: 240° C.

NMR (DMSO-d$_6$) δ: 3.28 (3H, s), 3.56 (2H, t, J=5.2 Hz), 3.69 (2H, t, J=5.2 Hz), 3.80 (2H, t, J=5.2 Hz), 4.37 (2H, t, J=5.6 Hz), 4.63 (2H, d, J=6.0 Hz), 7.52 (2H, d, J=8.0 Hz), 7.70 (2H, d, J=8.0 Hz), 8.41 (1H, s), 10.54 (1H, t, J=6.0 Hz), 12.44 (1H, s).

Example G-12

9-Hydroxy-2-(2-methoxy-ethyl)-1,8-dioxo-1,3,4,8-tetrahydro-2H-pyrid[1,2-a]pyrazine-7-carboxylic acid 3-trifluoromethoxy-benzylamide melting point: 205° C.

NMR (DMSO-d$_6$) δ: 3.28 (3H, s), 3.56 (2H, t, J=5.2 Hz), 3.68 (2H, t, J=5.2 Hz), 3.80 (2H, t, J=5.2 Hz), 4.37 (2H, t, J=5.6 Hz), 4.59 (2H, d, J=5.6 Hz), 7.24-7.28 (2H, m), 7.33-7.35 (1H, m), 7.43-7.49 (1H, m), 8.41 (1H, s), 10.49-10.52 (1H, m), 12.44 (1H, brs).

Example G-13

9-Hydroxy-2-(2-methoxy-ethyl)-1,8-dioxo-1,3,4,8-tetrahydro-2H-pyrid[1,2-a]pyrazine-7-carboxylic acid 4-trifluoromethoxy-benzylamide melting point: 243° C.

NMR (DMSO-d$_6$) δ: 3.27 (3H, s), 3.55 (2H, t, J=5.4 Hz), 3.68 (2H, t, J=5.3 Hz), 3.80 (2H, t, J=5.3 Hz), 4.37 (2H, t, J=5.6 Hz), 4.56 (2H, d, J=6.1 Hz), 7.32 (2H, d, J=7.9 Hz), 7.43 (2H, d, J=8.9 Hz), 8.40 (1H, s), 10.49 (1H, t, J=5.9 Hz), 12.43 (1H, s).

Example G-14

9-Hydroxy-2-(2-methoxy-ethyl)-1,8-dioxo-1,3,4,8-tetrahydro-2H-pyrid[1,2-a]pyrazine-7-carboxylic acid 2,6-dimethoxy-benzylamide melting point: 228° C.

NMR (DMSO-d$_6$) δ: 3.27 (3H, s), 3.55 (2H, t, J=5.2 Hz), 3.67 (2H, t, J=5.2 Hz), 3.77-3.82 (8H, m), 4.35 (2H, s), 4.50 (2H, d, J=5.6 Hz), 6.69 (2H, d, J=8.4 Hz), 7.24-7.29 (2H, m), 8.35 (1H, s), 10.13 (1H, s), 12.35 (1H, s).

Example G-15

9-Hydroxy-2-(2-methoxy-ethyl)-1,8-dioxo-1,3,4,8-tetrahydro-2H-pyrid[1,2-a]pyrazine-7-carboxylic acid 2-ethoxy-benzylamide melting point: 187° C.

NMR (DMSO-$d_6$) δ: 1.40 (3H, t, J=5.1 Hz), 3.27 (3H, s), 3.55 (2H, t, J=5.2 Hz), 3.68 (2H, t, J=5.2 Hz), 3.80 (2H, t, J=5.2 Hz), 4.09 (2H, q, J=6.8 Hz), 4.36 (2H, t, J=5.2 Hz), 4.48 (2H, d, J=5.6 Hz), 6.88 (1H, d, J=7.6 Hz), 6.99 (1H, d, J=8.0 Hz), 7.19-7.25 (2H, m), 8.38 (1H, s), 10.41 (1H, t, J=5.6 Hz), 12.41 (1H, s).

Example G-16

9-Hydroxy-2-(2-methoxy-ethyl)-1,8-dioxo-1,3,4,8-tetrahydro-2H-pyrid[1,2-a]pyrazine-7-carboxylic acid 2-methoxy-benzylamide NMR (DMSO-$d_6$) δ: 3.27 (3H, s), 3.56 (2H, t, J=5.2 Hz), 3.68 (2H, t, J=5.2 Hz), 3.80 (2H, t, J=5.2 Hz), 3.85 (3H, s), 4.37 (2H, t, J=5.2 Hz), 4.43 (2H, d, J=5.6 Hz), 6.70-6.74 (1H, m), 6.91-6.94 (1H, m), 7.17-7.23 (1H, m), 8.38 (1H, s), 10.37 (1H, t, J=5.6 Hz), 12.41 (1H, s).

Example G-17

9-Hydroxy-2-(2-methoxy-ethyl)-1,8-dioxo-1,3,4,8-tetrahydro-2H-pyrid[1,2-a]pyrazine-7-carboxylic acid 2-methoxymethyl-benzylamide NMR (DMSO-$d_6$) δ: 3.27 (3H, s), 3.34 (3H, s), 3.56 (2H, t, J=5.2 Hz), 3.68 (2H, t, J=5.2 Hz), 3.80 (2H, t, J=5.2 Hz), 3.85 (3H, s), 4.37 (2H, t, J=5.2 Hz), 4.50-4.53 (4H, m), 7.08-7.13 (1H, m), 7.16-7.19 (1H, m), 7.32-7.36 (1H, m), 8.40 (1H, s), 10.36 (1H, t, J=5.6 Hz), 12.42 (1H, s).

Example J-1) 2—

(4-Fluorobenzyl)-9-hydroxy-1,3,8-trioxo-1,3,4,8-tetrahydro-2H-pyrid[1,2-a]pyrazine-7-carboxylic acid 4-fluorobenzylamide

[Chemical formula 63]

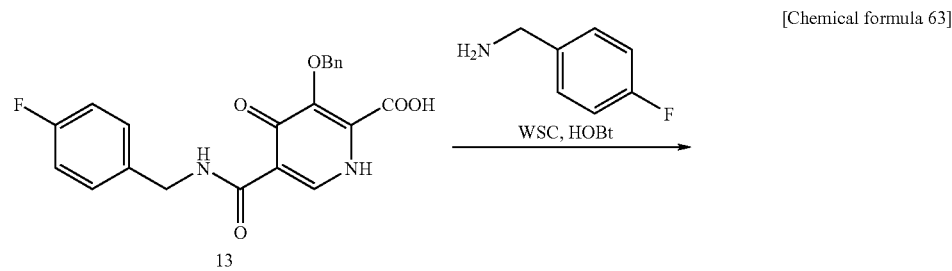

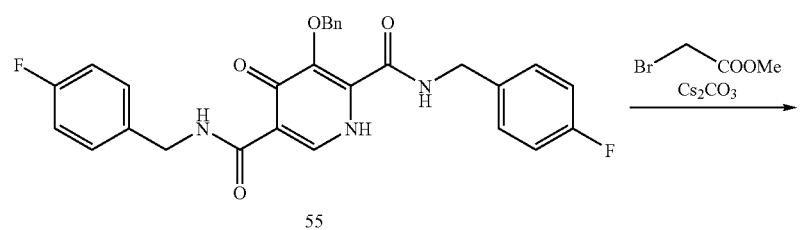

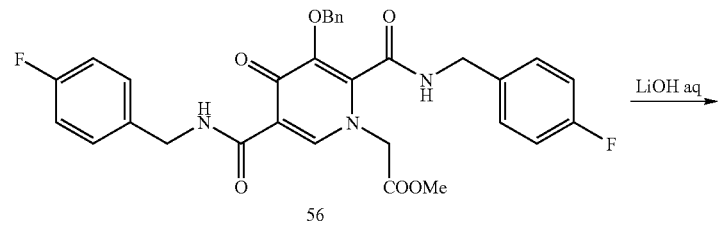

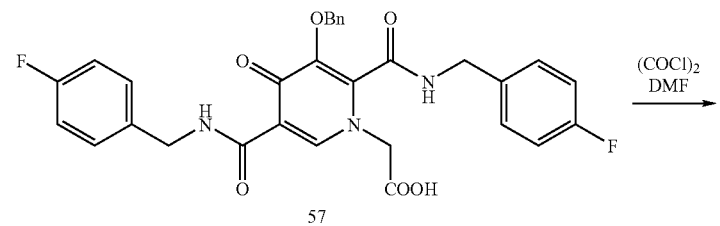

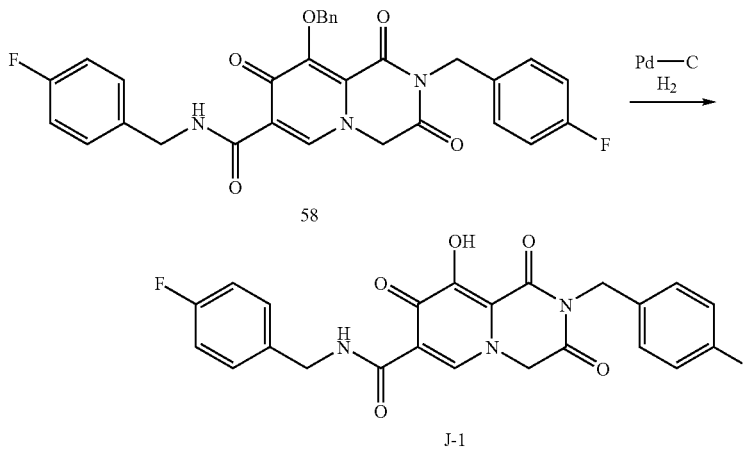

1) According to the method of the step 21, a compound 55 (1.35 g) was obtained at a yield of 71% from a compound 13 (1.50 g, 3.78 mmol).

NMR (DMSO-$d_6$) δ: 4.43 (2H, d, J=6.0 Hz), 4.52 (2H, d, J=6.0 Hz), 5.36 (2H, s), 7.10-7.41 (13H, m), 8.32 (1H, s), 8.94 (2H, t, J=6.0 Hz), 10.47 (1H, t, J=6.0 Hz), 12.36 (1H, s).

2) According to the method of the step 13, a compound 56 (330 mg) was obtained at a yield of 57% from a compound 55 (503 mg, 1.00 mmmol).

NMR (CDCl$_3$) δ: 3.68 (3H, s), 4.30 (2H, d, J=6.0 Hz), 4.57 (2H, d, J=5.7 Hz), 4.88 (2H, s), 5.21 (2H, s), 6.93 (2H, t, J=8.7 Hz), 7.01 (2H, t, J=8.7 Hz), 7.11 (2H, dd, J=5.4 Hz, 8.7 Hz, 2H), 7.25-7.35 (7H, m), 8.37 (1H, s), 10.33 (1H, s).

3) To a solution of a compound 56 (230 mg, 0.400 mmol) in tetrahydrofuran (4.5 ml) was added a 1N aqueous lithium hydroxide solution (0.48 ml) at room temperature, and this was stirred for 3 hours as it was. 2N hydrochloric acid was added, this was extracted with ethyl acetate and the organic layer was washed with an aqueous saturated sodium chloride solution. This was dried with anhydrous sodium sulfate, and the solvent was distilled off under reduced pressure to obtain a compound 57 (216 mg) at a yield of 96%.

NMR (DMSO-$d_6$) δ: 4.38 (2H, d, J=5.7 Hz), 4.53 (2H, d, J=6.0 Hz), 4.86 (2H, s), 5.10 (2H, s), 6.97 (2H, t, J=9.0 Hz), 7.16 (2H, t, J=9.0 Hz), 7.26-7.40 (9H, m), 8.59 (1H, s), 9.46 (1H, t, J=6.0 Hz), 10.43 (1H, t, J=6.0 Hz).

4) To a solution of the compound 57 (183 mg, 0.326 mmol) in dichloromethane (6.0 ml) were added oxalyl chloride (43 μl, 0.489 mmol) and dimethylformamide (catalytic amount) at room temperature, and this was stirred for 1.5 hours as it was. An aquoeus sodium bicarbonate solution was added to neutralize it, followed by extraction with chloroform. This was dried with anhydrous sodium sulfate, and the solvent was distilled off under reduced pressure. The residue was purified by silica gel column chromatography (eluent: n-hexane-ethyl acetate) to obtain a compound 58 (133 mg) at a yield of 75%.

NMR (CDCl$_3$) δ: 4.58 (2H, d, J=6.0 Hz), 5.03 (2H, s), 5.36 (2H, s), 6.97-7.03 (4H, m), 7.28-7.52 (9H, m), 8.34 (1H, s), 10.21 (1H, s).

5) According to the method of synthesizing Example B-1, Example J-1 compound J-1 was synthesized.
melting point: 257-259° C.
NMR (DMSO-$d_6$) δ: 4.53 (2H, d, J=6.0H), 4.97 (2H, s), 5.27 (2H, s), 7.12-7.19 (4H, m), 7.34-7.43 (4H, m), 8.48 (1H, s), 10.25 (1H, t, J=6.0 Hz), 10.80 (1H, s).

The present invention further includes the following compounds.

[Chemical formula 67]

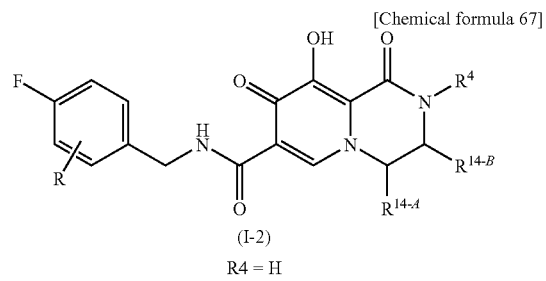

(I-2)
R4 = H

| No | R | R14-A | R14-B |
|---|---|---|---|
| 1 | —H | H | OH |
| 2 | —CF$_3$ | H | OH |
| 3 | —OMe | H | OH |
| 4 | —CH$_2$OMe | H | OH |
| 5 | —CH$_2$NMe$_2$ | H | OH |
| 6 | —CONHMe | H | OH |
| 7 | —CONMe$_2$ | H | OH |
| 8 | —PO(OEt)$_2$ | H | OH |
| 9 | —CH$_2$PO(OEt)$_2$ | H | OH |
| 10 | —NHSO$_2$Me | H | OH |
| 11 | —NMeSO$_2$Me | H | OH |
| 12 | —CH$_2$OH | H | OH |
| 13 | —OCF$_3$ | H | OH |
| 14 | —H | OH | H |
| 15 | —CF$_3$ | OH | H |
| 16 | —OMe | OH | H |
| 17 | —CH$_2$OMe | OH | H |
| 18 | —CH$_2$NMe$_2$ | OH | H |
| 19 | —CONHMe | OH | H |
| 20 | —CONMe$_2$ | OH | H |
| 21 | —PO(OEt)$_2$ | OH | H |
| 22 | —CH$_2$PO(OEt)$_2$ | OH | H |
| 23 | —NHSO$_2$Me | OH | H |
| 24 | —NMeSO$_2$Me | OH | H |
| 25 | —CH$_2$OH | OH | H |

-continued

[Chemical formula 67]

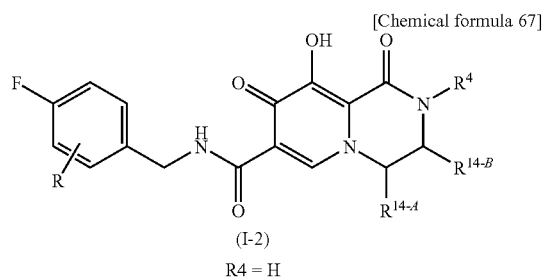

(I-2)
R4 = H

| No | R | R14-A | R14-B |
|----|---|-------|-------|
| 26 | —OCF₃ | OH | H |
| 27 | —H | H | H |
| 28 | —CF₃ | H | H |
| 29 | —OMe | H | H |
| 30 | —CH₂OMe | H | H |
| 31 | —CH₂NMe₂ | H | H |
| 32 | —CONHMe | H | H |
| 33 | —CONMe₂ | H | H |
| 34 | —PO(OEt)₂ | H | H |
| 35 | —CH₂PO(OEt)₂ | H | H |
| 36 | —NHSO₂Me | H | H |
| 37 | —NMeSO₂Me | H | H |
| 38 | —CH₂OH | H | H |
| 39 | —OCF₃ | H | H |
| 40 | —H | —CH₂NMe₂ | H |
| 41 | —CF₃ | —CH₂NMe₂ | H |
| 42 | —OMe | —CH₂NMe₂ | H |
| 43 | —CH₂OMe | —CH₂NMe₂ | H |
| 44 | —CH₂NMe₂ | —CH₂NMe₂ | H |
| 45 | —CONHMe | —CH₂NMe₂ | H |
| 46 | —CONMe₂ | —CH₂NMe₂ | H |
| 47 | —PO(OEt)₂ | —CH₂NMe₂ | H |
| 48 | —CH₂PO(OEt)₂ | —CH₂NMe₂ | H |
| 49 | —NHSO₂Me | —CH₂NMe₂ | H |
| 50 | —NMeSO₂Me | —CH₂NMe₂ | H |
| 51 | —CH₂OH | —CH₂NMe₂ | H |
| 52 | —OCF₃ | —CH₂NMe₂ | H |

[Chemical formula 68]

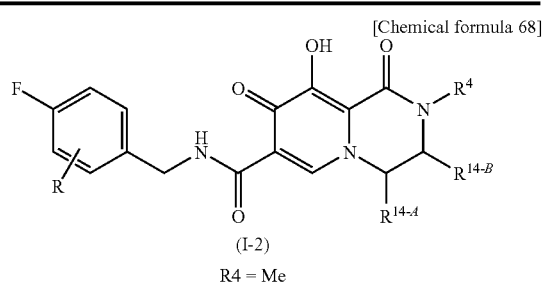

(I-2)
R4 = Me

| No | R | R14-A | R14-B |
|----|---|-------|-------|
| 1 | —H | H | OH |
| 2 | —CF₃ | H | OH |
| 3 | —OMe | H | OH |
| 4 | —CH₂OMe | H | OH |
| 5 | —CH₂NMe₂ | H | OH |
| 6 | —CONHMe | H | OH |
| 7 | —CONMe₂ | H | OH |
| 8 | —PO(OEt)₂ | H | OH |
| 9 | —CH₂PO(OEt)₂ | H | OH |
| 10 | —NHSO₂Me | H | OH |
| 11 | —NMeSO₂Me | H | OH |
| 12 | —CH₂OH | H | OH |
| 13 | —OCF₃ | H | OH |
| 14 | —H | OH | H |

[Chemical formula 68]

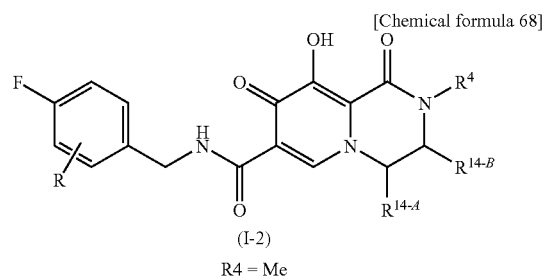

(I-2)
R4 = Me

| No | R | R14-A | R14-B |
|----|---|-------|-------|
| 15 | —CF₃ | OH | H |
| 16 | —OMe | OH | H |
| 17 | —CH₂OMe | OH | H |
| 18 | —CH₂NMe₂ | OH | H |
| 19 | —CONHMe | OH | H |
| 20 | —CONMe₂ | OH | H |
| 21 | —PO(OEt)₂ | OH | H |
| 22 | —CH₂PO(OEt)₂ | OH | H |
| 23 | —NHSO₂Me | OH | H |
| 24 | —NMeSO₂Me | OH | H |
| 25 | —CH₂OH | OH | H |
| 26 | —OCF₃ | OH | H |
| 27 | —H | H | H |
| 28 | —CF₃ | H | H |
| 29 | —OMe | H | H |
| 30 | —CH₂OMe | H | H |
| 31 | —CH₂NMe₂ | H | H |
| 32 | —CONHMe | H | H |
| 33 | —CONMe₂ | H | H |
| 34 | —PO(OEt)₂ | H | H |
| 35 | —CH₂PO(OEt)₂ | H | H |
| 36 | —NHSO₂Me | H | H |
| 37 | —NMeSO₂Me | H | H |
| 38 | —CH₂OH | H | H |
| 39 | —OCF₃ | H | H |
| 40 | —H | —CH₂NMe₂ | H |
| 41 | —CF₃ | —CH₂NMe₂ | H |
| 42 | —OMe | —CH₂NMe₂ | H |
| 43 | —CH₂OMe | —CH₂NMe₂ | H |
| 44 | —CH₂NMe₂ | —CH₂NMe₂ | H |
| 45 | —CONHMe | —CH₂NMe₂ | H |
| 46 | —CONMe₂ | —CH₂NMe₂ | H |
| 47 | —PO(OEt)₂ | —CH₂NMe₂ | H |
| 48 | —CH₂PO(OEt)₂ | —CH₂NMe₂ | H |
| 49 | —NHSO₂Me | —CH₂NMe₂ | H |
| 50 | —NMeSO₂Me | —CH₂NMe₂ | H |
| 51 | —CH₂OH | —CH₂NMe₂ | H |
| 52 | —OCF₃ | —CH₂NMe₂ | H |

[Chemical formula 69]

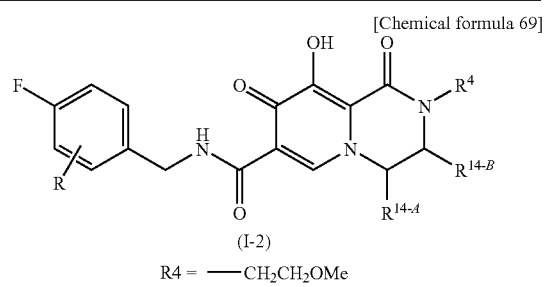

(I-2)
R4 = —CH₂CH₂OMe

| No | R | R14-A | R14-B |
|----|---|-------|-------|
| 1 | —H | H | OH |
| 2 | —CF₃ | H | OH |
| 3 | —OMe | H | OH |

-continued

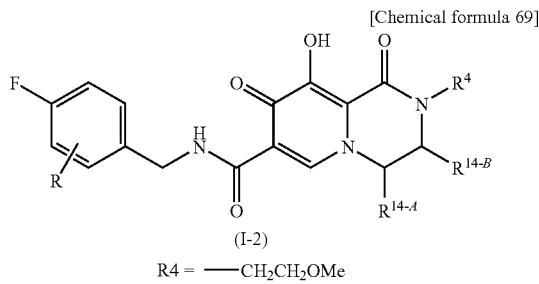

(I-2)
R4 = —CH$_2$CH$_2$OMe

| No | R | R14-A | R14-B |
|---|---|---|---|
| 4 | —CH$_2$OMe | H | OH |
| 5 | —CH$_2$NMe$_2$ | H | OH |
| 6 | —CONHMe | H | OH |
| 7 | —CONMe$_2$ | H | OH |
| 8 | —PO(OEt)$_2$ | H | OH |
| 9 | —CH$_2$PO(OEt)$_2$ | H | OH |
| 10 | —NHSO$_2$Me | H | OH |
| 11 | —NMeSO$_2$Me | H | OH |
| 12 | —CH$_2$OH | H | OH |
| 13 | —OCF$_3$ | H | OH |
| 14 | —H | OH | H |
| 15 | —CF$_3$ | OH | H |
| 16 | —OMe | OH | H |
| 17 | —CH$_2$OMe | OH | H |
| 18 | —CH$_2$NMe$_2$ | OH | H |
| 19 | —CONHMe | OH | H |
| 20 | —CONMe$_2$ | OH | H |
| 21 | —PO(OEt)$_2$ | OH | H |
| 22 | —CH$_2$PO(OEt)$_2$ | OH | H |
| 23 | —NHSO$_2$Me | OH | H |
| 24 | —NMeSO$_2$Me | OH | H |
| 25 | —CH$_2$OH | OH | H |
| 26 | —OCF$_3$ | OH | H |
| 27 | —H | H | H |
| 28 | —CF$_3$ | H | H |
| 29 | —OMe | H | H |
| 30 | —CH$_2$OMe | H | H |
| 31 | —CH$_2$NMe$_2$ | H | H |
| 32 | —CONHMe | H | H |
| 33 | —CONMe$_2$ | H | H |
| 34 | —PO(OEt)$_2$ | H | H |
| 35 | —CH$_2$PO(OEt)$_2$ | H | H |
| 36 | —NHSO$_2$Me | H | H |
| 37 | —NMeSO$_2$Me | H | H |
| 38 | —CH$_2$OH | H | H |
| 39 | —OCF$_3$ | H | H |
| 40 | —H | —CH$_2$NMe$_2$ | H |
| 41 | —CF$_3$ | —CH$_2$NMe$_2$ | H |
| 42 | —OMe | —CH$_2$NMe$_2$ | H |
| 43 | —CH$_2$OMe | —CH$_2$NMe$_2$ | H |
| 44 | —CH$_2$NMe$_2$ | —CH$_2$NMe$_2$ | H |
| 45 | —CONHMe | —CH$_2$NMe$_2$ | H |
| 46 | —CONMe$_2$ | —CH$_2$NMe$_2$ | H |
| 47 | —PO(OEt)$_2$ | —CH$_2$NMe$_2$ | H |
| 48 | —CH$_2$PO(OEt)$_2$ | —CH$_2$NMe$_2$ | H |
| 49 | —NHSO$_2$Me | —CH$_2$NMe$_2$ | H |
| 50 | —NMeSO$_2$Me | —CH$_2$NMe$_2$ | H |
| 51 | —CH$_2$OH | —CH$_2$NMe$_2$ | H |
| 52 | —OCF$_3$ | —CH$_2$NMe$_2$ | H |

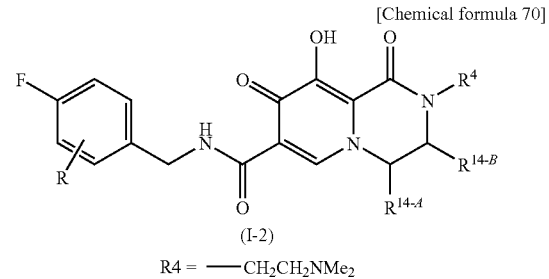

(I-2)
R4 = —CH$_2$CH$_2$NMe$_2$

| No | R | R14-A | R14-B |
|---|---|---|---|
| 1 | —H | H | OH |
| 2 | —CF$_3$ | H | OH |
| 3 | —OMe | H | OH |
| 4 | —CH$_2$OMe | H | OH |
| 5 | —CH$_2$NMe$_2$ | H | OH |
| 6 | —CONHMe | H | OH |
| 7 | —CONMe$_2$ | H | OH |
| 8 | —PO(OEt)$_2$ | H | OH |
| 9 | —CH$_2$PO(OEt)$_2$ | H | OH |
| 10 | —NHSO$_2$Me | H | OH |
| 11 | —NMeSO$_2$Me | H | OH |
| 12 | —CH$_2$OH | H | OH |
| 13 | —OCF$_3$ | H | OH |
| 14 | —H | OH | H |
| 15 | —CF$_3$ | OH | H |
| 16 | —OMe | OH | H |
| 17 | —CH$_2$OMe | OH | H |
| 18 | —CH$_2$NMe$_2$ | OH | H |
| 19 | —CONHMe | OH | H |
| 20 | —CONMe$_2$ | OH | H |
| 21 | —PO(OEt)$_2$ | OH | H |
| 22 | —CH$_2$PO(OEt)$_2$ | OH | H |
| 23 | —NHSO$_2$Me | OH | H |
| 24 | —NMeSO$_2$Me | OH | H |
| 25 | —CH$_2$OH | OH | H |
| 26 | —OCF$_3$ | OH | H |
| 27 | —H | H | H |
| 28 | —CF$_3$ | H | H |
| 29 | —OMe | H | H |
| 30 | —CH$_2$OMe | H | H |
| 31 | —CH$_2$NMe$_2$ | H | H |
| 32 | —CONHMe | H | H |
| 33 | —CONMe$_2$ | H | H |
| 34 | —PO(OEt)$_2$ | H | H |
| 35 | —CH$_2$PO(OEt)$_2$ | H | H |
| 36 | —NHSO$_2$Me | H | H |
| 37 | —NMeSO$_2$Me | H | H |
| 38 | —CH$_2$OH | H | H |
| 39 | —OCF$_3$ | H | H |
| 40 | —H | —CH$_2$NMe$_2$ | H |
| 41 | —CF$_3$ | —CH$_2$NMe$_2$ | H |
| 42 | —OMe | —CH$_2$NMe$_2$ | H |
| 43 | —CH$_2$OMe | —CH$_2$NMe$_2$ | H |
| 44 | —CH$_2$NMe$_2$ | —CH$_2$NMe$_2$ | H |
| 45 | —CONHMe | —CH$_2$NMe$_2$ | H |
| 46 | —CONMe$_2$ | —CH$_2$NMe$_2$ | H |
| 47 | —PO(OEt)$_2$ | —CH$_2$NMe$_2$ | H |
| 48 | —CH$_2$PO(OEt)$_2$ | —CH$_2$NMe$_2$ | H |
| 49 | —NHSO$_2$Me | —CH$_2$NMe$_2$ | H |
| 50 | —NMeSO$_2$Me | —CH$_2$NMe$_2$ | H |
| 51 | —CH$_2$OH | —CH$_2$NMe$_2$ | H |
| 52 | —OCF$_3$ | —CH$_2$NMe$_2$ | H |

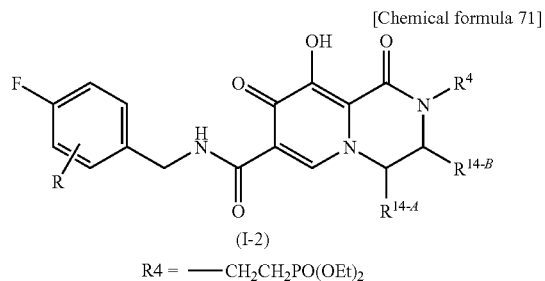

(I-2)
R4 = —CH₂CH₂PO(OEt)₂

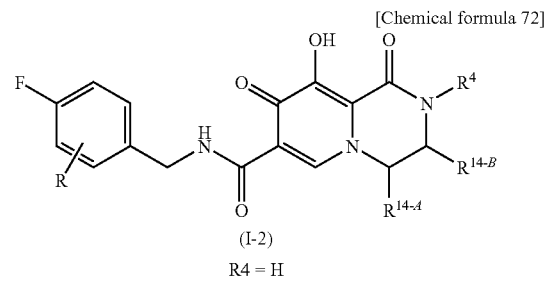

(I-2)
R4 = H

| No | R | R14-A | R14-B | | No | R | R14-A | R14-B |
|----|---|-------|-------|---|----|---|-------|-------|
| 1 | —H | H | OH | | 1 | —H | H | OH |
| 2 | —CF₃ | H | OH | | 2 | —CF₃ | H | OH |
| 3 | —OMe | H | OH | | 3 | —OMe | H | OH |
| 4 | —CH₂OMe | H | OH | | 4 | —CH₂OMe | H | OH |
| 5 | —CH₂NMe₂ | H | OH | | 5 | —CH₂NMe₂ | H | OH |
| 6 | —CONHMe | H | OH | | 6 | —CONHMe | H | OH |
| 7 | —CONMe₂ | H | OH | | 7 | —CONMe₂ | H | OH |
| 8 | —PO(OEt)₂ | H | OH | | 8 | —PO(OEt)₂ | H | OH |
| 9 | —CH₂PO(OEt)₂ | H | OH | | 9 | —CH₂PO(OEt)₂ | H | OH |
| 10 | —NHSO₂Me | H | OH | | 10 | —NHSO₂Me | H | OH |
| 11 | —NMeSO₂Me | H | OH | | 11 | —NMeSO₂Me | H | OH |
| 12 | —CH₂OH | H | OH | | 12 | —CH₂OH | H | OH |
| 13 | —OCF₃ | H | OH | | 13 | —OCF₃ | H | OH |
| 14 | —H | OH | H | | 14 | —H | OH | H |
| 15 | —CF₃ | OH | H | | 15 | —CF₃ | OH | H |
| 16 | —OMe | OH | H | | 16 | —OMe | OH | H |
| 17 | —CH₂OMe | OH | H | | 17 | —CH₂OMe | OH | H |
| 18 | —CH₂NMe₂ | OH | H | | 18 | —CH₂NMe₂ | OH | H |
| 19 | —CONHMe | OH | H | | 19 | —CONHMe | OH | H |
| 20 | —CONMe₂ | OH | H | | 20 | —CONMe₂ | OH | H |
| 21 | —PO(OEt)₂ | OH | H | | 21 | —PO(OEt)₂ | OH | H |
| 22 | —CH₂PO(OEt)₂ | OH | H | | 22 | —CH₂PO(OEt)₂ | OH | H |
| 23 | —NHSO₂Me | OH | H | | 23 | —NHSO₂Me | OH | H |
| 24 | —NMeSO₂Me | OH | H | | 24 | —NMeSO₂Me | OH | H |
| 25 | —CH₂OH | OH | H | | 25 | —CH₂OH | OH | H |
| 26 | —OCF₃ | OH | H | | 26 | —OCF₃ | OH | H |
| 27 | —H | H | H | | 27 | —H | H | H |
| 28 | —CF₃ | H | H | | 28 | —CF₃ | H | H |
| 29 | —OMe | H | H | | 29 | —OMe | H | H |
| 30 | —CH₂OMe | H | H | | 30 | —CH₂OMe | H | H |
| 31 | —CH₂NMe₂ | H | H | | 31 | —CH₂NMe₂ | H | H |
| 32 | —CONHMe | H | H | | 32 | —CONHMe | H | H |
| 33 | —CONMe₂ | H | H | | 33 | —CONMe₂ | H | H |
| 34 | —PO(OEt)₂ | H | H | | 34 | —PO(OEt)₂ | H | H |
| 35 | —CH₂PO(OEt)₂ | H | H | | 35 | —CH₂PO(OEt)₂ | H | H |
| 36 | —NHSO₂Me | H | H | | 36 | —NHSO₂Me | H | H |
| 37 | —NMeSO₂Me | H | H | | 37 | —NMeSO₂Me | H | H |
| 38 | —CH₂OH | H | H | | 38 | —CH₂OH | H | H |
| 39 | —OCF₃ | H | H | | 39 | —OCF₃ | H | H |
| 40 | —H | —CH₂NMe₂ | H | | 40 | —H | —CH₂NMe₂ | H |
| 41 | —CF₃ | —CH₂NMe₂ | H | | 41 | —CF₃ | —CH₂NMe₂ | H |
| 42 | —OMe | —CH₂NMe₂ | H | | 42 | —OMe | —CH₂NMe₂ | H |
| 43 | —CH₂OMe | —CH₂NMe₂ | H | | 43 | —CH₂OMe | —CH₂NMe₂ | H |
| 44 | —CH₂NMe₂ | —CH₂NMe₂ | H | | 44 | —CH₂NMe₂ | —CH₂NMe₂ | H |
| 45 | —CONHMe | —CH₂NMe₂ | H | | 45 | —CONHMe | —CH₂NMe₂ | H |
| 46 | —CONMe₂ | —CH₂NMe₂ | H | | 46 | —CONMe₂ | —CH₂NMe₂ | H |
| 47 | —PO(OEt)₂ | —CH₂NMe₂ | H | | 47 | —PO(OEt)₂ | —CH₂NMe₂ | H |
| 48 | —CH₂PO(OEt)₂ | —CH₂NMe₂ | H | | 48 | —CH₂PO(OEt)₂ | —CH₂NMe₂ | H |
| 49 | —NHSO₂Me | —CH₂NMe₂ | H | | 49 | —NHSO₂Me | —CH₂NMe₂ | H |
| 50 | —NMeSO₂Me | —CH₂NMe₂ | H | | 50 | —NMeSO₂Me | —CH₂NMe₂ | H |
| 51 | —CH₂OH | —CH₂NMe₂ | H | | 51 | —CH₂OH | —CH₂NMe₂ | H |
| 52 | —OCF₃ | —CH₂NMe₂ | H | | 52 | —OCF₃ | —CH₂NMe₂ | H |

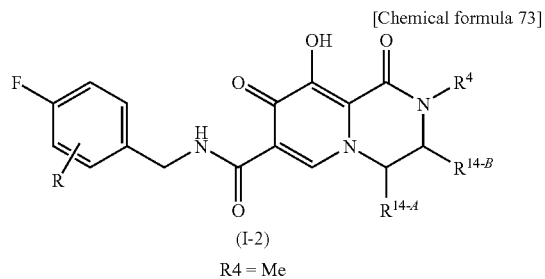

(I-2)
R4 = Me

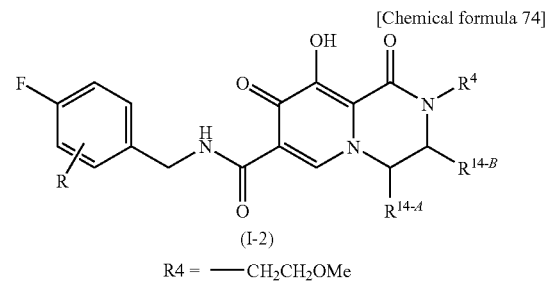

(I-2)
R4 = —CH$_2$CH$_2$OMe

| No | R | R14-A | R14-B |
|---|---|---|---|
| 1 | —H | H | OH |
| 2 | —CF$_3$ | H | OH |
| 3 | —OMe | H | OH |
| 4 | —CH$_2$OMe | H | OH |
| 5 | —CH$_2$NMe$_2$ | H | OH |
| 6 | —CONHMe | H | OH |
| 7 | —CONMe$_2$ | H | OH |
| 8 | —PO(OEt)$_2$ | H | OH |
| 9 | —CH$_2$PO(OEt)$_2$ | H | OH |
| 10 | —NHSO$_2$Me | H | OH |
| 11 | —NMeSO$_2$Me | H | OH |
| 12 | —CH$_2$OH | H | OH |
| 13 | —OCF$_3$ | H | OH |
| 14 | —H | OH | H |
| 15 | —CF$_3$ | OH | H |
| 16 | —OMe | OH | H |
| 17 | —CH$_2$OMe | OH | H |
| 18 | —CH$_2$NMe$_2$ | OH | H |
| 19 | —CONHMe | OH | H |
| 20 | —CONMe$_2$ | OH | H |
| 21 | —PO(OEt)$_2$ | OH | H |
| 22 | —CH$_2$PO(OEt)$_2$ | OH | H |
| 23 | —NHSO$_2$Me | OH | H |
| 24 | —NMeSO$_2$Me | OH | H |
| 25 | —CH$_2$OH | OH | H |
| 26 | —OCF$_3$ | OH | H |
| 27 | —H | H | H |
| 28 | —CF$_3$ | H | H |
| 29 | —OMe | H | H |
| 30 | —CH$_2$OMe | H | H |
| 31 | —CH$_2$NMe$_2$ | H | H |
| 32 | —CONHMe | H | H |
| 33 | —CONMe$_2$ | H | H |
| 34 | —PO(OEt)$_2$ | H | H |
| 35 | —CH$_2$PO(OEt)$_2$ | H | H |
| 36 | —NHSO$_2$Me | H | H |
| 37 | —NMeSO$_2$Me | H | H |
| 38 | —CH$_2$OH | H | H |
| 39 | —OCF$_3$ | H | H |
| 40 | —H | —CH$_2$NMe$_2$ | H |
| 41 | —CF$_3$ | —CH$_2$NMe$_2$ | H |
| 42 | —OMe | —CH$_2$NMe$_2$ | H |
| 43 | —CH$_2$OMe | —CH$_2$NMe$_2$ | H |
| 44 | —CH$_2$NMe$_2$ | —CH$_2$NMe$_2$ | H |
| 45 | —CONHMe | —CH$_2$NMe$_2$ | H |
| 46 | —CONMe$_2$ | —CH$_2$NMe$_2$ | H |
| 47 | —PO(OEt)$_2$ | —CH$_2$NMe$_2$ | H |
| 48 | —CH$_2$PO(OEt)$_2$ | —CH$_2$NMe$_2$ | H |
| 49 | —NHSO$_2$Me | —CH$_2$NMe$_2$ | H |
| 50 | —NMeSO$_2$Me | —CH$_2$NMe$_2$ | H |
| 51 | —CH$_2$OH | —CH$_2$NMe$_2$ | H |
| 52 | —OCF$_3$ | —CH$_2$NMe$_2$ | H |

| No | R | R14-A | R14-B |
|---|---|---|---|
| 1 | —H | H | OH |
| 2 | —CF$_3$ | H | OH |
| 3 | —OMe | H | OH |
| 4 | —CH$_2$OMe | H | OH |
| 5 | —CH$_2$NMe$_2$ | H | OH |
| 6 | —CONHMe | H | OH |
| 7 | —CONMe$_2$ | H | OH |
| 8 | —PO(OEt)$_2$ | H | OH |
| 9 | —CH$_2$PO(OEt)$_2$ | H | OH |
| 10 | —NHSO$_2$Me | H | OH |
| 11 | —NMeSO$_2$Me | H | OH |
| 12 | —CH$_2$OH | H | OH |
| 13 | —OCF$_3$ | H | OH |
| 14 | —H | OH | H |
| 15 | —CF$_3$ | OH | H |
| 16 | —OMe | OH | H |
| 17 | —CH$_2$OMe | OH | H |
| 18 | —CH$_2$NMe$_2$ | OH | H |
| 19 | —CONHMe | OH | H |
| 20 | —CONMe$_2$ | OH | H |
| 21 | —PO(OEt)$_2$ | OH | H |
| 22 | —CH$_2$PO(OEt)$_2$ | OH | H |
| 23 | —NHSO$_2$Me | OH | H |
| 24 | —NMeSO$_2$Me | OH | H |
| 25 | —CH$_2$OH | OH | H |
| 26 | —OCF$_3$ | OH | H |
| 27 | —H | H | H |
| 28 | —CF$_3$ | H | H |
| 29 | —OMe | H | H |
| 30 | —CH$_2$OMe | H | H |
| 31 | —CH$_2$NMe$_2$ | H | H |
| 32 | —CONHMe | H | H |
| 33 | —CONMe$_2$ | H | H |
| 34 | —PO(OEt)$_2$ | H | H |
| 35 | —CH$_2$PO(OEt)$_2$ | H | H |
| 36 | —NHSO$_2$Me | H | H |
| 37 | —NMeSO$_2$Me | H | H |
| 38 | —CH$_2$OH | H | H |
| 39 | —OCF$_3$ | H | H |
| 40 | —H | —CH$_2$NMe$_2$ | H |
| 41 | —CF$_3$ | —CH$_2$NMe$_2$ | H |
| 42 | —OMe | —CH$_2$NMe$_2$ | H |
| 43 | —CH$_2$OMe | —CH$_2$NMe$_2$ | H |
| 44 | —CH$_2$NMe$_2$ | —CH$_2$NMe$_2$ | H |
| 45 | —CONHMe | —CH$_2$NMe$_2$ | H |
| 46 | —CONMe$_2$ | —CH$_2$NMe$_2$ | H |
| 47 | —PO(OEt)$_2$ | —CH$_2$NMe$_2$ | H |
| 48 | —CH$_2$PO(OEt)$_2$ | —CH$_2$NMe$_2$ | H |
| 49 | —NHSO$_2$Me | —CH$_2$NMe$_2$ | H |
| 50 | —NMeSO$_2$Me | —CH$_2$NMe$_2$ | H |
| 51 | —CH$_2$OH | —CH$_2$NMe$_2$ | H |
| 52 | —OCF$_3$ | —CH$_2$NMe$_2$ | H |

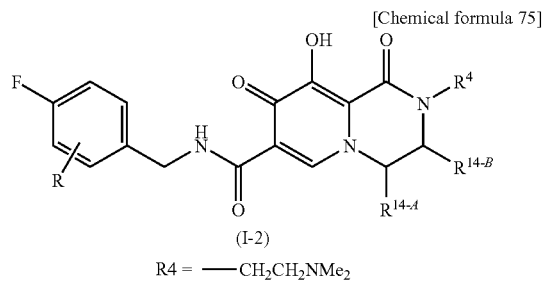

(I-2)

R4 = —CH₂CH₂NMe₂

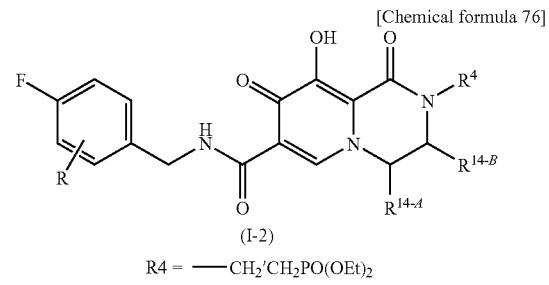

(I-2)

R4 = —CH₂'CH₂PO(OEt)₂

| No | R | R14-A | R14-B |
|---|---|---|---|
| 1 | —H | H | OH |
| 2 | —CF₃ | H | OH |
| 3 | —OMe | H | OH |
| 4 | —CH₂OMe | H | OH |
| 5 | —CH₂NMe₂ | H | OH |
| 6 | —CONHMe | H | OH |
| 7 | —CONMe₂ | H | OH |
| 8 | —PO(OEt)₂ | H | OH |
| 9 | —CH₂PO(OEt)₂ | H | OH |
| 10 | —NHSO₂Me | H | OH |
| 11 | —NMeSO₂Me | H | OH |
| 12 | —CH₂OH | H | OH |
| 13 | —OCF₃ | H | OH |
| 14 | —H | OH | H |
| 15 | —CF₃ | OH | H |
| 16 | —OMe | OH | H |
| 17 | —CH₂OMe | OH | H |
| 18 | —CH₂NMe₂ | OH | H |
| 19 | —CONHMe | OH | H |
| 20 | —CONMe₂ | OH | H |
| 21 | —PO(OEt)₂ | OH | H |
| 22 | —CH₂PO(OEt)₂ | OH | H |
| 23 | —NHSO₂Me | OH | H |
| 24 | —NMeSO₂Me | OH | H |
| 25 | —CH₂OH | OH | H |
| 26 | —OCF₃ | OH | H |
| 27 | —H | H | H |
| 28 | —CF₃ | H | H |
| 29 | —OMe | H | H |
| 30 | —CH₂OMe | H | H |
| 31 | —CH₂NMe₂ | H | H |
| 32 | —CONHMe | H | H |
| 33 | —CONMe₂ | H | H |
| 34 | —PO(OEt)₂ | H | H |
| 35 | —CH₂PO(OEt)₂ | H | H |
| 36 | —NHSO₂Me | H | H |
| 37 | —NMeSO₂Me | H | H |
| 38 | —CH₂OH | H | H |
| 39 | —OCF₃ | H | H |
| 40 | —H | —CH₂NMe₂ | H |
| 41 | —CF₃ | —CH₂NMe₂ | H |
| 42 | —OMe | —CH₂NMe₂ | H |
| 43 | —CH₂OMe | —CH₂NMe₂ | H |
| 44 | —CH₂NMe₂ | —CH₂NMe₂ | H |
| 45 | —CONHMe | —CH₂NMe₂ | H |
| 46 | —CONMe₂ | —CH₂NMe₂ | H |
| 47 | —PO(OEt)₂ | —CH₂NMe₂ | H |
| 48 | —CH₂PO(OEt)₂ | —CH₂NMe₂ | H |
| 49 | —NHSO₂Me | —CH₂NMe₂ | H |
| 50 | —NMeSO₂Me | —CH₂NMe₂ | H |
| 51 | —CH₂OH | —CH₂NMe₂ | H |
| 52 | —OCF₃ | —CH₂NMe₂ | H |

| No | R | R14-A | R14-B |
|---|---|---|---|
| 1 | —H | H | OH |
| 2 | —CF₃ | H | OH |
| 3 | —OMe | H | OH |
| 4 | —CH₂OMe | H | OH |
| 5 | —CH₂NMe₂ | H | OH |
| 6 | —CONHMe | H | OH |
| 7 | —CONMe₂ | H | OH |
| 8 | —PO(OEt)₂ | H | OH |
| 9 | —CH₂PO(OEt)₂ | H | OH |
| 10 | —NHSO₂Me | H | OH |
| 11 | —NMeSO₂Me | H | OH |
| 12 | —CH₂OH | H | OH |
| 13 | —OCF₃ | H | OH |
| 14 | —H | OH | H |
| 15 | —CF₃ | OH | H |
| 16 | —OMe | OH | H |
| 17 | —CH₂OMe | OH | H |
| 18 | —CH₂NMe₂ | OH | H |
| 19 | —CONHMe | OH | H |
| 20 | —CONMe₂ | OH | H |
| 21 | —PO(OEt)₂ | OH | H |
| 22 | —CH₂PO(OEt)₂ | OH | H |
| 23 | —NHSO₂Me | OH | H |
| 24 | —NMeSO₂Me | OH | H |
| 25 | —CH₂OH | OH | H |
| 26 | —OCF₃ | OH | H |
| 27 | —H | H | H |
| 28 | —CF₃ | H | H |
| 29 | —OMe | H | H |
| 30 | —CH₂OMe | H | H |
| 31 | —CH₂NMe₂ | H | H |
| 32 | —CONHMe | H | H |
| 33 | —CONMe₂ | H | H |
| 34 | —PO(OEt)₂ | H | H |
| 35 | —CH₂PO(OEt)₂ | H | H |
| 36 | —NHSO₂Me | H | H |
| 37 | —NMeSO₂Me | H | H |
| 38 | —CH₂OH | H | H |
| 39 | —OCF₃ | H | H |
| 40 | —H | —CH₂NMe₂ | H |
| 41 | —CF₃ | —CH₂NMe₂ | H |
| 42 | —OMe | —CH₂NMe₂ | H |
| 43 | —CH₂OMe | —CH₂NMe₂ | H |
| 44 | —CH₂NMe₂ | —CH₂NMe₂ | H |
| 45 | —CONHMe | —CH₂NMe₂ | H |
| 46 | —CONMe₂ | —CH₂NMe₂ | H |
| 47 | —PO(OEt)₂ | —CH₂NMe₂ | H |
| 48 | —CH₂PO(OEt)₂ | —CH₂NMe₂ | H |
| 49 | —NHSO₂Me | —CH₂NMe₂ | H |
| 50 | —NMeSO₂Me | —CH₂NMe₂ | H |
| 51 | —CH₂OH | —CH₂NMe₂ | H |
| 52 | —OCF₃ | —CH₂NMe₂ | H |

Experimental Example 1

The HIV integrase inhibitory activity was investigated based on the following assay method.

(1) Preparation of DNA Solution

By the same method as that described in Experimental Example 1 of WO 2004/024693, a substrate DNA solution (2 pmol/ml) and a target DNA solution (5 pmol/ml) were prepared. After each target DNA solution was once boiled, a temperature was slowly lowered to anneal complementary chains, which was used. Each sequence of a substrate DNA and a target DNA is as described in the same Experimental Example.

(2) Measurement of Inhibition Rate ($IC_{50}$ Value)

Streptavidin (manufactured by Vector Laboratories) was dissolved in a 0.1M carbonate buffer solution (composition: 90 mM $Na_2CO_3$, 10 mM $NaHCO_3$) to a concentration of 40 µg/ml. Each 50 ml of this solution was added to a well of an immunoplate (manufactured by NUNC), and this is allowed to stand at 4° C. overnight to adsorb. Then, each well was washed with a phosphate buffer (composition: 13.7 mM NaCl, 0.27 mM KCl, 0.43 mM $Na_2HPO_4$, 0.14 mM $KH_2PO_4$) two times, and 300 ml of a phosphate buffer containing 1% skim milk was added to block it for 30 minutes. Further, each well was washed with a phosphate buffer two times, 50 ml of a substrate DNA solution (2 pmol/ml) was added to adsorb at room temperature for 30 minutes while shaking, and this was washed with a phosphate buffer two times and, then, distilled water once.

Then, to each well prepared as described above were added 12 ml of a buffer (composition: 150 mM MOPS (pH7.2), 75 mM $MnCl_2$, 50 mM 2-mercaptoethanol, 25% glycerol, 500 µg/ml bovine serum albumin-fraction V), and 51 ml of a reaction solution prepared from 39 ml of distilled water. Then, 9 ml of an integrase solution (30 pmol) was added, and the mixture was mixed well. To a well as a negative control (NC) was added 9 ml of a diluting solution (composition: 20 mM MOPS (pH7.2), 400 mM potassium glutamete, 1 mM EDTA, 0.1% NP-40, 20% glycerol, 1 mM DTT, 4 M urea), and this was mixed well using a plate mixer.

After the plate was incubated at 30° C. for 60 minutes, the reaction solution was discarded, followed by washing with 250 ml of a washing buffer (composition: 150 mM MOPS (pH7.2), 50 mM 2-mercaptoethanol, 25% glycerol, 500 µg/ml bovine serum albumin-fraction V) three times.

Then, to each well were added 12 µl of a buffer (composition: 150 mM MOPS (pH7.2), 75 mM $MgCl_2$, 50 mM 2-mercaptoethanol, 25% glycerol, 500 µg/ml bovine serum albumin-fraction V) 12 ml, and 53 ml of a reaction solution prepared from 41 ml of distilled water. Further, 6 ml of a solution of a test compound in DMSO was added to each well, and 6 ml of DMSO was added to a well as a positive control (PC), followed by mixing well using a plate mixer. After the plate was incubated at 30° C. for 30 minutes, 1 µl of a target DNA (5 pmol/ml) was added, and this was mixed well using a plate mixer.

After each plate was incubated at 30° C. for 10 minutes, the reaction solution was discarded, followed by washing with a phosphate buffer two times. Then, an anti-digoxigenin antibody labeled with alkaline phosphatase (sheep Fab fragment: manufactured by Boehringer) was diluted 2000-fold with an antibody diluting solution, 100 ml of the diluent was added to bind at 30° C. for 1 hour, and this was washed successively with a phosphate buffer containing 0.05% Tween20 two times, and a phosphate buffer once. Then, 150 ml of an alkaline phosphatase coloring buffer (composition: 10 mM paranitrophenyl phosphate (manufactured by Vector Laboratories), 5 mM $MgCl_2$, 100 mM NaCl, 100 mM Tris-HCl (pH 9.5)) was added to react at 30° C. for 2 hours, 50 ml of a 1N NaOH solution was added to stop the reaction, an absorbance (OD405 nm) of each well was measured, and an inhibition rate ($IC_{50}$) was obtained according to the following calculation equation.

Inhibition rate(%)=100[1−{(C abs.−NC abs.)/(PC abs.−NC abs.)}]

C abs.; absorbance of well of compound

NC abs.: absorbance of NC

PC abs.: absorbance of PC

Results are shown below.

TABLE 1

| Example No. | Integrase inhibitory activity (IC50, ng/ml) |
| --- | --- |
| A-30 | 1.0 |
| D-41 | 3.2 |
| E-1 | 5.0 |

The present compound showed the strong integrase inhibitory activity against HIV.

Formulation Example

A term "active ingredient" means the present compound, a tautomer thereof, a pharmaceutically acceptable salt thereof, or a solvate thereof.

Formulation Example 1

A hard gelatin capsule is prepared using the following ingredients:

| | dose (mg/capsule) |
| --- | --- |
| Active ingredient | 250 |
| Starch (dried) | 200 |
| Magnesium stearate | 10 |
| Total | 460 mg |

Formulation Example 2

A tablet is prepared using the following ingredients:

| | dose (mg/tablet) |
| --- | --- |
| Active ingredient | 250 |
| Cellulose (microcrystalline) | 400 |
| Silicon dioxide (fumed) | 10 |
| Stearic acid | 5 |
| Total | 665 mg |

Ingredients are mixed, and compressed to obtain tablets, each weighing 665 mg.

The invention claimed is:
1. A compound represented by the formula:

[Chemical formula 12]

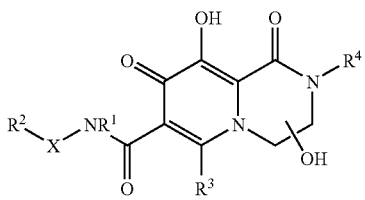

(I-4)

(wherein,

R$^1$ is hydrogen or lower alkyl;

X is a single bond, a heteroatom group selected from 0, S, SO, SO$_2$ and NH, or lower alkylene or lower alkenylene each may be intervened by the heteroatom group;

R$^2$ is optionally substituted aryl;

R$^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

R$^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from group consisting O, S, SO, SO$_2$, NR$^a$ (R$^a$ is hydrogen or lower alkyl), —N= and =N—)), or a pharmaceutically acceptable salt thereof.

2. A compound according to claim 1, or a pharmaceutically acceptable salt thereof, wherein R$^1$ is hydrogen; X is lower alkylene; R$^2$ is phenyl, or phenyl substituted with at least halogen; and R$^3$ is hydrogen, halogen, hydroxy, lower alkyl, lower alkenyl, lower alkoxy, lower alkenyloxy or optionally substituted amino.

3. A pharmaceutical composition, containing a compound as defined in claim 1 or a pharmaceutically acceptable salt thereof, and a pharmaceutically acceptable carrier or diluent.

* * * * *